United States Patent
Bergeron et al.

(10) Patent No.: US 7,799,795 B2
(45) Date of Patent: *Sep. 21, 2010

(54) ARYL NITRILE COMPOUNDS AND COMPOSITIONS AND THEIR USES IN TREATING INFLAMMATORY AND RELATED DISORDERS

(75) Inventors: Philippe Bergeron, San Mateo, CA (US); Xiaoqi Chen, Palo Alto, CA (US); Xiaohui Du, Foster City, CA (US); Jeffrey Deignan, San Francisco, CA (US); Jason A. Duquette, San Mateo, CA (US); Darin Gustin, Half Moon Bay, CA (US); Julio C. Medina, San Carlos, CA (US); Jeffrey T. Mihalic, San Francisco, CA (US); George R. Tonn, San Carlos, CA (US)

(73) Assignee: Amgen Inc., Thousand Oaks, CA (US)

( * ) Notice: Subject to any disclaimer, the term of this patent is extended or adjusted under 35 U.S.C. 154(b) by 499 days.

This patent is subject to a terminal disclaimer.

(21) Appl. No.: 11/475,653

(22) Filed: Jun. 26, 2006

(65) Prior Publication Data

US 2007/0015773 A1    Jan. 18, 2007

Related U.S. Application Data

(60) Provisional application No. 60/694,469, filed on Jun. 27, 2005.

(51) Int. Cl.
| | |
|---|---|
| *C07D 471/04* | (2006.01) |
| *A61K 31/519* | (2006.01) |
| *A61P 29/00* | (2006.01) |
| *A61P 11/06* | (2006.01) |
| *A61P 27/14* | (2006.01) |
| *A61P 19/02* | (2006.01) |
| *A61P 9/10* | (2006.01) |
| *A61P 17/06* | (2006.01) |
| *C07D 487/04* | (2006.01) |
| *C07D 513/04* | (2006.01) |
| *C07D 239/26* | (2006.01) |
| *C07D 233/22* | (2006.01) |
| *C07D 495/04* | (2006.01) |
| *C07D 491/04* | (2006.01) |
| *C07D 233/68* | (2006.01) |
| *C07D 235/10* | (2006.01) |
| *C07D 239/90* | (2006.01) |

(52) U.S. Cl. ............... 514/264.1; 544/279; 544/282; 544/335; 544/254; 544/262; 544/278; 544/255; 544/280; 544/287; 546/121; 546/281; 548/154; 548/333.5; 548/336.1; 548/309.7

(58) Field of Classification Search .............. 514/264.1; 544/279

See application file for complete search history.

(56) References Cited

U.S. PATENT DOCUMENTS

| | | | |
|---|---|---|---|
| 5,202,322 A | 4/1993 | Allen et al. | |
| 5,256,667 A | 10/1993 | Allen et al. | |
| 5,756,502 A | 5/1998 | Padia | |
| 5,869,665 A | 2/1999 | Padia | |
| 6,140,064 A | 10/2000 | Loetscher et al. | |
| 6,545,005 B1 | 4/2003 | Baxter et al. | |
| 6,794,379 B2 | 9/2004 | Medina et al. | |
| 6,964,967 B2 | 11/2005 | Huang et al. | |
| 7,053,215 B2 | 5/2006 | Medina et al. | |
| 2003/0004358 A1 * | 1/2003 | Ulrich et al. | ............. 548/311.1 |
| 2005/0148602 A1 * | 7/2005 | Sircar et al. | ............. 514/259.1 |
| 2006/0036093 A1 * | 2/2006 | Lin et al. | ..................... 544/279 |
| 2006/0069099 A1 * | 3/2006 | Fu et al. | ........................ 514/251 |
| 2006/0069106 A1 * | 3/2006 | Fu et al. | ................... 514/260.1 |
| 2006/0069127 A1 | 3/2006 | Fu et al. | |
| 2007/0185139 A1 * | 8/2007 | Binnun et al. | ............ 514/260.1 |
| 2007/0197565 A1 * | 8/2007 | Kelly et al. | ............... 514/264.1 |
| 2007/0213533 A1 * | 9/2007 | Hiyoshi et al. | ............... 544/335 |
| 2007/0249609 A1 * | 10/2007 | Chen et al. | ................... 514/241 |
| 2007/0249631 A1 * | 10/2007 | Oberboersch et al. | ....... 514/257 |
| 2007/0249636 A1 * | 10/2007 | Aquila et al. | ............ 514/260.1 |
| 2007/0249637 A1 * | 10/2007 | Collins et al. | ............ 514/260.1 |
| 2007/0249659 A1 * | 10/2007 | Sakuraba et al. | ............ 514/300 |

FOREIGN PATENT DOCUMENTS

WO    WO 01/16114    3/2001

(Continued)

OTHER PUBLICATIONS

International Search Report PCT/US2006/025056, Nov. 7, 2006, Amgen Inc.

*Primary Examiner*—James O Wilson
*Assistant Examiner*—Cecilia M Jaisle
(74) *Attorney, Agent, or Firm*—Ronald S. Hermenau

(57) ABSTRACT

Provided herein are compounds of the formula

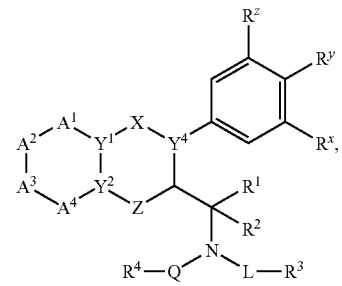

where $A^1$, $A^2$, $A^3$, $A^4$, L, Q, $R^1$, $R^2$, $R^3$, $R^4$, $R^x$, $R^y$, $R^z$, X, $Y^1$, $Y^2$, $Y^4$ and Z are as described herein, and compositions thereof that are useful in the treatment of inflammatory and immune conditions and diseases. In particular, the invention provides aryl nitrile compounds which modulate the expression and/or function of a chemokine receptor.

17 Claims, No Drawings

FOREIGN PATENT DOCUMENTS

| | | |
|---|---|---|
| WO | WO 01/19800 | 3/2001 |
| WO | WO 02/28839 | 4/2002 |
| WO | WO 02/083143 | 10/2002 |
| WO | WO 03/076418 | 9/2003 |
| WO | WO 2004/064741 | 8/2004 |
| WO | WO 2004/075863 | 9/2004 |
| WO | WO 2004/113335 | 12/2004 |
| WO | WO 2006/004915 | * 1/2006 |
| WO | WO 2006/004925 | * 1/2006 |
| WO | WO 2006/023381 | * 3/2006 |

* cited by examiner

ARYL NITRILE COMPOUNDS AND COMPOSITIONS AND THEIR USES IN TREATING INFLAMMATORY AND RELATED DISORDERS

This application claims priority under 35 U.S.C. §119(e) to U.S. Provisional Application No. 60/694,469, filed Jun. 27, 2005, the content of which is incorporated herein in its entirety.

1. FIELD OF THE INVENTION

The present invention relates to novel aryl nitrile modulators of the CXCR3 receptor, compositions comprising the novel compounds and methods of their use for the treatment of, for example, inflammatory and immunoregulatory disorders and diseases, including asthma and allergic diseases, as well as autoimmune pathologies such as rheumatoid arthritis, multiple sclerosis, inflammatory bowel disease, psoriasis and atherosclerosis.

2. BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165-183 (1991), Schall, et al., *Curr. Opin. Immunol.*, 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are four classes of chemokines, CXC($\alpha$), CC($\beta$), C($\gamma$), and $CX_3C(\delta)$, depending on whether the first two cysteines are separated by a single amino acid (C-X-C), are adjacent (C-C), have a missing cysteine pair (C), or are separated by three amino acids ($CXC_3$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381: 661-666 (1996)). The C chemokine lymphotactin shows specificity for lymphocytes (Kelner, et al., *Science*, 266: 1395-1399 (1994)) while the $CX_3C$ chemokine fractalkine shows specificity for lymphocytes and monocytes (Bazan, et al., *Nature*, 385:640-644 (1997).

Chemokines bind specific cell-surface receptors belonging to the family of G-protein-coupled seven-transmembrane-domain proteins (reviewed in Horuk, *Trends Pharm. Sci.*, 15:159-165 (1994)) termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to β-chemokines with the following characteristic pattern: CCR1 (or "CKR-1" or "CC-CKR-1") MIP-1α, MIP-1β, MCP-3, RANTES (Ben-Barruch, et al., *J. Biol. Chem.*, 270:22123-22128 (1995); Neote, et al., *Cell*, 72:415-425 (1993)); CCR2A and CCR2B (or "CKR-2A"/"CKR-2A" or "CC-CKR-2A"/"CC-CKR2A") MCP-1, MCP-3, MCP-4; CCR3 (or "CKR-3" or "CC-CKR-3") eotaxin, RANTES, MCP; (Ponath, et al., *J. Exp. Med.*, 183:2437-2448 (1996)); CCR4 (or "CKR-4" or "CC-CKR-4") TARC, MDC (Imai, et al., *J. Biol. Chem.*, 273:1764-1768 (1998)); CCR5 (or "CKR-5" or "CC-CKR-5") MIP-1α, RANTES, MIP-1β (Sanson, et al., *Biochemistry*, 35:3362-3367 (1996)); CCR6 MIP-3 alpha (Greaves, et al., *J. Exp. Med.*, 186:837-844 (1997)); CCR7 MIP-3 beta and 6Ckine (Campbell, et al., *J. Cell. Biol.*, 141:1053-1059(1998)); CCR8 I-309, HHV8 vMIP-I, HHV-8 vMIP-II, MCV vMCC-I (Dairaghi, et al., *J. Biol. Chem.*, 274:21569-21574 (1999)); CCR9 TECK (Zaballos, et al., *J. Immunol.*, 162:5671-5675 (1999)), D6 MIP-1 beta, RANTES, and MCP-3 (Nibbs, et al., *J. Biol. Chem.*, 272:32078-32083 (1997)), and the Duffy blood-group antigen RANTES, MCP-1 (Chaudhun, et al., *J. Biol. Chem.*, 269:7835-7838 (1994)).

Chemokine receptors, such as CCR1, CCR2, CCR2A, CCR2B, CCR3, CCR4, CCR5, CCR6, CCR7, CCR8, CCR9, CXCR1, CXCR2, CXCR3, CXCR4, CXCR5, CX3CR1, and XCR1 have been implicated as being important mediators of inflammatory and immunoregulatory disorders and diseases, including asthma and allergic diseases, as well as autoimmune pathologies such as rheumatoid arthritis and atherosclerosis.

The CXCR3 chemokine receptor is expressed primarily in T lymphocytes, and its functional activity can be measured by cytosolic calcium elevation or chemotaxis. The receptor was previously referred to as GPR9 or CKR-L2. Its chromosomal location is unusual among the chemokine receptors in being localized to Xq13. Ligands that have been identified that are selective and of high affinity are the CXC chemokines, IP10, MIG and ITAC.

The highly selective expression of CXCR3 makes it an ideal target for intervention to interrupt inappropriate T cell trafficking. The clinical indications for such intervention are in T-cell mediated autoimmune diseases such as multiple sclerosis, rheumatoid arthritis, and type I diabetes. Inappropriate T-cell infiltration also occurs in psoriasis and other pathogenic skin inflammation conditions, although the diseases may not be true autoimmune disorders. In this regard, up-regulation of IP-10 expression in keratinocytes is a common feature in cutaneous immunopathologies. Inhibition of CXCR3 can be beneficial in reducing rejection in organ transplantation. Ectopic expression of CXCR3 in certain tumors, especially subsets of B cell malignancies indicate that selective inhibitors of CXCR3 will have value in tumor immunotherapy, particularly attenuation of metastasis.

In view of the clinical importance of CXCR3, the identification of compounds that modulate CXCR3 function represents an attractive avenue into the development of new therapeutic agents. International Publication No. WO 02/083143, for example, describes CXCR3 antagonists. With the study of CXCR3 modulators, new developments and improvements been recognized leading to new compounds provided herein.

3. SUMMARY OF THE INVENTION

The present invention provides compounds that are useful, for example, in the treatment or prevention of certain inflammatory and immunoregulatory disorders and diseases, including asthma, psoriasis, inflammatory bowel disease and allergic diseases, as well as autoimmune pathologies such as rheumatoid arthritis and multiple sclerosis.

In one aspect, the compounds provided have the general formula I:

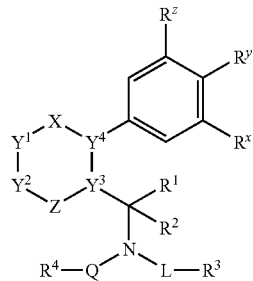

I wherein X is a member selected from the group consisting of a bond, —C(O)—, —C($R^5$)($R^6$)—, —C($R^5$)═, —S(O)—, —S(O)$_2$— and —N═; Z is a member selected from the group consisting of a bond, —N═, —O—, —S—, —C($R^7$)═ and —N($R^{14}$)—, with the proviso that X and Z are not both a bond; L is a member selected from the group consisting of a bond, C(O)—(C$_1$-C$_8$)alkylene, (C$_1$-C$_8$)alkylene and (C$_2$-C$_8$)heteroalkylene; Q is a member selected from the group consisting of (C$_1$-C$_8$)alkylene, —C(O)—, —OC(O)—, —N($R^8$)C(O)—, —CH$_2$CO—, —CH$_2$SO—, and —CH$_2$SO$_2$—, or optionally L and Q can be linked together to form a 5- or 6-membered heterocyclic group having from 1 to 3 heteroatoms. $R^1$ and $R^2$ are members independently a member selected from the group consisting of H, (C$_1$-C$_8$)alkyl, (C$_2$-C$_8$)heteroalkyl, aryl and heteroaryl, or optionally are combined to form a 3 to 8-membered ring having from 0 to 2 heteroatoms as ring vertices; optionally $R^2$ can be linked together with L to form a 5- or 6-membered heterocyclic group having from 1 to 4 heteroatoms. $R^3$ is absent or is a member selected from the group consisting of hydroxy, (C$_1$-C$_8$)alkoxy, amino, (C$_1$-C$_8$)alkylamino, di(C$_1$-C$_8$)alkylamino, (C$_1$-C$_{20}$)alkyl, (C$_2$-C$_8$)heteroalkyl, cyclo(C$_3$-C$_9$)heteroalkyl, (C$_1$-C$_8$)acylamino, amidino, guanidino, ureido, cyano, heteroaryl, —CONR$^9$R$^{10}$ and —CO$_2$R$^{11}$, or optionally, $R^3$ may be combined with $R^2$ to form a 4-, 5-, 6-, 7- or 8-membered ring containing from 1 to 3 heteroatoms selected from the group consisting of N, O and S. $R^4$ is a member selected from the group consisting of (C$_2$-C$_{20}$)alkyl, (C$_2$-C$_{20}$)heteroalkyl, heteroaryl, aryl, heteroaryl(C$_1$-C$_6$)alkyl, heteroaryl(C$_2$-C$_6$)heteroalkyl, aryl(C$_1$-C$_6$)alkyl and aryl(C$_2$-C$_6$)heteroalkyl. $R^5$ and $R^6$ are each members independently selected from the group consisting of H, (C$_1$-C$_8$)alkyl, (C$_2$-C$_8$)heteroalkyl, heteroaryl and aryl, or optionally $R^5$ and $R^6$ are combined to form a 3- to 7-membered ring. $R^7$ and $R^8$ are each members independently selected from the group consisting of H, (C$_1$-C$_8$)alkyl, (C$_2$-C$_8$)heteroalkyl, heteroaryl and aryl. Each $R^9$, $R^{10}$ and $R^{11}$ is independently selected from the group consisting of H, (C$_1$-C$_8$)alkyl, (C$_2$-C$_8$)heteroalkyl, heteroaryl, aryl, heteroaryl(C$_1$-C$_6$)alkyl, heteroaryl(C$_2$-C$_8$)heteroalkyl, aryl(C$_1$-C$_8$)alkyl and aryl(C$_2$-C$_8$)heteroalkyl. $R^x$, $R^y$ and $R^z$ are each independently H, F or cyano, wherein at least one of $R^x$, $R^y$ and $R^z$ is cyano.

Turning next to the ring vertices $Y^1$, $Y^2$, $Y^3$ and $Y^4$: $Y^1$ and $Y^2$ are each members independently selected from the group consisting of —C($R^{12}$)═, —CH($R^{12}$)—, —N═, —O—, —S—, and —N($R^{13}$)—. $Y^3$ is N or C, wherein when $Y^3$ is C, $Y^3$ shares a double bond with $Y^2$, $Y^4$ or Z. $Y^4$ is N or C, wherein when $Y^4$ is C, $Y^4$ shares a double bond with X, $Y^1$ or $Y^3$. Each $R^{12}$ is a member selected from the group consisting of H, halogen, hydroxy, amino, alkylamino, dialkylamino, (C$_1$-C$_8$)alkyl, cyclo(C$_3$-C$_6$)alkyl, (C$_2$-C$_8$)heteroalkyl, heteroaryl and aryl, or optionally, when $Y^1$ and $Y^2$ are each one of —C($R^{12}$)═ or —CH($R^{12}$)—, the two $R^{12}$ groups can be combined to form a substituted or unsubstituted 5- to 6-membered cycloalkyl, cycloheteroalkyl, aryl or heteroaryl ring. Optionally, when $Y^1$ is —C($R^{12}$)═ or —CH($R^{12}$)— and X is —C($R^5$)═ or —C($R^5$)($R^6$)—, $R^{12}$ and $R^5$ can be combined to form a substituted or unsubstituted 5- to 6-membered cycloalkyl, cycloheteroalkyl, aryl or heteroaryl ring. Each $R^{13}$ is a member selected from the group consisting of H, (C$_1$-C$_8$)alkyl, (C$_2$-C$_8$)heteroalkyl, heteroaryl, aryl, heteroaryl(C$_1$-C$_6$)alkyl, cyclo(C$_3$-C$_6$)alkyl, heteroaryl(C$_2$-C$_8$)heteroalkyl, aryl(C$_1$-C$_8$)alkyl and aryl(C$_2$-C$_8$)heteroalkyl. Optionally, when one of $Y^1$ and $Y^2$ is —C($R^{12}$)═ or —CH($R^{12}$)— and the other is —N($R^{13}$)—, $R^{12}$ and $R^{13}$ can be combined to form a substituted or unsubstituted 5- to 6-membered cycloalkyl, cycloheteroalkyl, aryl or heteroaryl ring, or optionally, when $Y^1$ and $Y^2$ are both —N($R^{13}$)— the two $R^{13}$ groups can be combined to form a substituted or unsubstituted 5- to 6-membered cycloalkyl, cycloheteroalkyl, aryl or heteroaryl ring. $R^{14}$ is a member selected from the group consisting of H, (C$_1$-C$_8$)alkyl, (C$_2$-C$_8$)heteroalkyl, cyclo(C$_3$-C$_6$)alkyl, heteroaryl, aryl, heteroaryl(C$_1$-C$_6$)alkyl, heteroaryl(C$_2$-C$_8$)heteroalkyl, aryl(C$_1$-C$_8$)alkyl and aryl(C$_2$-C$_8$)heteroalkyl; or, optionally, when $Y^2$ is —C($R^{12}$)═, —CH($R^{12}$)— or —N($R^{13}$)—, $R^{14}$ or $R^7$ can be combined with $R^{12}$ or $R^{13}$ to form a substituted or unsubstituted 5- to 6-membered cycloalkyl, cycloheteroalkyl, aryl or heteroaryl ring.

As will be clear to those of skill in the art, the ring comprising X, $Y^1$, $Y^2$, $Y^3$, $Y^4$ and Z can be aromatic.

Unless otherwise indicated, the compounds provided in the above formula are meant to include pharmaceutically acceptable salts, solvates, prodrugs or isomers thereof.

In another aspect, the present invention provides compounds having formula II:

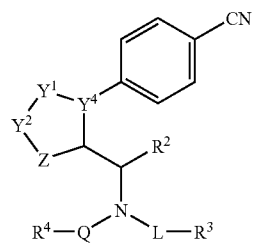

II wherein L, Q, $R^2$, $R^3$, $R^4$, $Y^4$ and Z are as described above in formula I; and $Y^1$ and $Y^2$ are each members independently selected from the group consisting of —C($R^{12}$)═, —N═, —O—, —S—, and —N($R^{13}$)—, wherein each $R^{12}$ is a member independently selected from the group consisting of H, halogen, hydroxy, amino, alkylamino, dialkylamino, (C$_1$-C$_8$)alkyl, cyclo(C$_3$-C$_6$)alkyl, (C$_2$-C$_8$)heteroalkyl, heteroaryl and aryl, and each $R^{13}$ is a member selected from the group consisting of H, (C$_1$-C$_8$)alkyl, cyclo(C$_3$-C$_6$)alkyl, (C$_2$-C$_8$)heteroalkyl, heteroaryl, aryl, heteroaryl(C$_1$-C$_6$)alkyl, heteroaryl(C$_2$-C$_8$)heteroalkyl, aryl(C$_1$-C$_8$)alkyl and aryl(C$_2$-C$_8$)heteroalkyl.

As will be clear to those of skill in the art, the ring comprising $Y^1$, $Y^2$, $Y^4$ and Z can be aromatic.

In another aspect, the compounds provided have the formula III:

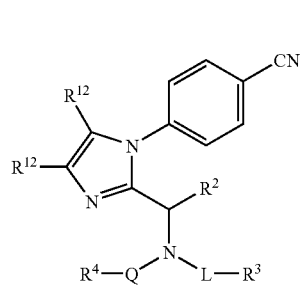

III wherein L, Q, $R^2$, $R^3$, $R^4$, and each $R^{12}$ are as described above in formula II.

In another aspect, the compounds provided have the formula IV:

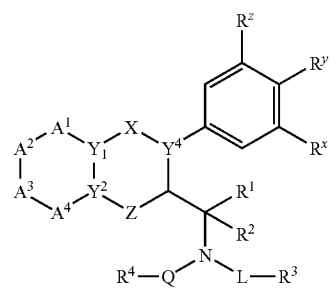

IV wherein L, Q, $R^1$, $R^2$, $R^3$, $R^4$, $R^x$, $R^y$, $R^z$, X and $Y^4$ are as described above in formula I; Z is —N= or —CH=; $Y^1$ is N or C wherein when $Y^1$ is C, Y, shares a double bond with $A^1$, $Y^2$, X, or $Y^4$; $Y^2$ is C wherein the carbon atom shares a double bond with $A^4$, $Y^1$ or Z; $A^1$, $A^3$, and $A^4$ are each independently —N=, —N($R^{15}$)—, —S—, =C($R^{16}$)—, —C($R^{16}$)($R^{17}$)—, —C(O)— or —O—; $A^2$ is a bond, —N=, —N($R^{15}$)—, =C($R^{16}$)—, —C($R^{16}$)($R^{17}$)— or —C(O)—; and each $R^{15}$, $R^{16}$ and $R^{17}$ is a member independently selected from the group consisting of H, halogen, ($C_1$-$C_8$)alkyl, ($C_2$-$C_8$)heteroalkyl, fluoro($C_1$-$C_4$)alkyl, aryl, heteroaryl, aryl($C_1$-$C_8$)alkyl, heteroaryl($C_1$-$C_8$)alkyl, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NHC($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, wherein R', R" and R'" are each independently selected from H, ($C_1$-$C_8$)alkyl, ($C_2$-$C_8$)heteroalkyl, unsubstituted aryl, unsubstituted heteroaryl, (unsubstituted aryl)-($C_1$-$C_4$)alkyl, and (unsubstituted aryl)oxy-($C_1$-$C_4$)alkyl.

As will be clear to those of skill in the art, either the ring comprising $A^1$, $A^2$, $A^3$, $A^4$, $Y^1$ and $Y^2$, or the ring comprising X, $Y^1$, $Y^2$, $Y^3$, $Y^4$ and Z, or both rings, can be aromatic.

In another aspect, the compounds provided have the formula V:

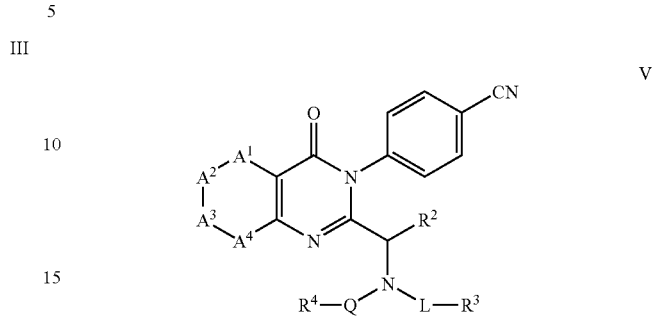

V wherein L, Q, $R^2$, $R^3$ and $R^4$ are as described above in formula IV; $A^1$, $A^2$ and $A^3$ are each independently —C($R^{16}$)($R^{17}$)— or —C(O)—; $A^4$ is —N($R^{15}$)—, or —C($R^{16}$)($R^{17}$)—, and each $R^{15}$, $R^{16}$ and $R^{17}$ is independently H, halogen, ($C_1$-$C_8$)alkyl, ($C_2$-$C_8$)heteroalkyl, fluoro($C_1$-$C_4$)alkyl, aryl, heteroaryl, aryl($C_1$-$C_8$)alkyl or heteroaryl($C_1$-$C_8$)alkyl.

In another aspect, the compounds provided have the formula VI:

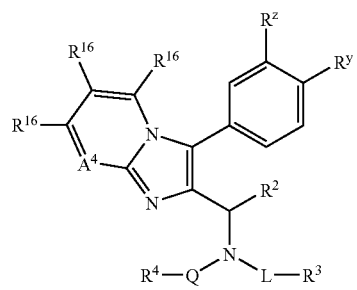

VI wherein L, Q, $R^2$, $R^3$, $R^4$, $R^x$, $R^y$, $R^z$ and $A^4$ are as described above in formula IV.

In another aspect, the compounds provided have the formula VII:

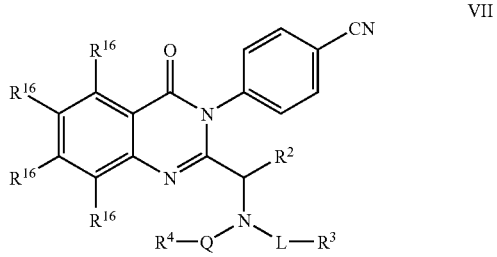

VII wherein L, Q, $R^2$, $R^3$, $R^4$ and $R^{16}$ are as described above in formula IV.

In another aspect, the compounds provided have the formula VIII:

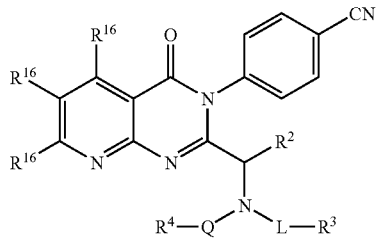

wherein L, Q, $R^2$, $R^3$, $R^4$ and $R^{16}$ are as described above in formula IV.

In another aspect, the compounds provided have the formula IX:

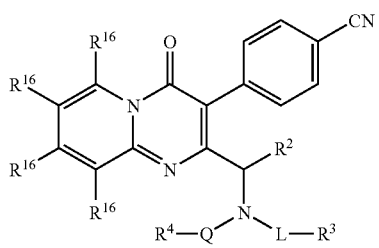

wherein L, Q, $R^2$, $R^3$, $R^4$ and $R^{16}$ are as described above in formula IV.

The present invention also provides pharmaceutical compositions comprising a compound of formula I-IX and a pharmaceutically acceptable excipient or carrier.

The present invention further provides methods for the treatment of an inflammatory or immune condition or disorder, comprising administering to a subject in need of such treatment a therapeutically effective amount of a compound of formula I-IX.

The present invention also provides methods for the treatment of a condition or disorder mediated by the CXCR3 chemokine receptor, comprising administering to a subject in need of such treatment a therapeutically effective amount of a compound of formula I-IX.

The present invention also provides methods for the modulation of CXCR3, comprising contacting a cell with a compound of formula I-IX.

The present invention further provides methods for the modulation of CXCR3, comprising contacting a CXCR3 protein with a compound of formula I.

4. DETAILED DESCRIPTION OF THE INVENTION

4.1. Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quarternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, and —CH═CH—N($CH_3$)—$CH_3$. Up to two heteroatoms may be consecutive, such as, for example, —$CH_2$—NH—$OCH_3$ and —$CH_2$—O—Si($CH_3$)$_3$. When a prefix such as ($C_2$-$C_8$) is used to refer to a heteroalkyl group, the number of carbons (2-8, in this example) is meant to include the heteroatoms as well. For example, a $C_2$-heteroalkyl group is meant to include, for example, —$CH_2$OH (one carbon atom and one heteroatom replacing a carbon atom) and —$CH_2$SH. The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "cycloheteroalkyl", by themselves or in combination with other terms, represent, unless otherwise stated, cyclic versions of "alkyl" and "heteroalkyl", respectively. Additionally, for cycloheteroalkyl, a heteroatom can occupy the position at which the cycloheteroalkyl is attached to the remainder of the molecule. Examples of cycloalkyl include cyclopentyl, cyclohexyl, 1-cyclohexenyl, 3-cyclohexenyl, cycloheptyl, and the like. Examples of cycloheteroalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quarternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, cycloheteroalkyl, cycloalkenyl, and cycloheteroalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to H, unsubstituted ($C_1$-$C_8$) alkyl and heteroalkyl, unsubstituted aryl, aryl substituted with 1-3 halogens, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O) CH$_2$OCH$_3$, and the like). Preferably, the alkyl groups will have from 0-3 substituents, more preferably 0, 1, or 2 substituents, unless otherwise specified.

Similarly, substituents for the aryl and heteroaryl groups are varied and are selected from: -halogen, —OR', —OC(O) R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$) =NH, —NR'C(NH$_2$)=NH, —NH—C(NH$_2$)=NR', —S(O) R', —S(O)$_2$R', —S(O)$_2$NR'R", —N$_3$, —CH(Ph)$_2$, perfluoro ($C_1$-$C_4$)alkoxy, and perfluoro($C_1$-$C_4$)alkyl, in a number ranging from zero to the total number of open valences on the aromatic ring system; and where R', R" and R'" are independently selected from H, ($C_1$-$C_8$)alkyl and heteroalkyl, unsubstituted aryl and heteroaryl, (unsubstituted aryl)-($C_1$-$C_4$) alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "heteroatom" is meant to include oxygen (O), nitrogen (N), sulfur (S) and silicon (Si). In certain embodiments, the term "heteroatom" indicates O, N or S.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, et al. (1977) *J. Pharm. Sci.* 66: 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention may exist in multiple crystalline or amorphous forms. In general, all physical forms are intended to be within the scope of the present invention. In certain embodiments, a compound of the present invention is in a crystalline form. In some embodiments, a compound of the present invention is in an amorphous form. In some embodiments, the purity a compound of the present invention in a solid form is at least 80% pure, at least 85% pure, at least 90% pure, at least 92% pure, at least 95% pure, at least 97% pure, or at least 98% pure.

Certain compounds of the present invention possess asymmetric carbon atoms (optical centers) or double bonds; the racemates, enantiomers, diastereomers, geometric isomers and individual isomers are all intended to be encompassed within the scope of the present invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. It should be noted that if the stereochemistry of a structure or a portion of a structure is not indicated with, for example, bold or dashed lines, the structure or portion of the structure is to be interpreted as encompassing all stereoisomers of it.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of the compounds of the present invention, whether radioactive or not, are intended to be encompassed within the scope of the present invention.

As used herein, the term "active" means effective to modulate, e.g., inhibit, CXCR3 function.

The terms "treat", "treating" or "treatment", as used herein, refer to a method of alleviating or abrogating a disease and/or its attendant symptoms. The terms "prevent", "preventing" or "prevention", as used herein, refer to a method of barring a subject from acquiring a disease.

4.2. Embodiments of the Invention

The present invention is directed to compounds, compositions and methods useful in the modulation of chemokine receptor activity, particularly CXCR3. The compounds of the invention are useful for the treatment of, for example, inflammatory and immunoregulatory disorders, and can be administered directly to subjects, for example, humans, as formulated pharmaceuticals. The compounds of the invention are also useful for identifying and/or designing compounds that modulate CXCR3 function, e.g., CXCR3 antagonists, and compounds that are converted to one or more compounds that modulate CXCR3 function under physiological conditions.

The compounds of the present invention are those which inhibit at least one function or characteristic of a mammalian CXCR3 protein, for example, a human CXCR3 protein. The ability of a compound to inhibit such a function can be demonstrated in a binding assay (e.g., ligand binding or agonist binding), a signaling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes). Exemplary assays are described in U.S. Patent Application Publication No. 2003/0055054 A1 and International Publication No. WO 02/083143, the contents of which are each hereby incorporated by reference in their entirety.

4.3. Compounds

The present invention provides compounds that are useful as antagonists of CXCR3, having particular utility for the treatment of inflammation. The compounds provided herein have the general formula I:

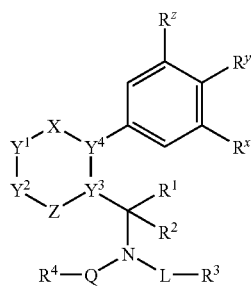

wherein L, Q, $R^1$, $R^2$, $R^3$, $R^4$, $R^x$, $R^y$, $R^z$, X, $Y^1$, $Y^2$, $Y^3$, $Y^4$ and Z are as defined below.

X is a bond, —C(O)—, —C($R^5$)($R^6$)—, —C($R^5$)=, —S(O)—, —S(O)$_2$— or —N=.

Z is a bond, —N=, —O—, —S—, —C($R^7$)= or —N($R^{14}$)—, with the proviso that X and Z are not both a bond.

L is a bond, C(O)—($C_1$-$C_8$)alkylene, ($C_1$-$C_8$)alkylene or ($C_2$-$C_8$)heteroalkylene.

Q is ($C_1$-$C_8$)alkylene, —C(O)—, —OC(O)—, —N($R^8$)C(O)—, —CH$_2$CO—, —CH$_2$SO—, or —CH$_2$SO$_2$—. Optionally L and Q can be linked together to form a 5- or 6-membered heterocyclic group having from 1 to 3 heteroatoms.

$R^1$ and $R^2$ are members independently a member selected from the group consisting of H, ($C_1$-$C_8$)alkyl, ($C_2$-$C_8$)heteroalkyl, aryl and heteroaryl, or optionally are combined to form a 3 to 8-membered ring having from 0 to 2 heteroatoms as ring vertices.

Optionally $R^2$ can be linked together with L to form a 5- or 6-membered heterocyclic group having from 1 to 4 heteroatoms.

In certain embodiments, $R^1$ is H, and $R^2$ is a member selected from the group consisting of —CH$_3$, —CH$_2$CH$_3$, —CH$_2$CH$_2$NH$_2$

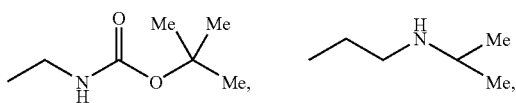

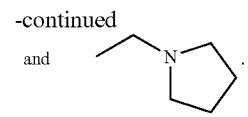

$R^3$ is absent or is a member selected from the group consisting of hydrogen, hydroxy, ($C_1$-$C_8$)alkoxy, amino, ($C_1$-$C_8$) alkylamino, di($C_1$-$C_8$)alkylamino, ($C_1$-$C_{20}$)alkyl, ($C_2$-$C_8$) heteroalkyl, cyclo($C_3$-$C_9$)heteroalkyl, ($C_1$-$C_8$)acylamino, amidino, guanidino, ureido, cyano, heteroaryl, —CONR$^9$R$^{10}$ and —CO$_2$R$^{11}$. Optionally, $R^3$ may be combined with $R^2$ to form a 4-, 5-, 6-, 7- or 8-membered ring containing from 1 to 3 heteroatoms selected from the group consisting of N, O and S.

In certain preferred embodiments, $R^3$ is ($C_2$-$C_8$)heteroalkyl or cyclo($C_3$-$C_9$)heteroalkyl containing a thioether, sulfoxide, or sulfone.

In some embodiments, $R^3$ is a member selected from the group consisting of —CHR$^{21}$R$^{22}$, —S(O)$_m$R$^{23}$, —S(O)$_m$N(R$^{24}$)R$^{25}$, —S(O)$_m$N(R$^{24}$)CH$_2$R$^{26}$, —N(R$^{24}$)SO$_2$R$^{23}$, N(R$^{24}$)CH$_2$R$^{26}$,

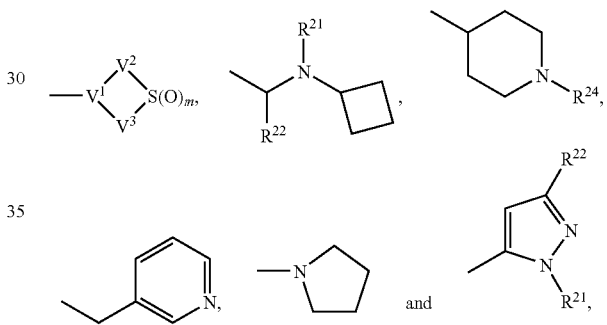

where the subscript m is 0, 1 or 2, and groups $R^{21}$, $R^{22}$, $R^{23}$, $R^{24}$, $R^{25}$, $R^{26}$, $V^1$, $V^2$, $V^3$ and $V^4$ are defined below.

In some embodiments, $R^3$ is a member selected from the group consisting of —SO$_2$CH$_3$, —SO$_2$CH$_2$CH$_3$, —CH(CH$_3$) CH$_3$,

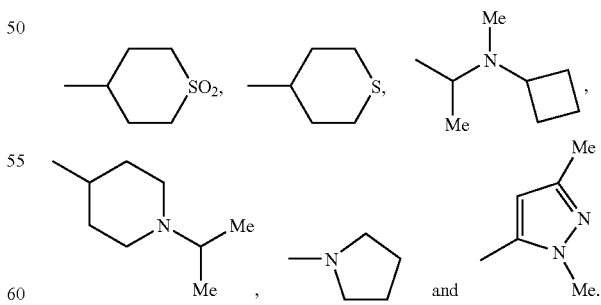

$R^4$ is ($C_2$-$C_{20}$)alkyl, ($C_2$-$C_{20}$)heteroalkyl, heteroaryl, aryl, heteroaryl($C_1$-$C_6$)alkyl, heteroaryl($C_2$-$C_6$)heteroalkyl, aryl ($C_1$-$C_6$)alkyl or aryl($C_2$-$C_6$)heteroalkyl.

In certain embodiments, Q is —CH$_2$CO—, and $R^4$ is aryl or heteroaryl.

In some embodiments, Q-R⁴ taken together is

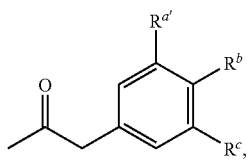

where $R^a$, $R^b$ and $R^c$ are each independently —H, halogen, —CN, —OCF$_3$, or —CF$_3$. In some embodiments, $R^a$ and $R^b$ are each independently halogen, —OCF$_3$, or —CF$_3$, and $R^c$ is —H. In some embodiments, $R^a$ is —CF$_3$, $R^b$ is —F and $R^c$ is —H.

$R^5$ and $R^6$ are each independently H, (C$_1$-C$_8$)alkyl, (C$_2$-C$_8$) heteroalkyl, heteroaryl or aryl, or optionally $R^5$ and $R^6$ are combined to form a 3- to 7-membered ring.

$R^7$ and $R^8$ are each members independently selected from the group consisting of H, (C$_1$-C$_8$)alkyl, (C$_2$-C$_8$)heteroalkyl, heteroaryl and aryl.

$R^9$, $R^{10}$ and $R^{11}$ are each independently selected from the group consisting of H, (C$_1$-C$_8$)alkyl, (C$_2$-C$_8$)heteroalkyl, heteroaryl, aryl, heteroaryl(C$_1$-C$_6$)alkyl, heteroaryl(C$_2$-C$_8$)heteroalkyl, aryl(C$_1$-C$_8$)alkyl and aryl(C$_2$-C$_8$)heteroalkyl.

$R^{21}$ and $R^{22}$ independently are hydrogen, (C$_1$-C$_8$)alkyl or (C$_2$-C$_8$)heteroalkyl.

$R^{23}$ is selected from the group consisting of (C$_1$-C$_8$)alkyl, (C$_2$-C$_8$)heteroalkyl, aryl and heteroaryl.

$R^{24}$ is hydrogen, (C$_1$-C$_8$)alkyl, (C$_2$-C$_8$)heteroalkyl, heteroaryl or aryl.

$R^{25}$ is (C$_1$-C$_8$)alkyl.

$R^{26}$ is aryl.

$V^1$ is CH or N.

$V^2$ is a bond, (C$_1$-C$_6$)alkylene or (C$_1$-C$_6$)heteroalkylene.

$V^3$ is (C$_1$-C$_6$)alkylene.

$R^x$, $R^y$ and $R^z$ are each independently H, F or cyano, wherein at least one of $R^x$, $R^y$ and $R^z$ is cyano.

In certain embodiments, $R^z$ and $R^x$ are H.

In certain embodiments, $R^1$, $R^z$ and $R^x$ are H, L is methylene or ethylene, Q is —CH$_2$CO—, and $R^4$ is aryl or heteroaryl.

$Y^1$ and $Y^2$ are each independently —C(R$^{12}$)=, —CH (R$^{12}$)—, —N=, —O—, —S—, or —N(R$^{13}$)—.

$Y^3$ is N or C, wherein when $Y^3$ is C, $Y^3$ shares a double bond with $Y^2$, $Y^4$ or Z.

$Y^4$ is N or C, wherein when $Y^4$ is C, $Y^4$ shares a double bond with X, $Y^1$ or $Y^3$.

$R^{12}$ is H, halogen, hydroxy, amino, alkylamino, dialkylamino, (C$_1$-C$_8$)alkyl, cyclo(C$_3$-C$_6$)alkyl, (C$_2$-C$_8$)heteroalkyl, heteroaryl or aryl.

Optionally, when $Y^1$ and $Y^2$ are each one of —C(R$^{12}$)= or —CH(R$^{12}$)—, the two R$^{12}$ groups can be combined to form a substituted or unsubstituted 5- to 6-membered cycloalkyl, cycloheteroalkyl, aryl or heteroaryl ring.

Optionally, when $Y^1$ is —C(R$^{12}$)= or —CH(R$^{12}$)— and X is —C(R$^5$)= or —C(R$^5$)(R$^6$)—, R$^{12}$ and R$^5$ can be combined to form a substituted or unsubstituted 5- to 6-membered cycloalkyl, cycloheteroalkyl, aryl or heteroaryl ring.

$R^{13}$ is H, (C$_1$-C$_8$)alkyl, (C$_2$-C$_8$)heteroalkyl, heteroaryl, aryl, heteroaryl(C$_1$-C$_6$)alkyl, cyclo(C$_3$-C$_6$)alkyl, heteroaryl (C$_2$-C$_8$)heteroalkyl, aryl(C$_1$-C$_8$)alkyl or aryl(C$_2$-C$_8$)heteroalkyl.

Optionally, when one of $Y^1$ and $Y^2$ is —C(R$^{12}$)= or —CH (R$^{12}$)— and the other is —N(R$^{13}$)—, R$^{12}$ and R$^{13}$ can be combined to form a substituted or unsubstituted 5- to 6-membered cycloalkyl, cycloheteroalkyl, aryl or heteroaryl ring.

Optionally when $Y^1$ and $Y^2$ are both —N(R$^{13}$)— the two R$^{13}$ groups can be combined to form a substituted or unsubstituted 5- to 6-membered cycloalkyl, cycloheteroalkyl, aryl or heteroaryl ring.

$R^{14}$ is a member selected from the group consisting of H, (C$_1$-C$_8$)alkyl, (C$_2$-C$_8$)heteroalkyl, cyclo(C$_3$-C$_6$)alkyl, heteroaryl, aryl, heteroaryl(C$_1$-C$_6$)alkyl, heteroaryl(C$_2$-C$_8$)heteroalkyl, aryl(C$_1$-C$_8$)alkyl and aryl(C$_2$-C$_8$)heteroalkyl, wherein optionally, when $Y^2$ is —C(R$^{12}$)=, —CH(R$^{12}$)— or —N(R$^{13}$)—, R$^{14}$ or R$^7$ can be combined with R$^{12}$ or R$^{13}$ to form a substituted or unsubstituted 5- to 6-membered cycloalkyl, cycloheteroalkyl, aryl or heteroaryl ring.

In certain embodiments, X, $Y^1$, $Y^2$, $Y^3$, Y and Z taken together form a 5- or 6-membered aromatic ring.

Embodiments represented by the above formula can be appreciated by replacing the ring system having vertices X, Z, $Y^1$, $Y^2$, $Y^3$ and $Y^4$ with an appropriate scaffold wherein the attachment points represent the attachment of para-substituted and/or meta-substituted cyanophenyl and the carbon atom that bears the R$^1$ and R$^2$ groups:

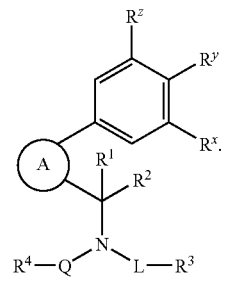

For example, the ring system or "scaffold" is meant to include the following (including substituted versions thereof) wherein the "A" ring is selected from those embodiments shown as:

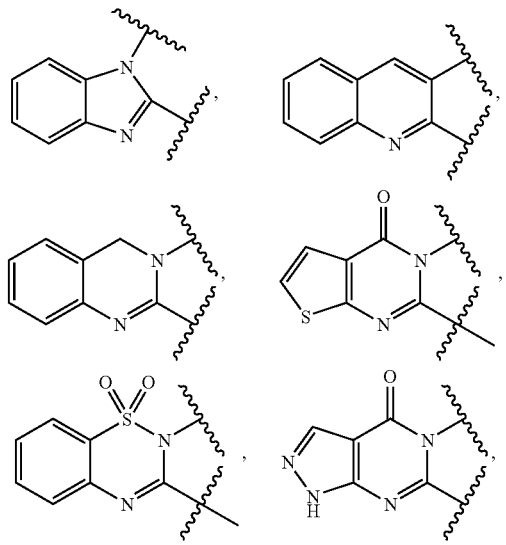

-continued

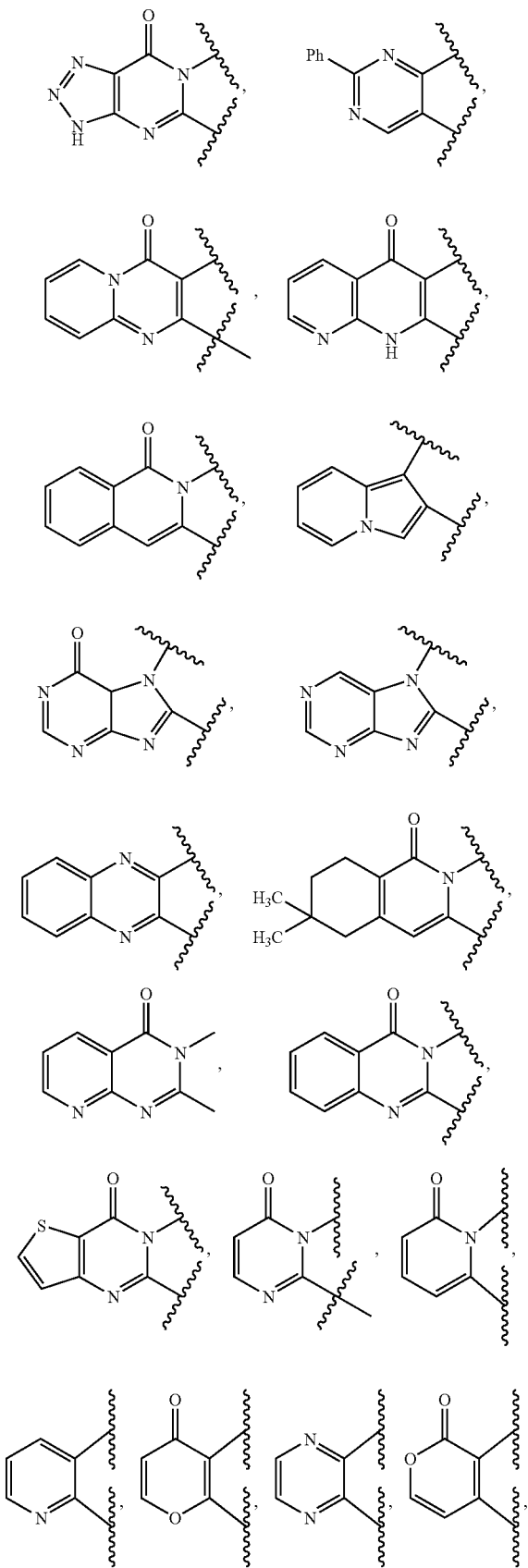

Still other A ring scaffolds are six-membered rings (without additional fused rings) and include:

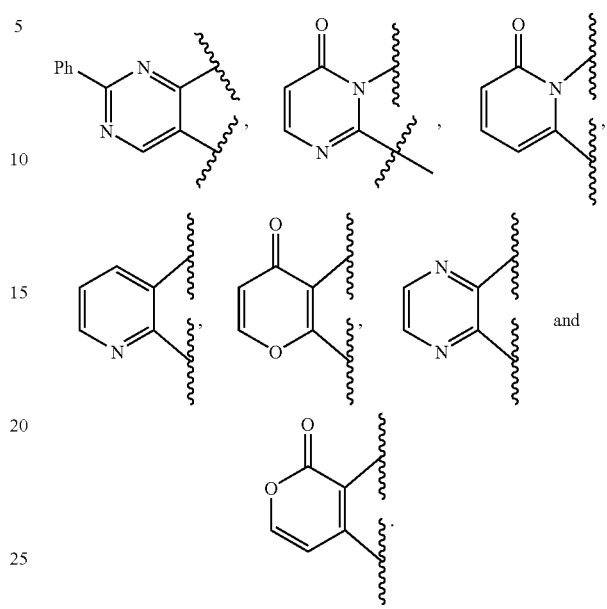

In other embodiments, the A ring scaffolds are five-membered rings (without additional fused rings) and include, for example:

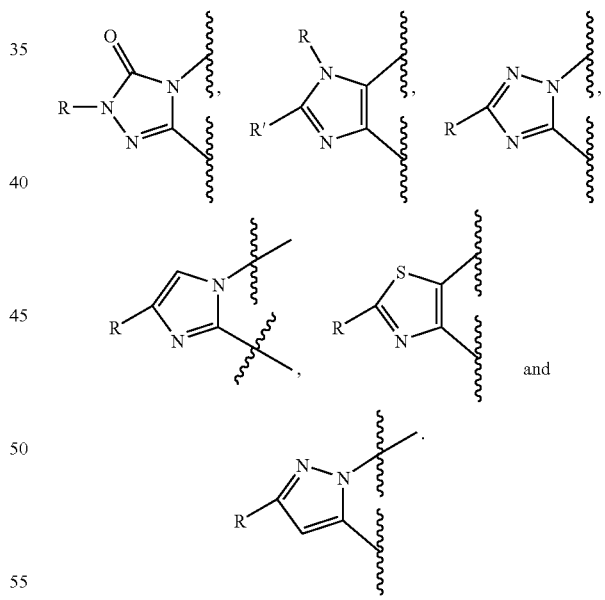

Typically, the ring substituents (shown as R and R' groups in the above five-membered rings, but not shown in the fused ring sets or six-membered rings above) are designed to provide electronic and/or additional hydrophobic or hydrophilic character to the molecule to bring the overall physical characters into conformity with those of the most preferred compounds 6,6-bicyclic fused rings in the series.

Within each of the above groups of embodiments, preferred embodiments are those in which $R^y$ is cyano, and $R^x$ and $R^z$ are hydrogen. Without intending to be limited by any particular theory or mechanism, it is believed, as demonstrated, for example, in Section 5.15 below, that para-cyanophenyl containing structures show improved resistance to metabolization under physiological conditions as compared to, for example, para-alkoxyphenyl containing structures. Moreover, compounds of the present invention appear to avoid time-dependent cytochrome P450 3A ("CYP") inhibition, a desirable feature in a CXCR3 antagonist.

Returning to formula I, in one group of preferred embodiments, X is —C(O)—. In another group, Z is —N=. In still another group of preferred embodiments, $Y^1$ is —C($R^{12}$)= or —N($R^{13}$)— and $Y^2$ is —C($R^{12}$)=, wherein the two $R^{12}$ groups, or the $R^{13}$ and $R^{12}$ groups, are combined to form a fused 6-membered aryl or heteroaryl ring. Particularly preferred, are those embodiments that combine each of these preferred groups. Accordingly, in one group of particularly preferred embodiments, X is —C(O)—; Z is —N=; $Y^3$ is C; and $Y^1$ and $Y^2$ are each —C($R^{12}$)= wherein the two $R^{12}$ groups are combined to form a fused 6-membered substituted or unsubstituted aryl or heteroaryl ring. In another group of particularly preferred embodiments, X is —C(O)—; Z is —N=; $Y^3$ is C; $Y^1$ is —N($R^{13}$)—, and $Y^2$ is —C($R^{12}$)= wherein the $R^{13}$ and $R^{12}$ groups are combined to form a fused 6-membered substituted or unsubstituted aryl or heteroaryl ring.

In some preferred embodiments, L is methylene or ethylene; Q is —CH$_2$C(O)—, $R^4$ is aryl or heteroaryl, preferably substituted phenyl; $R^3$ is (C$_2$-C$_8$)heteroalkyl or cyclo(C$_3$-C$_9$) heteroalkyl containing a thioether, sulfoxide, or sulfone; $R^1$ is H; $R^2$ is (C$_1$-C$_4$)alkyl; $Y^3$ is C; and the $Y^3$-containing ring system is selected from quinoline, quinazoline, imidazole, pyrido[2,3-d]pyrimidin-4-one, pyrido[1,2-a]pyrimidin-4-one, 7-fluoropyrido[1,2-a]pyrimidin-4-one, quinolinone, quinazolinone, triazolinone, pyrimidin-4-one, benzimidazole, thiazole, imidazole, pyridine, pyrazine and benzodiazepine.

In another group of embodiments, X is a bond; $Y^4$ is N; $Y^3$ is C; Z is —N=; and $Y^1$ and $Y^2$ are each —C($R^{12}$)=. In another group of embodiments, X is —C($R^5$)=; $Y^4$ is C; $Y^3$ is C; Z is —C($R^7$)=; and $Y^1$ and $Y^2$ are each —C($R^{12}$)=. In another group of embodiments, X is a bond; Z is —N=; $Y^4$ is C; $Y^1$ is selected from the group consisting of —O—, —S— and —N($R^{13}$)—; and $Y^2$ is —C($R^{12}$)=.

In each of the above groups of preferred embodiments, $R^1$ is most preferably H.

It will be understood that, in certain embodiments, the compound of formula I is not 2-Biphenyl-4-yl-N-{1-[3-(4-cyanophenyl)-4-oxo-3,4-dihydro-quinazolin-2-yl]-ethyl}-N-(2-methoxy-ethyl)-acetamide; 2-Biphenyl-4-yl-N-{1-[3-(4-cyanophenyl)-4-oxo-3,4-dihydro-quinazolin-2-yl]-ethyl}-N-(2-ethoxy-ethyl)-acetamide; 2-Biphenyl-4-yl-N-{1-[3-(4-cyanophenyl)-5-methyl-4-oxo-3,4-dihydro-quinazolin-2-yl]-propyl}-N-(2-ethoxy-ethyl)-acetamide; 2-((N-2-Ethoxyethyl)-N-(4-trifluoromethylphenylacetyl)-1-aminoethyl)-3-(4-cyanophenyl)-3H-quinazoline-4-one; N-{1R-[3-(4-cyanophenyl)-4-oxo-3,4-dihydro-pyrido[2,3-d]pyrimidin-2-yl]-ethyl}-N-(1H-imidazol-2-ylmethyl)-2-(4-trifluoromethyl-phenyl)-acetamide; N-{1R-[3-(4-cyanophenyl)-4-oxo-3,4-dihydro-pyrido[2,3-d]pyrimidin-2-yl]-ethyl}-N-pyridin-3-ylmethyl-2-(4-trifluoromethyl-phenyl)-acetamide; N-{1R-[3-(4-cyanophenyl)-4-oxo-3,4-dihydro-pyrido[2,3-d]pyrimidin-2-yl]-ethyl}-N-(1-methyl-1H-imidazol-2-ylmethyl)-2-(4-trifluoromethyl-phenyl)-acetamide; N-{1-[3-(4-cyanophenyl)-4-oxo-3,4-dihydro-quinazolin-2-yl]-ethyl}-2-(3-fluoro-4-trifluoromethyl-phenyl)-N-pyridin-3-ylmethyl-acetamide; or (R)-N-{1-[3-(4-cyanophenyl)-4-oxo-3,4-dihydro-pyrido[2,3-d] pyrimidin-2-yl]-ethyl}-2-(4-fluoro-3-trifluoromethyl-phenyl)-N-pyridin-3-ylmethyl-acetamide.

In some embodiments, the present invention provides a compound having formula II:

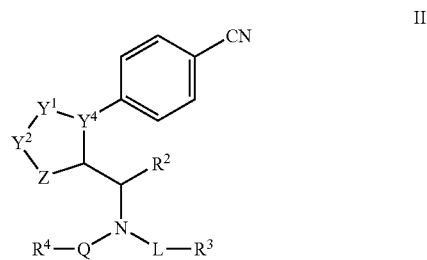

wherein L, Q, $R^2$, $R^3$, $R^4$, $Y^4$ and Z are as described above in formula I; and $Y^1$ and $Y^2$ are as described below.

$Y^1$ and $Y^2$ are each members independently selected from the group consisting of —C($R^{12}$)=, —N=, —O—, —S—, or —N($R^{13}$)—, wherein each $R^{12}$ is H, halogen, hydroxy, amino, alkylamino, dialkylamino, (C$_1$-C$_8$)alkyl, cyclo(C$_3$-C$_6$)alkyl, (C$_2$-C$_8$)heteroalkyl, heteroaryl or aryl, and each $R^{13}$ is H, (C$_1$-C$_8$)alkyl, cyclo(C$_3$-C$_6$)alkyl, (C$_2$-C$_8$)heteroalkyl, heteroaryl, aryl, heteroaryl(C$_1$-C$_6$)alkyl, heteroaryl(C$_2$-C$_8$) heteroalkyl, aryl(C$_1$-C$_8$)alkyl or aryl(C$_2$-C$_8$)heteroalkyl.

In certain embodiments, the ring comprising $Y^1$, $Y^2$, $Y^4$ and Z can be aromatic.

In certain embodiments of formula II, $R^3$ is (C$_2$-C$_8$)heteroalkyl or cyclo(C$_3$-C$_9$)heteroalkyl containing a thioether, sulfoxide, or sulfone, L is methylene or ethylene, Q is CH$_2$CO—, and $R^4$ is a substituted aryl or substituted heteroaryl.

In some embodiments, Q-$R^4$ taken together is

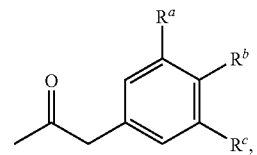

where $R^a$, $R^b$ and $R^c$ are each independently —H, halogen, —CN, —OCF$_3$, or —CF$_3$. In some embodiments, $R^a$ and $R^b$ are each independently halogen, —OCF$_3$, or —CF$_3$, and $R^c$ is —H. In some embodiments, $R^a$ is —CF$_3$, $R^b$ is —F and $R^c$ is —H.

In certain embodiments, a compound of the present invention has formula III:

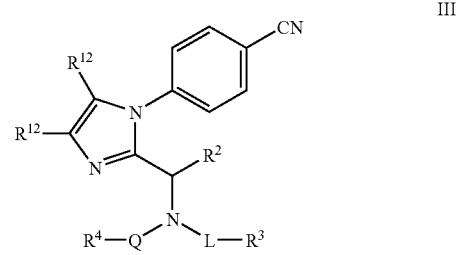

wherein L, Q, $R^2$, $R^3$, $R^4$, and each $R^{12}$ are as described above in formula II.

In some embodiments, the present invention provides a compound having formula IV:

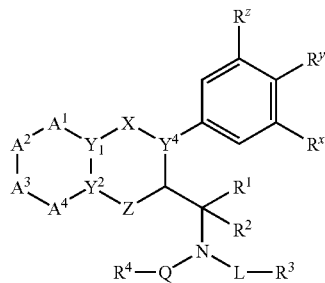

wherein L, Q, $R^1$, $R^2$, $R^3$, $R^4$, $R^x$, $R^y$, $R^z$, X and $Y^4$ are as described above in formula I, and Z, $Y^1$, $Y^2$, $A^1$, $A^2$, $A^3$, $A^4$ are described below.

Z is —N═ or —CH═.

$Y^1$ is N or C wherein when $Y^1$ is C, $Y^1$ shares a double bond with $A^1$, $Y^2$, X, or $Y^4$.

$Y^2$ is C wherein the carbon atom shares a double bond with $A^4$, $Y^1$ or Z.

$A^1$, $A^3$, and $A^4$ are each independently —N═, —N($R^{15}$)—, —S—, ═C($R^{16}$)—, —C($R^{16}$)($R^{17}$)—, —C(O)— or —O—.

$A^2$ is a bond, —N═, —N($R^{15}$)—, ═C($R^{16}$)—, —C($R^{16}$)($R^{17}$)— or —C(O)—.

$R^{15}$, $R^{16}$ and $R^{17}$ are each independently selected from the group consisting of H, halogen, ($C_1$-$C_8$)alkyl, ($C_2$-$C_8$)heteroalkyl, fluoro($C_1$-$C_4$)alkyl, aryl, heteroaryl, aryl($C_1$-$C_8$)alkyl, heteroaryl($C_1$-$C_8$)alkyl, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)═NH, —NR'C(NH$_2$)═NH, —NHC(NH$_2$)═NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, wherein R', R" and R'" are each independently selected from H, ($C_1$-$C_8$)alkyl, ($C_2$-$C_8$)heteroalkyl, unsubstituted aryl, unsubstituted heteroaryl, (unsubstituted aryl)-($C_1$-$C_4$)alkyl, and (unsubstituted aryl)oxy-($C_1$-$C_4$)alkyl.

In certain embodiments, either the ring comprising $A^1$, $A^2$, $A^3$, $A^4$, $Y^1$ and $Y^2$, or the ring comprising X, $Y^1$, $Y^2$, $Y^3$, $Y^4$ and Z, or both rings, can be aromatic.

In certain embodiments of formula IV, $R^3$ is ($C_2$-$C_8$)heteroalkyl or cyclo($C_3$-$C_9$)heteroalkyl containing a thioether, sulfoxide, or sulfone.

In certain embodiments, X is a bond, and $R^1$, $R^z$ and $R^x$ are each H.

In certain embodiments, Q is —CH$_2$CO—, and $R^4$ is aryl or heteroaryl.

In some embodiments, Q-$R^4$ taken together is

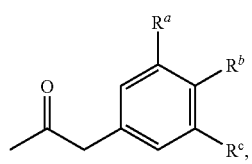

where $R^a$, $R^b$ and $R^c$ are each independently —H, halogen, —CN, —OCF$_3$, or —CF$_3$. In some embodiments, $R^a$ and $R^b$ are each independently halogen, —OCF$_3$, or —CF$_3$, and $R^c$ is —H. In some embodiments, $R^a$ is —CF$_3$, $R^b$ is —F and $R^c$ is —H.

In some embodiments of formula IV, $A^1$ and $A^3$ are ═C($R^{16}$)—; $A^2$ and $A^4$ are —N═ or ═C($R^6$)—; $R^1$ and $R^x$ are H; and each $R^{16}$ is a member independently selected from the group consisting of H, halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)═NH, —NR'C(NH$_2$)═NH, —NHC(NH$_2$)═NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, wherein R', R" and R'" are each independently selected from H, ($C_1$-$C_8$)alkyl, ($C_2$-$C_8$)heteroalkyl, unsubstituted aryl, unsubstituted heteroaryl, (unsubstituted aryl)-($C_1$-$C_4$)alkyl, and (unsubstituted aryl)oxy-($C_1$-$C_4$)alkyl.

In certain embodiments of formula IV, $R^1$, $R^z$ and $R^x$ are H; X is —C(O)—; Z is —N═; and $A^2$ is a bond.

In some embodiments, the compound of the present invention has formula V:

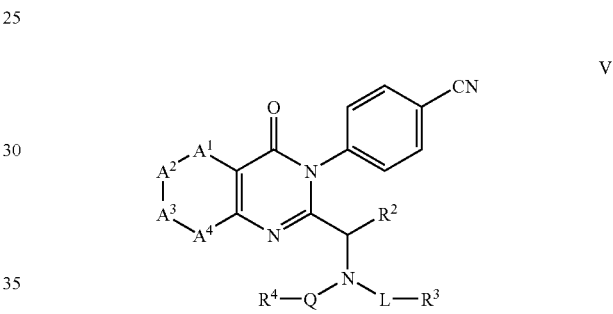

wherein L, Q, $R^2$, $R^3$ and $R^4$ are as described above in formula IV. Symbols $A^1$, $A^2$, $A^3$ and $A^4$ are as described below.

$A^1$, $A^2$ and $A^3$ are each independently —C($R^{16}$)($R^{17}$)— or —C(O)—.

$A^4$ is —N($R^{15}$)—, or —C($R^{16}$)($R^{17}$)—.

$R^{15}$, $R^{16}$ and $R^{17}$ are each independently H, halogen, ($C_1$-$C_8$)alkyl, ($C_2$-$C_8$)heteroalkyl, fluoro($C_1$-$C_4$)alkyl, aryl, heteroaryl, aryl($C_1$-$C_8$)alkyl or heteroaryl($C_1$-$C_8$)alkyl.

In certain embodiments, the compound of formula V is a racemic compound. In some embodiments, the compound of formula V is a mixture of (S) and (R) enantiomers.

In some embodiments, the compound has the formula Va or Vb:

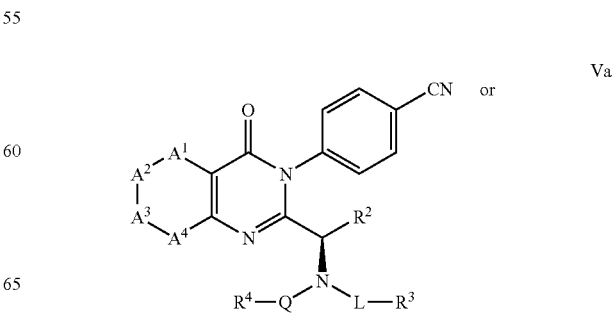

-continued

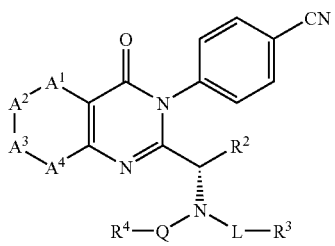
Vb where $A^1$, $A^2$, $A^3$, $A^4$, L, Q, $R^2$, $R^3$ and $R^4$ are as described above in formula V.

In additional embodiments, the present invention provides a compound that has formula VI:

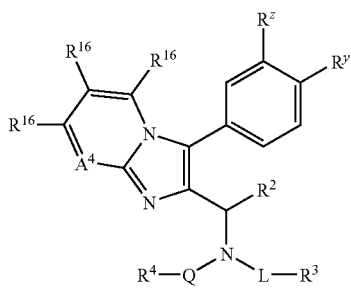
VI wherein L, Q, $R^2$, $R^3$, $R^4$, $R^{16}$, $R^y$, $R^z$ and $A^4$ are as described above in formula IV.

In certain embodiments, the compound of formula VI is a racemic compound. In some embodiments, the compound of formula VI is a mixture of (S) and (R) enantiomers. In some embodiments, the compound of formula VI is an (S) enantiomer. In some embodiments, the compound of formula VI is an (R) enantiomer.

In some embodiments, the compound of the present invention has formula VII:

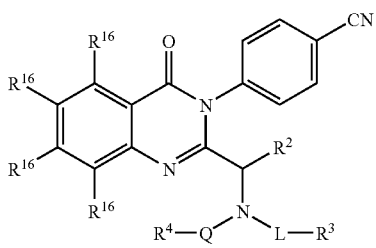
VII wherein L, Q, $R^2$, $R^3$, $R^4$ and $R^{16}$ are as described above in formula IV.

In certain embodiments, the compound of formula VII is a racemic compound. In some embodiments, the compound of formula VII is a mixture of (S) and (R) enantiomers. In some embodiments, the compound of formula VII is an (S) enantiomer. In some embodiments, the compound of formula VII is an (R) enantiomer.

In some embodiments, the compound of the present invention has formula VIII:

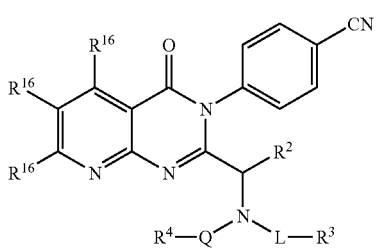
VIII wherein L, Q, $R^2$, $R^3$, $R^4$ and $R^{16}$ are as described above in formula IV.

In some embodiments, Q-$R^4$ taken together is

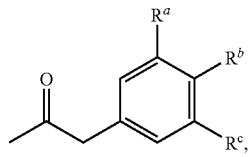

where $R^a$, $R^b$ and $R^c$ are each independently —H, halogen, —CN, —OCF$_3$, or —CF$_3$. In some embodiments, $R^a$ and $R^b$ are each independently halogen, —OCF$_3$, or —CF$_3$, and $R^c$ is —H. In some embodiments, $R^a$ is —CF$_3$, $R^b$ is —F and $R^c$ is —H.

In certain embodiments of formula VIII, $R^3$ is ($C_2$-$C_8$)heteroalkyl or cyclo($C_3$-$C_9$)heteroalkyl containing a thioether, sulfoxide, or sulfone.

In certain embodiments, the compound of formula VIII is a racemic compound. In some embodiments, the compound of formula VIII is a mixture of (S) and (R) enantiomers.

In certain embodiments, the compound has formula VIIIa or VIIIb:

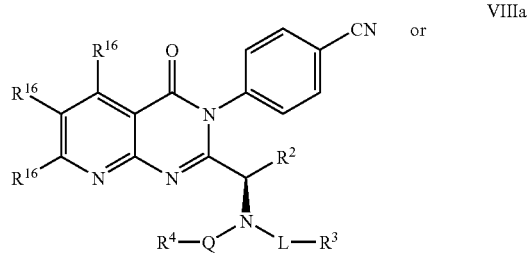
VIIIa or

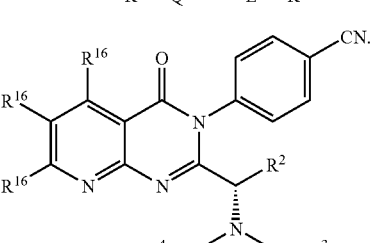
VIIIb where $R^2$, $R^3$, $R^4$, $R^{16}$, L and Q are as defined in formula VIII.

In certain embodiments, the compound is selected from the group consisting of:

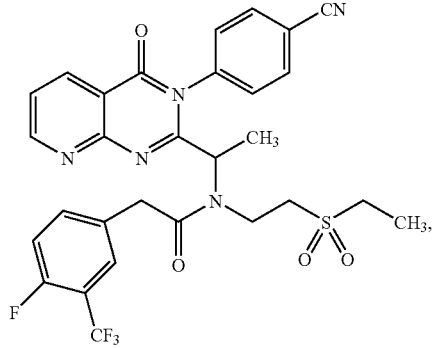

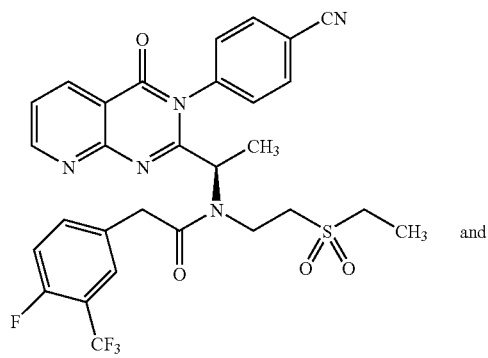

and

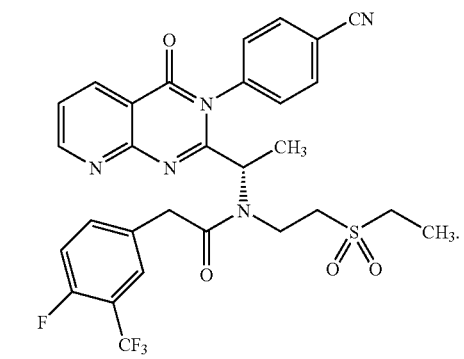

In some embodiments, the present invention provides a compound having formula IX:

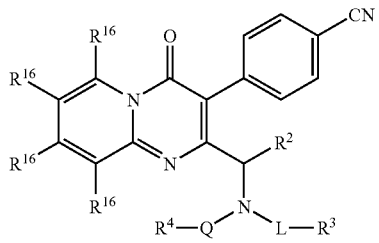

IX where L, Q, $R^2$, $R^3$, $R^4$ and $R^{16}$ are as described above in formula IV.

In some embodiments, Q-$R^4$ taken together is

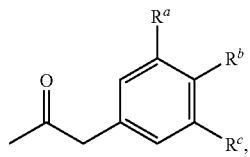

where $R^a$, $R^b$ and $R^c$ are each independently —H, halogen, —CN, —OCF$_3$, or —CF$_3$. In some embodiments, $R^a$ and $R^b$ are each independently halogen, —OCF$_3$, or —CF$_3$, and $R^c$ is —H. In some embodiments, $R^a$ is —CF$_3$, $R^b$ is —F and $R^c$ is —H.

In certain embodiments of formula IX, $R^3$ is (C$_2$-C$_8$)heteroalkyl or cyclo(C$_3$-C$_9$)heteroalkyl containing a thioether, sulfoxide, or sulfone.

In certain embodiments, the compound of formula IX is a racemic compound. In some embodiments, the compound of formula IX is a mixture of (S) and (R) enantiomers.

In certain embodiments, the compound has formula IXa or IXb:

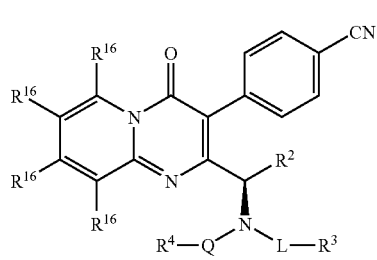

IXa

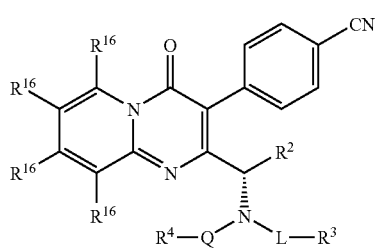

IXb where $R^2$, $R^3$, $R^4$, $R^6$, L and Q are as defined in formula IX.

In certain embodiments, the compound is selected from the group consisting of:

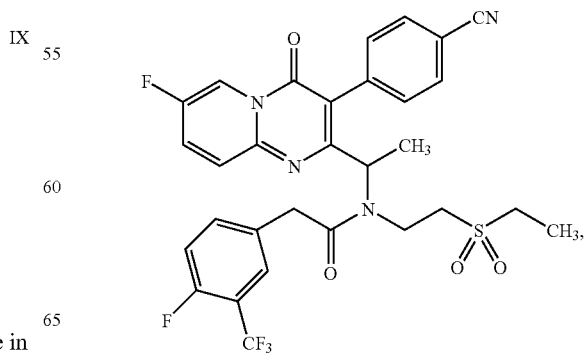

-continued

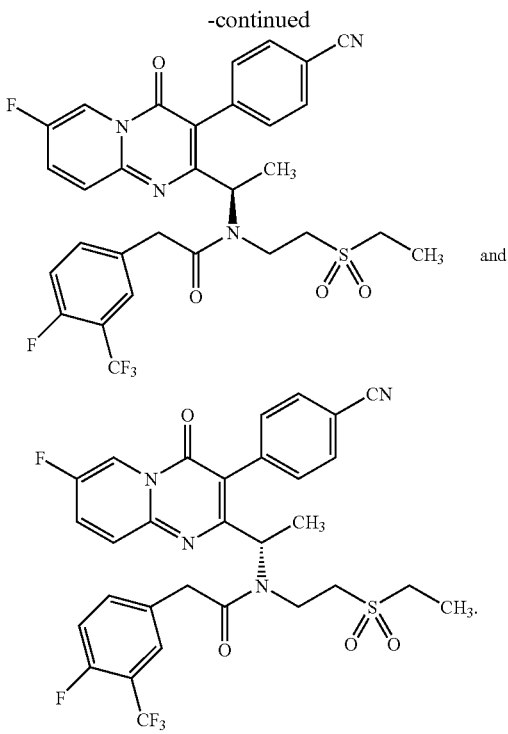

In some embodiments, the present invention provides a compound having formula X:

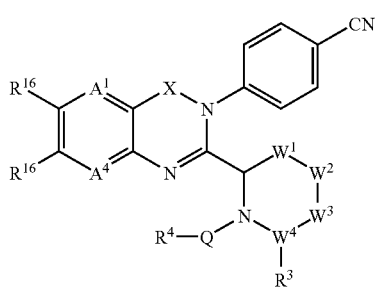

where Q, $R^3$, and $R^4$ are as defined in formula I above.

X is —C(O)—, —$CH_2$—, or —S(O)$_2$—.

$A^1$ and $A^4$ independently are N or C($R^{16}$), wherein each $R^{16}$ is a member independently selected from the group consisting of halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NHC(NH$_2$)=NR', —S(O)R', —S(O)$_2$R', —S(O)$_2$NR'R", —$N_3$, —CH(Ph)$_2$, perfluoro($C_1$-$C_4$)alkoxy, and perfluoro ($C_1$-$C_4$)alkyl, wherein R', R" and R'" are each independently selected from H, ($C_1$-$C_8$)alkyl, ($C_2$-$C_8$)heteroalkyl, unsubstituted aryl, unsubstituted heteroaryl, (unsubstituted aryl)-($C_1$-$C_4$)alkyl, and (unsubstituted aryl)oxy-($C_1$-$C_4$)alkyl.

$W^1$ is absent or is selected from the group consisting of —O—, —S—, —S(O)—, —S(O)$_2$—, —C(O)—, —$CH_2$— or —$NR^{18}$—.

$W^2$ and $W^4$ independently are —$CH_2$—, —$CHR^{19}$—, —CH=, —$CR^{19}$=, —NH—, —N= or —$NR^{18}$—.

$W^3$ is absent or is selected from the group consisting of —O—, —S—, —S(O)—, —S(O)$_2$—, —$CH_2$—, —$CHR^{20}$—, —CH=, —$CR^{20}$=, —NH—, —N= or —$NR^{20}$—.

$R^{18}$ is selected from the group consisting of H, ($C_1$-$C_8$) alkyl, ($C_2$-$C_8$)heteroalkyl, aryl and heteroaryl.

$R^{19}$ and $R^{20}$ are independently ($C_1$-$C_{20}$)alkyl, ($C_2$-$C_{20}$)heteroalkyl, heteroaryl, aryl, heteroaryl($C_1$-$C_6$)alkyl, heteroaryl ($C_2$-$C_6$)heteroalkyl, aryl($C_1$-$C_6$)alkyl and aryl($C_2$-$C_6$)heteroalkyl.

The compounds provided in the above formulas I-X include pharmaceutically acceptable salts, solvates, prodrugs or isomers thereof, unless otherwise indicated.

4.4. Preparation of the Compounds

The compounds of the invention can be prepared by a variety of synthetic or semisynthetic techniques. FIGS. 1-18 of International Publication No. WO 02/83143 and the Examples in Section 6 below provide a variety of synthesis routes to the compounds provided herein. Synthesis of appropriate starting materials can be prepared by techniques known or apparent to those of skill in the art or the starting materials may be commercially available. For instance, such materials can be prepared according to the methods of U.S. Patent Applications Nos. 2002/0160159 A1 and 2003/0055054 A1 and International Publication No. WO 02/83143, the contents of which are each hereby incorporated by reference in its entirety. One of skill in the art will appreciate that substituents can be added or altered before, during or after preparation of the heterocyclic scaffolding and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group.

The exemplary methods and the examples described herein are illustrative of the present invention and are not to be construed as limiting the scope thereof.

4.5. Compositions

In another aspect, the present invention provides pharmaceutical compositions for modulating chemokine receptor activity in humans and animals. The compositions comprise a compound of the present invention with a pharmaceutically acceptable excipient, carrier or diluent.

"Modulation" or modulating of chemokine receptor activity, as used herein in its various forms, is intended to encompass antagonism, agonism, partial antagonism and/or partial agonism of the activity associated with a particular chemokine receptor, preferably the CXCR3 receptor. The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically effective compounds as noted herein which are usually applied in the treatment or prevention of the above mentioned pathological conditions.

4.6. Methods of Use

In another aspect, the present invention provides methods of treating CXCR3-mediated conditions or diseases by administering to a subject having such a disease or condition, a therapeutically effective amount of compound or composition of the invention. The "subject" is defined herein to include animals such as mammals, including, but not limited to, primates (e.g., humans), cows, sheep, goats, horses, pigs, dogs, cats, rabbits, rats, mice and the like.

As used herein, the phrase "CXCR3-mediated condition or disease" and related phrases and terms refer to a condition characterized by inappropriate, e.g., less than or greater than normal, CXCR3 activity. Inappropriate CXCR3 activity might arise as the result of CXCR3 expression in cells which normally do not express CXCR3, increased CXCR3 expression (leading to, e.g., inflammatory and immunoregulatory disorders and diseases), or, decreased CXCR3 expression (leading to, e.g., certain cancers and angiogenic and vasculogenic-related disorders). Inappropriate CXCR3 functional activity might arise as the result of CXCR3 expression in cells which normally do not express CXCR3, increased CXCR3 expression (leading to, e.g., inflammatory and immunoregulatory disorders and diseases) or decreased CXCR3 expression. Inappropriate CXCR3 functional activity might also arise as the result of chemokine secretion by cells which normally do not secrete a CXC chemokine, increased chemokine expression (leading to, e.g., inflammatory and immunoregulatory disorders and diseases) or decreased chemokine expression. A CXCR3-mediated condition or disease may be completely or partially mediated by inappropriate CXCR3 functional activity. However, a CXCR3-mediated condition or disease is one in which modulation of CXCR3 results in some effect on the underlying condition or disease (e.g., a CXCR3 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

Diseases and conditions associated with inflammation, infection and cancer can be treated with the present compounds and compositions. In one group of embodiments, diseases or conditions, including chronic diseases, of humans or other species can be treated with inhibitors of CXCR3 function. These diseases or conditions include: (1) inflammatory or allergic diseases such as systemic anaphylaxis or hypersensitivity responses, drug allergies, insect sting allergies and food allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; asthma and respiratory allergic diseases such as allergic rhinitis, hypersensitivity lung diseases, and the like, (2) autoimmune diseases, such as arthritis (rheumatoid and psoriatic), multiple sclerosis, systemic lupus erythematosus, type I diabetes, glomerulonephritis, and the like, (3) graft rejection (including allograft rejection and graft-v-host disease) and conditions associated therewith, and (4) other diseases in which undesired inflammatory responses are to be inhibited, e.g., atherosclerosis, myositis, neurodegenerative diseases (e.g., Alzheimer's disease), encephalitis, meningitis, hepatitis, nephritis, sepsis, sarcoidosis, conjunctivitis, otitis, chronic obstructive pulmonary disease, sinusitis and Behcet's syndrome. In another group of embodiments, diseases or conditions are treated with agonists of CXCR3 function. Examples of diseases to be treated with CXCR3 agonists include cancers, diseases in which angiogenesis or neovascularization play a role (neoplastic diseases, retinopathy and macular degeneration), infectious diseases and immunosuppressive diseases.

Preferably, the present methods are directed to the treatment or prevention of diseases or conditions selected from neurodegenerative diseases (e.g., Alzheimer's disease), multiple sclerosis, psoriasis, systemic lupus erythematosus, rheumatoid arthritis, atherosclerosis, encephalitis, meningitis, hepatitis, nephritis, sepsis, sarcoidosis, psoriasis, eczema, uticaria, type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, gout, cancer, viral infections (e.g., HIV), bacterial infections, and organ transplant conditions or skin transplant conditions. The term "organ transplant conditions" is meant to include bone marrow transplant conditions and solid organ (e.g., kidney, liver, lung, heart, pancreas or combination thereof) transplant conditions.

Diseases or conditions that can be treated with the present compounds and compositions include diseases commonly associated with (1) inflammatory or allergic diseases, (2) autoimmune diseases, (3) graft rejection and (4) other diseases in which undesired inflammatory responses are to be inhibited, as described above. For example, restenosis following a procedure such as balloon angioplasty, is commonly associated with atherosclerosis and can be treated with the present compounds and compositions.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to treat or prevent inflammatory and immune disorders and diseases, including asthma and allergic diseases, as well as autoimmune pathologies such as rheumatoid arthritis and atherosclerosis, and those pathologies noted above. In many instances, compositions which include a compound of the invention and an alternative or second therapeutic agent have additive or synergistic effects when administered.

For example, in the treatment or prevention of inflammation, the present compounds may be used in conjunction or combination with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporine (cyclosporine A, Sandimmune®, Neoral®, tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal anti-inflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) gold compounds such as auranofin and aurothioglucose, (j) inhibitors of phosphodiesterase type IV (PDE-IV); (k) other antagonists of the chemokine receptors, especially CCR1, CCR2, CCR3, CCR5, CCR6, CCR8 and CCR10; (l) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (m) anti-diabetic agents such as insulin, sulfonylureas, biguamides (metformin), α-glucosidase inhibitors (acarbose) and glitazones (troglitazone and pioglitazone); (n) preparations of interferon beta (interferon β-1α, interferon β-1β); (O) etanercept (Enbrel®), (p) antibody therapies such as orthoclone (OKT3), daclizumab (Zenapax®), infliximab (Remicade®), basiliximab (Simulect®) and anti-CD40 ligand antibodies (e.g., MRP-1); and (q) other compounds such as 5-aminosalicylic acid and prodrugs thereof, hydroxychloroquine, D-penicillamine, antimetabolites such as azathioprene and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Immunosuppressants within the scope of the present invention further include, but are not limited to, leflunomide, RAD001, ERL080, FTY720, CTLA-4, antibody therapies such as orthoclone (OKT3), daclizumab (Zenapax®) and basiliximab (Simulect®), and antithymocyte globulins such as thymoglobulins.

In particularly preferred embodiments, the present methods are directed to the treatment or prevention of multiple sclerosis using a compound of the invention either alone or in combination with a second therapeutic agent selected from betaseron, avonex, azathioprene (Imurek®, Imuran®), capoxone, prednisolone and cyclophosphamide. When used in combination, the practitioner can administer a combination of the therapeutic agents, or administration can be sequential.

In still other particularly preferred embodiments, the present methods are directed to the treatment or prevention of rheumatoid arthritis, wherein the compound of the invention is administered either alone or in combination with a second therapeutic agent selected from the group consisting of methotrexate, sulfasalazine, hydroxychloroquine, cyclosporine A, D-penicillamine, infliximab (Remicade®), etanercept (Enbrel®), auranofin and aurothioglucose.

In yet other particularly preferred embodiments, the present methods are directed to the treatment or prevention of an organ transplant condition wherein the compound of the invention is used alone or in combination with a second therapeutic agent selected from the group consisting of cyclosporine A, FK-506, rapamycin, mycophenolate, prednisolone, azathioprene, cyclophosphamide and an antilymphocyte globulin.

5. EXAMPLES

Reagents and solvents used below can be obtained from commercial sources such as Sigma-Aldrich Co. (St. Louis, Mo., USA). $^1$H-NMR spectra were recorded on a Bruker 500 MHZ NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electrospray ionization (ESI) mass spectrometry analysis was conducted on a Hewlett-Packard 1100 MSD electrospray mass spectrometer using the HP 1100 HPLC for sample delivery. Mass spectrometry results are reported as the ratio of mass over charge. Each compound was dissolved in methanol at 0.1 mg/mL and 1 microliter was infused with the delivery solvent into the mass spectrometer, which scanned from 100 to 1500 daltons. Each compound could be analyzed in the positive ESI mode, using 1:1 acetonitrile/water with 1% acetic acid as the delivery solvent. Each compound could also be analyzed in the negative ESI mode, using 2 mM NH$_4$OAc in acetonitrile/water as delivery solvent.

5.1. Example 1

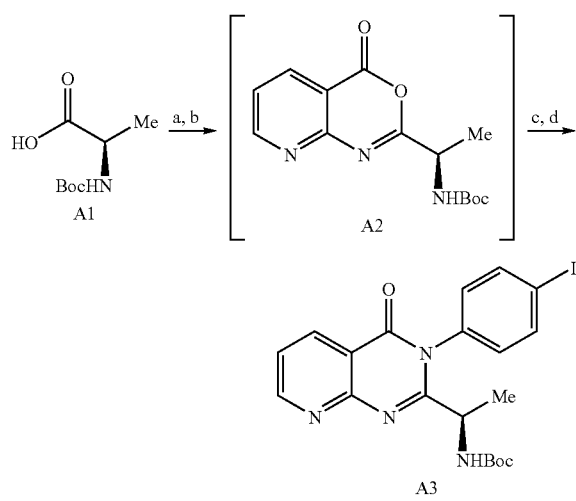

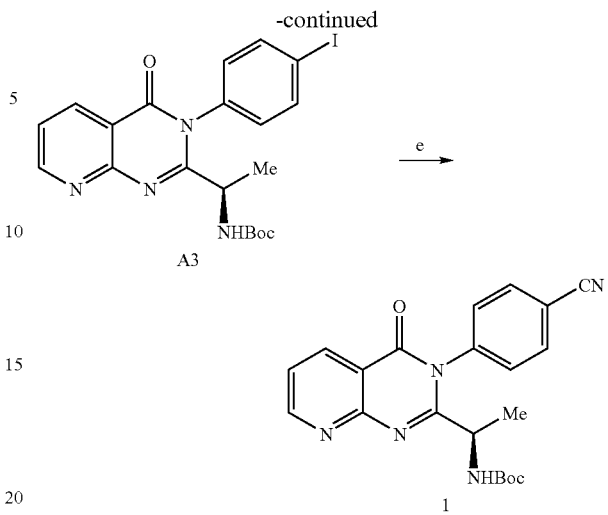

(a) NMM, ICBF, CH$_2$Cl$_2$, −25° C., 1.5 h; (b) 2-aminonicotinic acid, CH$_2$Cl$_2$, −25 to 15° C., 12 h; (c) 1) 4-iodoaniline, CH$_2$Cl$_2$, −10 to 15° C., 12 h; (d) NMM, IBCF, CH$_2$Cl$_2$, −25° C., 12 h (13% overall); (e) (Ph$_3$P)$_4$Pd, CuI, NaCN, MeCN, 70° C., 30 min (89%).

Compound 1 was synthesized from commercially available starting materials as shown in Scheme A.

(R)-tert-butyl 1-(3-(4-iodophenyl)-4-oxo-3,4-dihydropyrido[2,3-d]pyrimidin-2-yl)ethylcarbamate (A3). A solution of Boc-d-alanine, A1 (10.0 g, 52.9 mmol) in CH$_2$Cl$_2$ (140 mL) was cooled to −25° C. (measured internally). N-Methylmorpholine (NMM) (13.8 mL, 125 mmol) followed by iso-butylchloroformate (IBCF) (13.5 mL, 104 mmol) were added at such a rate to maintain the internal temperature below −25° C. After 1.5 h the mixture was transferred via cannula to a 250 mL, three-neck flask equipped with a thermometer and containing dry 2-aminonicotinic acid (7.28 g, 52.7 mmol). After the addition was complete (ca. 10 min.) the internal temperature of the mixture was adjusted to −10° C. The reaction mixture was allowed to warm with vigorous stirring over 17 h reaching a final temperature of 15° C. The mixture was cooled to 0° C. and washed with ice-cold 1N HCl (2×100 mL), brine (100 mL) and dried over Na$_2$SO$_4$. The resulting solution of A2 was charged into a 250 mL three neck, cooled to −25° C. and treated with solid 4-iodoaniline (11.61 g, 53 mmol). The resulting dark mixture was allowed to warm to 15° C. with stirring over 12 h. The solution was washed with 1N HCl (2×100 mL), saturated NaHCO$_3$ (2×100 mL), brine (100 mL) and dried over Na$_2$SO$_4$. The mixture was cooled to −25° C. and treated with NMM (6.8 mL, 61.8 mmol) followed by IBCF (6.7 mL, 56.1) maintaining the internal temperature below −25° C. After stirring for 12 h the reaction mixture was washed with 1N HCl (2×100 mL), saturated NaHCO$_3$ (2×100 mL), brine (100 mL) and dried over Na$_2$SO$_4$ and concentrated. Purification of the concentrate by silica gel chromatography (50×400 mm column; 5% acetone/CH$_2$Cl$_2$ to 25% acetone/CH$_2$Cl$_2$) gave A3 (3.41 g, 13%; purity 96% AUC). R$_f$=0.37 (15% acetone/CH$_2$Cl$_2$).

(R)-tert-butyl 1-(3-(4-cyanophenyl)-4-oxo-3,4-dihydropyrido[2,3-d]pyrimidin-2-yl)ethylcarbamate (1). A3 (2.02 g, 4.10 mmol), (Ph$_3$P)$_4$Pd (439 mg, 0.38 mmol), CuI (157 mg, 0.82 mmol) and NaCN (406 mg, 8.29 mmol) were combined in a 25 mL pear shaped flask equipped with a reflux condenser. The mixture was evacuated under high vacuum and backfilled with dry N$_2$ three times. Acetonitrile (6 mL) was then added and the resulting suspension heated to 70° C. for 30 min. at which point TLC and HPLC analysis indicated near complete consumption of A3. The mixture was diluted with EtOAc (100 mL) and filtered through a pad of celite. The filtrate was washed with saturated NaHCO$_3$ (100 mL). The aqueous wash was extracted with additional EtOAc (2×50 mL). The combined extracts were dried over Na$_2$SO$_4$ and concentrated. Purification of the residue by silica gel chromatography (50×400 mm column; 80% EtOAc/hexanes to 100% EtOAc) gave 1 (1.42 g, 89%; purity 96% AUC; 92% e.e. by chiral HPLC analysis). Rf=0.35 (80% EtOAc/hexanes).

5.2. Example 2

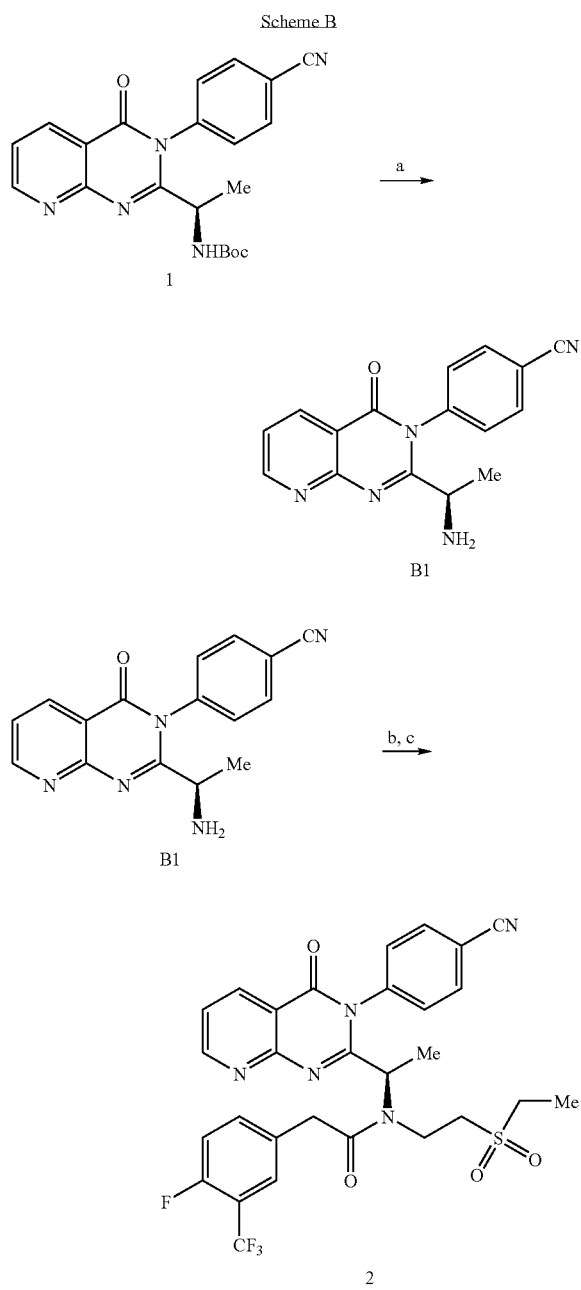

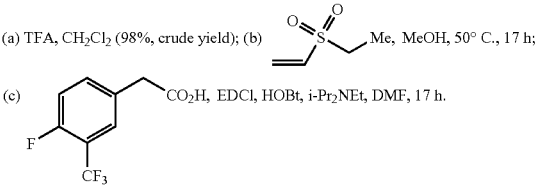

(a) TFA, CH$_2$Cl$_2$ (98%, crude yield); (b) vinyl-SO$_2$-Me, MeOH, 50° C., 17 h; (c) 4-fluoro-3-(trifluoromethyl)phenyl-CH$_2$-CO$_2$H, EDCl, HOBt, i-Pr$_2$NEt, DMF, 17 h.

(R)-4-(2-(1-aminoethyl)-4-oxopyrido[2,3-d]pyrimidin-3(4H)-yl)benzonitrile (B1). Compound 1 (1.05 g, 2.68 mmol) was dissolved in CH$_2$Cl$_2$ (40 mL) and treated with TFA (40 mL). The resulting mixture was stirred for 1.5 h then concentrated in vacuo. The concentrate was re-dissolved in CH$_2$Cl$_2$ (100 mL) and washed with saturated NaHCO$_3$ (100 mL). The aqueous wash was extracted with additional CH$_2$Cl$_2$ (3×50 mL). The combined extracts were dried over Na$_2$SO$_4$, concentrated and dried under high vacuum for 17 h to give B1 (767 mg, 98%), which was suitable for use without further purification.

(R) N-(1-(3-(4-cyanophenyl)-4-oxo-3,4-dihydropyrido[2,3-d]pyrimidin-2-yl)ethyl)-N-(2-(ethylsulfonyl)ethyl)-2-(4-fluoro-3-(trifluoromethyl)phenyl)-acetamide (2). Crude B1 (567 mg, 1.95 mmol) and ethylvinylsulfone (0.26 mL, 2.49 mmol) were combined in anhydrous MeOH (6.5 mL). The mixture was heated to 50° C. (external temperature) with stirring for 17 hours, at which time LC-MS analysis of the reaction mixture indicated complete consumption of the starting material. The reaction mixture was partitioned between EtOAc (100 mL) and water (50 mL). The EtOAc layer was washed with water (2×50 mL). The combined washes were extracted with EtOAc (2×50 mL). The combined extracts were dried over Na$_2$SO$_4$ and concentrated. The residue was combined with 4-fluoro-3-triflouromethylphenylacetic acid (680 mg, 2.93 mmol), EDCI (2.98 mmol) and HOBt (376 mg, 2.78 mmol) in DMF (5 mL). The resulting mixture was treated with Hunig's base (1.35 mL, 7.75 mmol) and allowed to stir at room temperature for 17 hours. The reaction mixture was diluted with EtOAc (200 mL) and washed with 1N HCl (2×100 mL). The combined washes were extracted with EtOAc (2×100 mL). The combined extracts were washed with saturated NaHCO$_3$ (200 mL), water (3×100 mL) and brine (100 mL), then dried over Na$_2$SO$_4$ and concentrated. The residue was purified by silica gel chromatography (10% THF/CH$_2$Cl$_2$ to 20% THF/CH$_2$Cl$_2$ to 100% THF) to give 2 (780 mg, 1.27 mmol, 65%) as an amorphous white solid with >97% purity AUC at 254 nM. R$_f$=0.2 (15% THF/CH$_2$Cl$_2$). DSC showed only endothermal event at 179° C.

5.3. Example 3

This example describes the synthesis of compound 3 from commercially available starting materials.

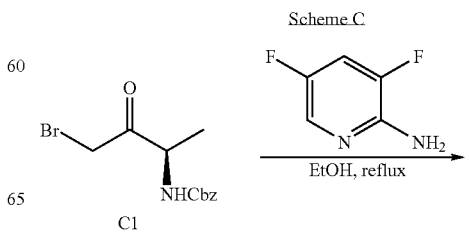

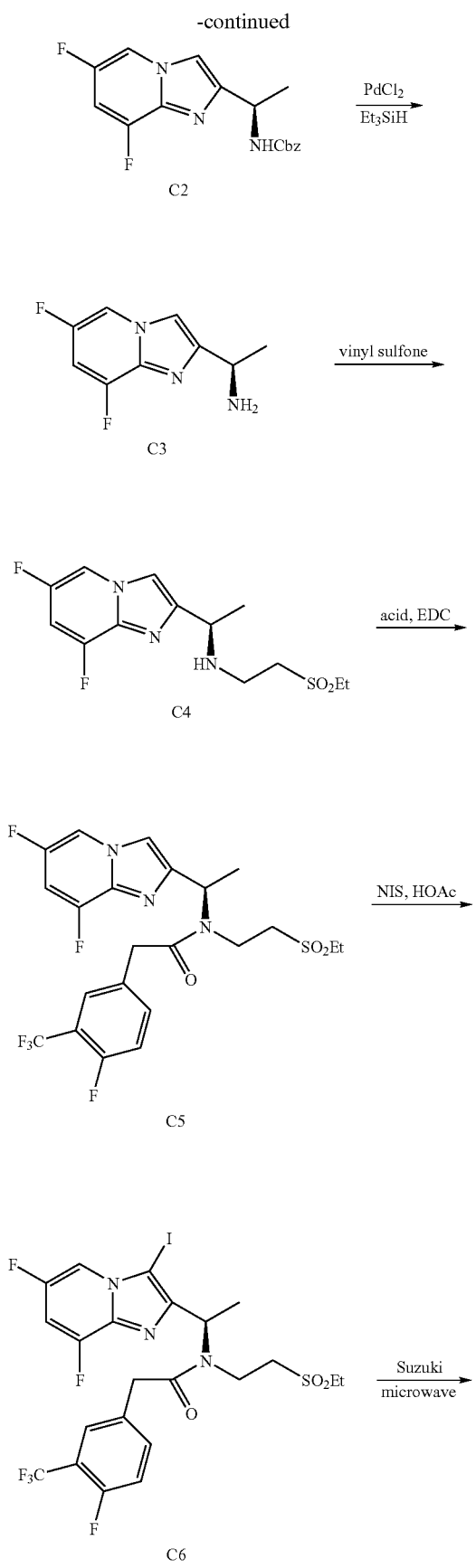

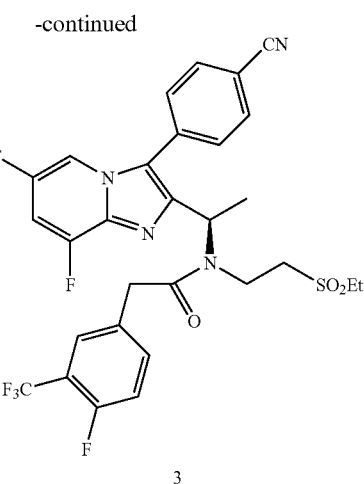

(R)-Benzyl 1-(6,8-difluoroH-imidazo[1,2-a]pyridin-2-yl) ethylcarbamate (C2). To a flask was added 2-amino-3,5-difluoropyridine (1.56 g, 12 mmol) and (R)-benzyl 4-bromo-3-oxobutan-2-ylcarbamate C1 (3.6 g, 12 mmol) followed by 35 mL anhydrous ethanol. The resulting reaction mixture was heated up to reflux overnight. The solvent was then removed and the reaction was partitioned between ethyl acetate and saturated sodium bicarbonate solution. The ethyl acetate layer was dried and concentrated. Addition of a small amount of ether produced crystals that were pure product. The remaining mixture was chromatographed with 4:1 dichloromethane:ethyl acetate. A total of 1.75 g of C2 was generated.

(R)-1-(6,8-DifluoroH-imidazo[1,2-a]pyridin-2-yl)ethanamine (C3). C2 (1.51 g, 4.6 mmol) was azeotroped with toluene. $PdCl_2$ was added to the flask and the reaction flask was flushed with nitrogen. Then, anhydrous dichloromethane (23 mL) was added followed by triethylamine (446 μL, 3.2 mmol), and triethylsilane (2.92 mL, 18.3 mmol). The resulting mixture was refluxed for 1 hr. 20 min. Saturated ammonium chloride was added to quench the reaction mixture. The dichloromethane layer was set aside. Solid sodium bicarbonate was added to adjust the pH of aqueous layer to 8. Then the aqueous layer was extracted with 30% isopropanol in chloroform five times. The combined isopropanol chloroform extract was dried, concentrated to give C3 (836 mg), which was used without further purification.

(R)-1-(6,8-DifluoroH-imidazo[1,2-a]pyridin-2-yl)-N-(2-(ethylsulfonyl)ethyl)ethanamine (C4). C3 (836 mg, 4.2 mmol) was dissolved in 21 mL methanol. Triethylamine (0.59 mL, 4.2 mmol) was added followed by ethyl vinyl sulfone (0.44 mL, 4.2 mmol). The reaction was heated at 50° C. overnight. After removal of methanol, the mixture was purified by chromatography with 1:1 dichloromethane:ethyl acetate then 3% methanol in dichloromethane and 6% methanol in dichloromethane to give 1.1 g of C4.

(R)-N-(1-(6,8-DifluoroH-imidazo[1,2-a]pyridin-2-yl) ethyl)-N-(2-(ethylsulfonyl)ethyl)-2-(4-fluoro-3-(trifluoromethyl)phenyl)acetamide (C5). To a flask with C4 (1.03 g, 3.2 mmol) was added 2-(4-fluoro-3-(trifluoromethyl)phenyl) acetic acid (794 mg, 3.6 mmol), EDC (1.87 g, 9.8 mmol), HOBt (220 mg, 1.6 mmol), followed by 40 mL of anhydrous DMF and N-methyl morpholine (1.07 mL, 9.8 mmol). The reaction was stirred at room temperature overnight and worked up with ethyl acetate and water. Column chromatography gave C5 (1.64 g).

(R)-N-(1-(6,8-Difluoro-3-iodoH-imidazo[1,2-a]pyridin-2-yl)ethyl)-N-(2-(ethylsulfonyl)ethyl)-2-(4-fluoro-3-(trifluoromethyl)phenyl)acetamide (C6). C5 (309 mg, 0.59 mmol) was dissolved in acetic acid 4 mL. N-iodosuccinamide (140 mg, 0.59 mmol) was added. The iodination was complete in 25 min. Water was added and the reaction was extracted with ethyl acetate. The ethyl acetate layer was dried and concentrated and chromatographed with dichloromethane and ethyl acetate to give 240 mg C6.

(R)-N-(1-(3-(4-Cyanophenyl)-6,8-difluoroH-imidazo[1,2-a]pyridin-2-yl)ethyl)-N-(2-(ethylsulfonyl)ethyl)-2-(4-fluoro-3-(trifluoromethyl)phenyl)acetamide (3). C6 (157 mg, 0.24 mmol), 4-cyanophenyl boronic acid (43 mg, 0.29 mmol), and Pd(dppf)$_2$Cl$_2$ (20 mg, 0.024 mmol) was added into a 10 mL CEM microwave tube, followed by THF (2.4 mL) and sodium carbonate (1.2 mL, 2M). The mixture was reacted by microwave at 150° C. for 10 min and then partitioned between water and ethyl acetate. Column chromatography with gradient dichloromethane:ethyl acetate (4:1 to 3:1 to 2:1) afforded 115 mg compound 3 as a light yellow solid. The product existed as a pair of rotamers (1:0.88) by NMR. $^1$H NMR (CDCl$_3$, 500 MHz): δ 7.94 (d, J=7.8, 1.7H), 7.9 (m, 3H), 7.66 (s, 1H), 7.61 (m, 4H), 7.52 (m, 2.3H), 7.25 (d, J=6.6, 0.8H), 7.19 (dd, J=7.5, 8.7, 1.9H), 7.04 (m, 1.9H), 5.96 (q, J=7.2, 1H), 5.27 (q, J=7.0, 0.9H), 4.10 (m, 1.9H), 3.83 (m, 3.7H), 3.55 (s, 1.6H), 3.44 (m, 1H), 3.20 (m, 1.9H), 3.06 (m, 4.6H), 1.61 (d, J=6.8, 2.6H), 1.56 (d, J=7.0, 3H), 1.47 (t, J=7.4, 3H), 1.37 (t, J=7.4, 2.7H). LC/MS (ES): 623.0 [M+H].

5.4. Example 4

The following examples were synthesized by modifying Scheme C as described in Section 5.3.

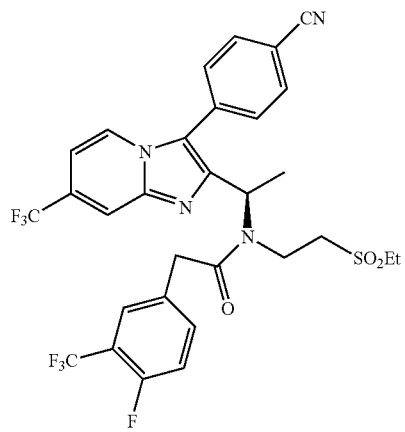

Compound 4.02. LC/MS (ES): 655.2 [M+H].

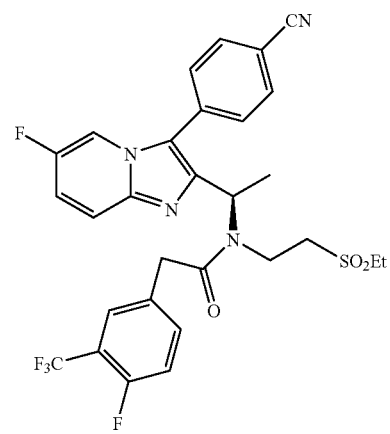

Compound 4.03. LC/MS (ES): 605.2 [M+H].

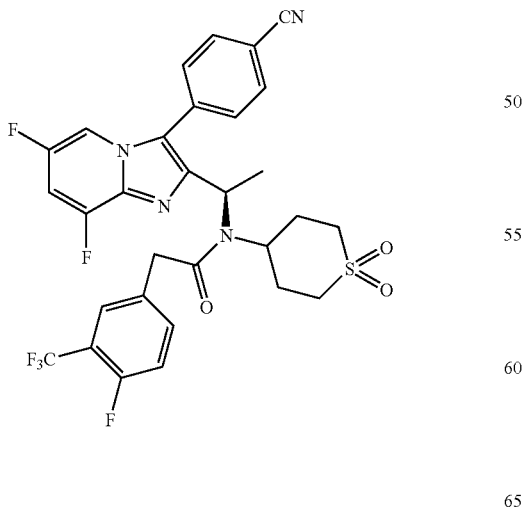

Compound 4.01. LC/MS (ES): 635.0 [M+H].

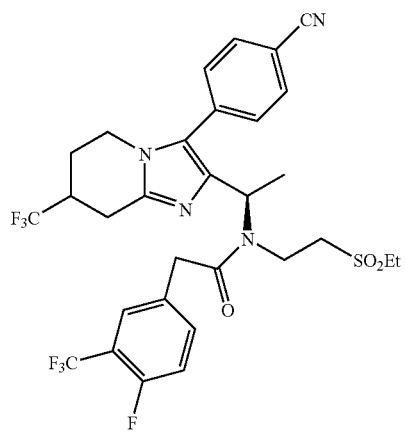

Compound 4.04. LC/MS (ES): 659.2 [M+H]

5.5. Example 5

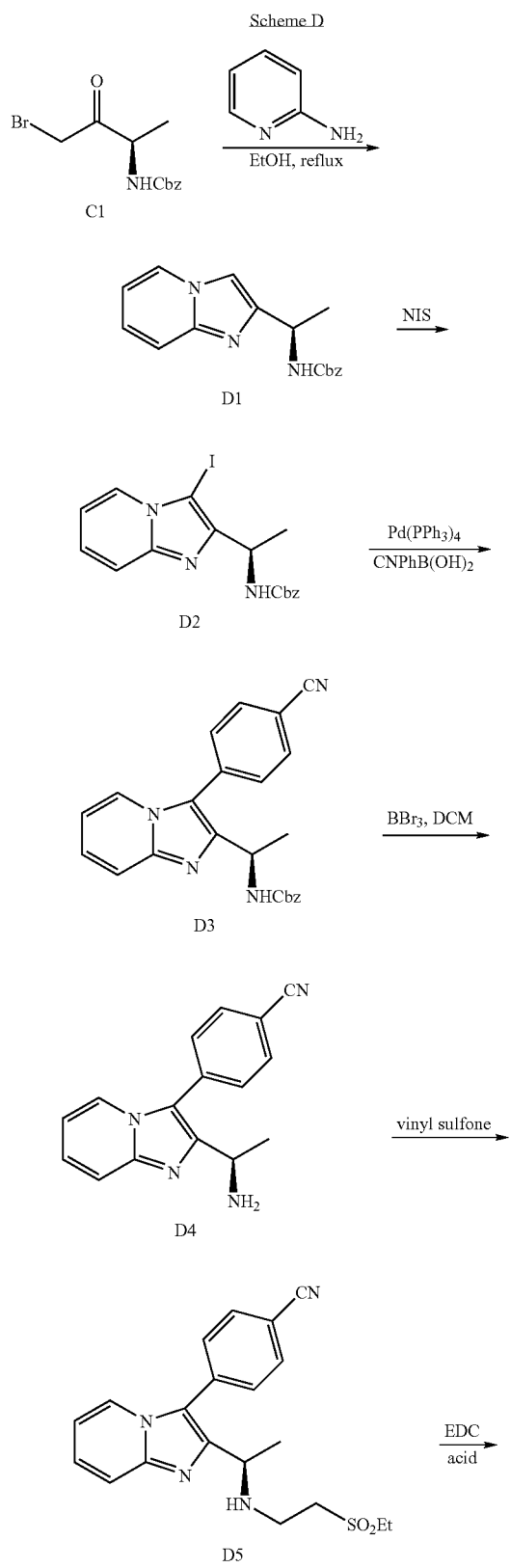

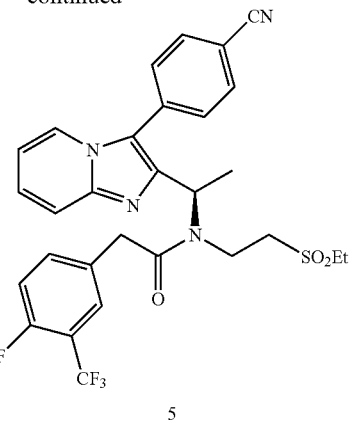

(R)-Benzyl 1-(H-imidazo[1,2-a]pyridin-2-yl)ethylcarbamate (D1). Ninety-eight milligrams (1 mmol) of 2-aminopyridine and C1 (300 mg, 1 mmol) was added to a flask followed by 3.6 mL anhydrous ethanol. The resulting reaction mixture was heated up to reflux overnight. The solvent was then removed and the reaction was partitioned between ethyl acetate and saturated sodium bicarbonate solution. The ethyl acetate layer was dried and concentrated. The mixture was chromatographed to give 122 mg of D1 as a white solid.

(R)-Benzyl 1-(3-iodoH-imidazo[1,2-a]pyridin-2-yl)ethylcarbamate (D2). D1 (1.36 g, 4.6 mmol) was dissolved in anhydrous acetonitrile 10 mL, to which N-iodosuccinamide (1.09 g, 4.6 mmol) was added. The iodination was complete in 30 min. The precipitate was filtered off and the acetonitrile was removed. The residue was redissolved in ethyl acetate and washed with saturated sodium bicarbonate solution twice. The ethyl acetate layer was dried and concentrated to give 2.1 g of D2 as an oil which was used without further purification.

(R)-Benzyl 1-(3-(4-cyanophenyl)H-imidazo[1,2-a]pyridin-2-yl)ethylcarbamate (D3). D2 (1 g, 2.4 mmol) was azeotroped with toluene. 4-cyanophenylboronic acid (436 mg, 3 mmol) and Pd(PPh3)4 (270 mg, 0.24 mmol) was added followed by dimethoxyethane 20 mL and sodium carbonate (1.9 mL, 0.5 M). The resulting mixture was heated at 80° C. overnight under nitrogen. Water was added and the mixture was extracted with ethyl acetate. After drying and concentration, the residue was purified with chromatography by dichloromethane/ethyl acetate (4:1 to 3:1) to give D3 (570 mg) as foamy solid.

(R)-4-(2-(1-Aminoethyl)H-imidazo[1,2-a]pyridin-3-yl)benzonitrile (D4). D3 (300 mg, 0.76 mmol) was dissolved in anhydrous dichloromethane followed by dropwise addition of BBr3 (3.8 mL, 1M in dichloromethane) at −10° C. under nitrogen. Stirring was continued at −10° C. for 1 hr. then at room temperature for 1 hr. Saturated sodium bicarbonate solution was added to quench the reaction followed by extraction with ethyl acetate twice and 30% isopropanol/chloroform once. The combined organic layers were dried and concentrated. Column purification with gradient methanol in dichloromethane with 1% ammonium hydroxide afforded 105 mg D4 as a solid.

(R)-4-(2-(1-(2-(Ethylsulfonyl)ethylamino)ethyl)H-imidazo[1,2-a]pyridin-3-yl)benzonitrile (D5). D4 (48.8 mg, 0.19 mmol) was dissolved in 2 mL methanol with ethyl vinyl sulfone (20 μL, 0.19 mmol). The reaction was heated at 50° C. overnight. After removal of methanol, the mixture was purified by chromatography with 1:1 dichloromethane:ethyl acetate then gradient methanol in dichloromethane (2% to 4% to 6%) to give D5 (29.6 mg) as an oil.

(R)-N-(1-(3-(4-Cyanophenyl)H-imidazo[1,2-a]pyridin-2-yl)ethyl)-N-(2-(ethylsulfonyl)ethyl)-2-(4-fluoro-3-(trifluoromethyl)phenyl)acetamide (5). To a flash with D4 (29.6 mg, 0.08 mmol) was added 2-(4-fluoro-3-(trifluoromethyl)phenyl)acetic acid (19 mg, 0.086 mmol), EDC (45 g, 0.23 mmol), HOBt (6 mg, 0.043 mmol), followed by 2.2 mL of anhydrous DMF and N-methyl morpholine (26 μL, 0.23 mmol). The reaction was stirred at room temperature overnight and worked up with ethyl acetate and water. Column chromatography gave 46 mg of 5 as a foamy solid. The product existed as a pair of rotamers (1:0.7) by NMR. $^1$H NMR (CDCl$_3$, 400 MHz): δ 8.10 (d, J=6.8, 0.7H), 7.91 (d, J=8.7, 2.8H), 7.84 (d, J=8.2, 1.4H), 7.70 (d, J=9.2, 1H), 7.55 (m, 5.1H), 7.35 (t, J=7.8, 1.7H), 7.24 (m, 2.1H), 7.19 (dd, J=9.7, 11.9, 2H), 6.90 (t, J=6.6, 1.7H), 6.00 (q, J=7.0, 0.7H), 5.26 (q, J=6.8, 1H), 4.14 (m, 1.4H), 3.96-3.80 (m, 4.2H), 3.51 (m, 2H), 3.17 (m, 1.6H), 3.00 (m, 4.4H), 1.63 (d, J=6.9, 3H), 1.57 (d, J=7.0, 2.1H), 1.40 (t, J=7.5, 2.1H), 1.36 (t, J=7.5, 3H). LC/MS (ES): 587.2 [M+H].

5.6. Example 6

The following examples were synthesized by modifying Scheme D as described in Section 5.5.

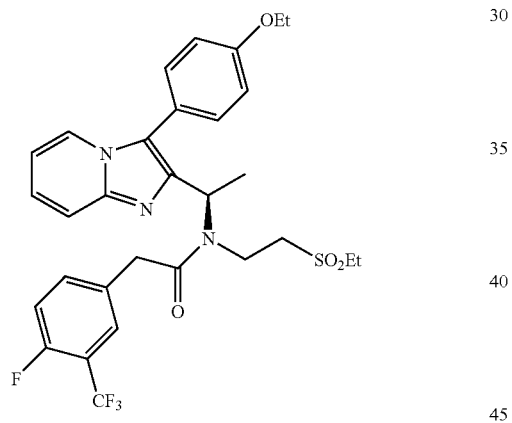

Compound 6.01. LC/MS (ES): 606.1 [M+H].

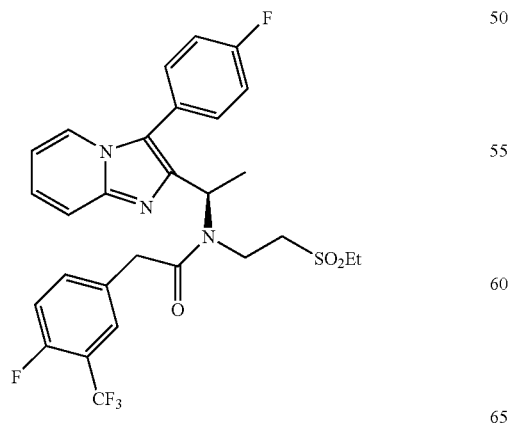

Compound 6.02. LC/MS (ES): 580.2 [M+H].

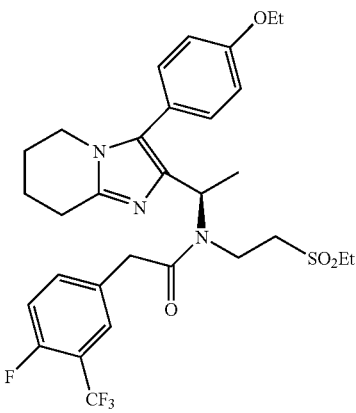

Compound 6.03. LC/MS (ES): 610.2 [M+H]

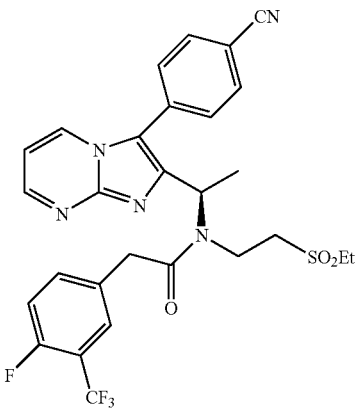

Compound 6.04. LC/MS (ES): 588.1 [M+H]

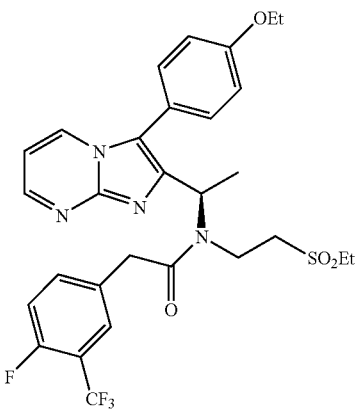

Compound 6.05. LC/MS (ES): 607.3 [M+H]

5.7. Example 7

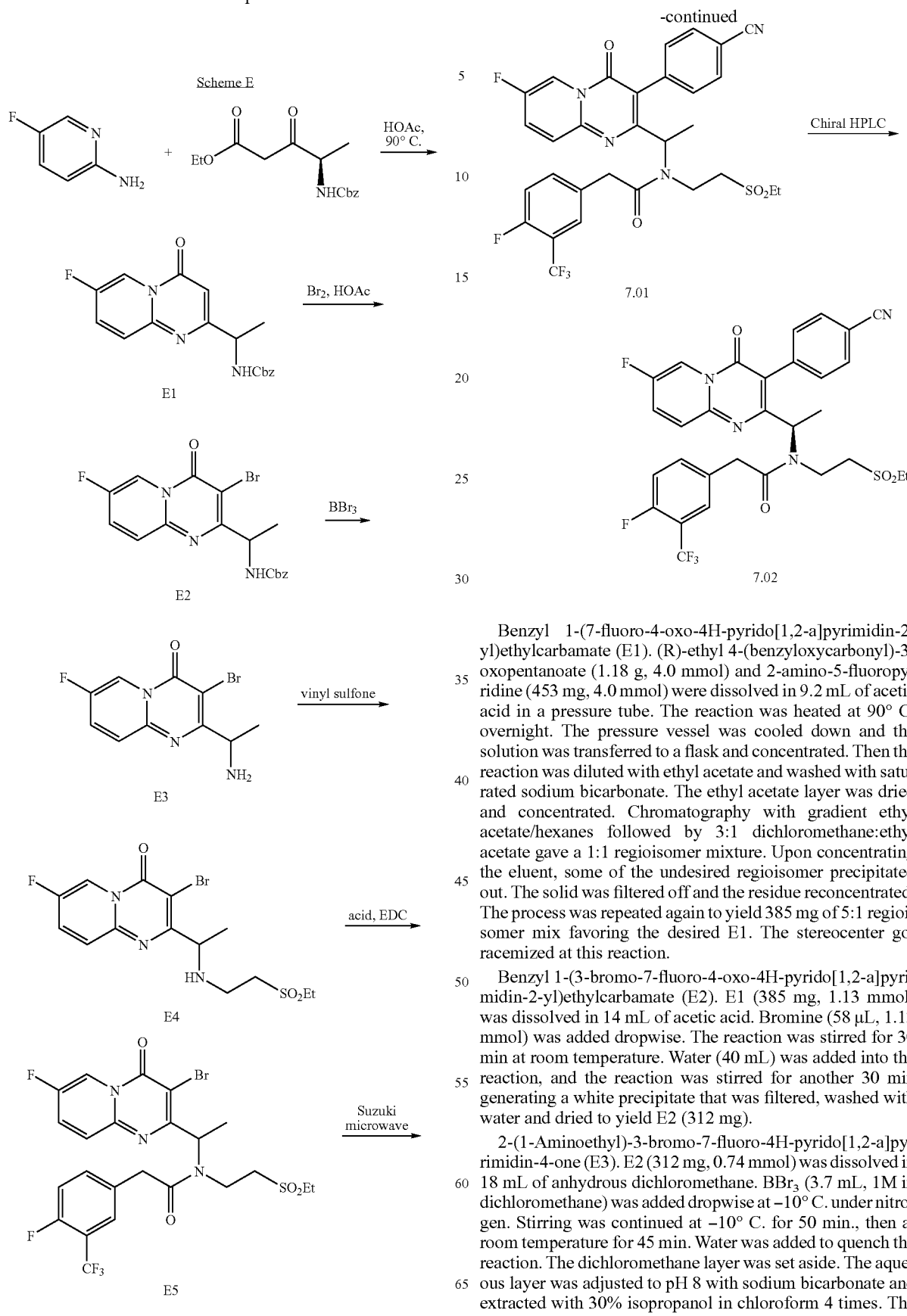

Benzyl 1-(7-fluoro-4-oxo-4H-pyrido[1,2-a]pyrimidin-2-yl)ethylcarbamate (E1). (R)-ethyl 4-(benzyloxycarbonyl)-3-oxopentanoate (1.18 g, 4.0 mmol) and 2-amino-5-fluoropyridine (453 mg, 4.0 mmol) were dissolved in 9.2 mL of acetic acid in a pressure tube. The reaction was heated at 90° C. overnight. The pressure vessel was cooled down and the solution was transferred to a flask and concentrated. Then the reaction was diluted with ethyl acetate and washed with saturated sodium bicarbonate. The ethyl acetate layer was dried and concentrated. Chromatography with gradient ethyl acetate/hexanes followed by 3:1 dichloromethane:ethyl acetate gave a 1:1 regioisomer mixture. Upon concentrating the eluent, some of the undesired regioisomer precipitated out. The solid was filtered off and the residue reconcentrated. The process was repeated again to yield 385 mg of 5:1 regioisomer mix favoring the desired E1. The stereocenter got racemized at this reaction.

Benzyl 1-(3-bromo-7-fluoro-4-oxo-4H-pyrido[1,2-a]pyrimidin-2-yl)ethylcarbamate (E2). E1 (385 mg, 1.13 mmol) was dissolved in 14 mL of acetic acid. Bromine (58 µL, 1.13 mmol) was added dropwise. The reaction was stirred for 30 min at room temperature. Water (40 mL) was added into the reaction, and the reaction was stirred for another 30 min generating a white precipitate that was filtered, washed with water and dried to yield E2 (312 mg).

2-(1-Aminoethyl)-3-bromo-7-fluoro-4H-pyrido[1,2-a]pyrimidin-4-one (E3). E2 (312 mg, 0.74 mmol) was dissolved in 18 mL of anhydrous dichloromethane. BBr$_3$ (3.7 mL, 1M in dichloromethane) was added dropwise at −10° C. under nitrogen. Stirring was continued at −10° C. for 50 min., then at room temperature for 45 min. Water was added to quench the reaction. The dichloromethane layer was set aside. The aqueous layer was adjusted to pH 8 with sodium bicarbonate and extracted with 30% isopropanol in chloroform 4 times. The dichloromethane layer was washed with brine and the brine layer was adjusted to pH 8 with sodium bicarbonate and extracted with 30% isopropanol in chloroform 1 times. The combined 30% isopropanol in chloroform extracts were dried and concentrated to give 222 mg of E3 as a solid, which was used directly for next step.

3-Bromo-2-(1-(2-(ethylsulfonyl)ethylamino)ethyl)-7-fluoro-4H-pyrido[1,2-a]pyrimidin-4-one (E4). E3 (222 mg, 0.78 mmol) was dissolved in 5 mL methanol. Triethylamine (0.11 mL, 0.78 mmol) was added followed by ethyl vinyl sulfone (0.082 mL, 0.78 mmol). The reaction was heated at 50° C. overnight. After removal of methanol, the mixture was purified by chromatography with 1:1 dichloromethane:ethyl acetate then gradient methanol in dichloromethane (2% to 4% to 6%) to give 318 mg E4 as an oil.

N-(1-(3-Bromo-7-fluoro-4-oxo-4H-pyrido[1,2-a]pyrimidin-2-yl)ethyl)-N-(2-(ethylsulfonyl)ethyl)-2-(4-fluoro-3-(trifluoromethyl)phenyl)acetamide (E5). To a flask with E4 (310 mg, 0.77 mmol) was added 2-(4-fluoro-3-(trifluoromethyl)phenyl)acetic acid (187 mg, 0.84 mmol), EDC (440 g, 2.3 mmol), HOBt (52 mg, 0.38 mmol), followed by 14 mL of anhydrous DMF and N-methyl morpholine (0.25 mL, 2.3 mmol). The reaction was stirred at room temperature overnight and worked up with ethyl acetate and water. Column chromatography with gradient ethyl acetate/dichloromethane (3:1 to 2:1 to 1:1) gave 460 mg E5 as an yellow foamy solid.

N-(1-(3-(4-Cyanophenyl)-7-fluoro-4-oxo-4H-pyrido[1,2-a]pyrimidin-2-yl)ethyl)-N-(2-(ethylsulfonyl)ethyl)-2-(4-fluoro-3-(trifluoromethyl)phenyl)acetamide (7.01). E5 (66.8 mg, 0.11 mmol), 4-cyanophenyl boronic acid (20 mg, 0.13 mmol), and Pd(dppf)2Cl2 (9 mg, 0.01 mmol) was added into a 10 mL CEM microwave tube, followed by THF (1.1 mL) and sodium carbonate (0.55 mL, 2M). The mixture was reacted by microwave at 150° C. for 10 min and then partitioned between water and ethyl acetate. Column chromatography with gradient dichloromethane:ethyl acetate (4:1 to 3:1 to 2:1) afforded 38 mg 7.01 as a yellow foamy solid in a racemic mixture. Additional amounts of 7.01 were prepared and combined.

(R)-N-(1-(3-(4-cyanophenyl)-7-fluoro-4-oxo-4H-pyrido[1,2-a]pyrimidin-2-yl)ethyl)-N-(2-(ethylsulfonyl)ethyl)-2-(4-fluoro-3-(trifluoromethyl)phenyl)acetamide (7.02). Compound 7.01 was loaded onto Chiral HPLC (AD-H) column with 40% isopropanol in hexanes as eluent for separation of isomers. Isomer 7.02 was obtained in 29 mg as a white foamy solid. The product existed as a pair of rotamers (1:0.43) by NMR. $^1$H NMR (CDCl$_3$, 500 MHz): δ 8.98 (m, 1.4H), 7.93 (m, 1H), 7.87 (d, J=8.3, 2H), 7.81 (m, 2H), 7.70 (m, 1.3H), 7.53 (d, J=8.1, 2.4H), 7.45 (m, 1H), 7.14 (m, 1.5H), 7.06 (m, 2H), 5.52 (q, J=7.2, 0.43H), 5.00 (q, J=6.7, 1H), 4.39 (m, 0.45H), 4.16 (m, 1.44H), 3.97 (m, 1H), 3.81 (q, J=11.5, 0.89H), 3.41 (m, 1.88H), 3.03 (m, 6H), 1.56 (d, J=6.8, 3H), 1.46 (t, J=7.5, 1.6H), 1.40 (t, J=7.5, 3H), 1.36 (d, J=7.3, 1.4H). (LC/MS (ES): 633.4 [M+H].

5.8. Example 8

Compound 8.01 was synthesized as shown in Scheme F. Reaction conditions were similar to those described in detail in Section 5.5.

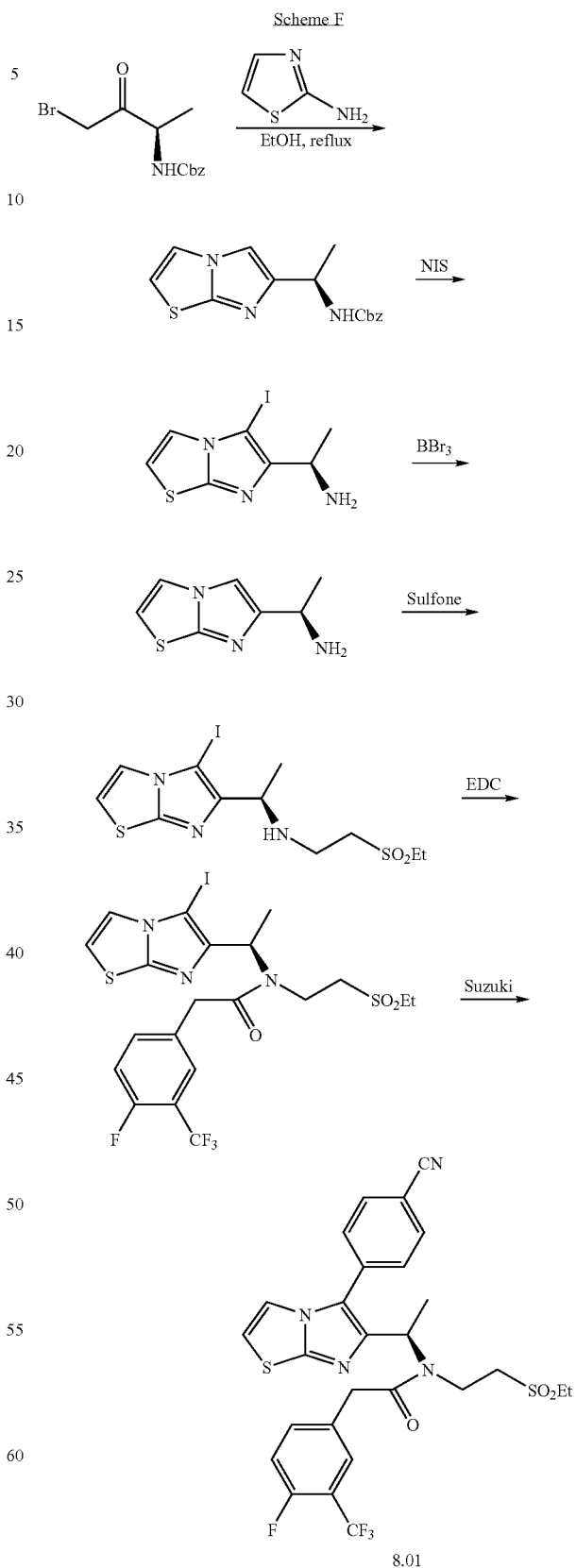

Scheme F

Compound 8.01. LC/MS (ES): 592.0 [M+H]

5.9. Example 9
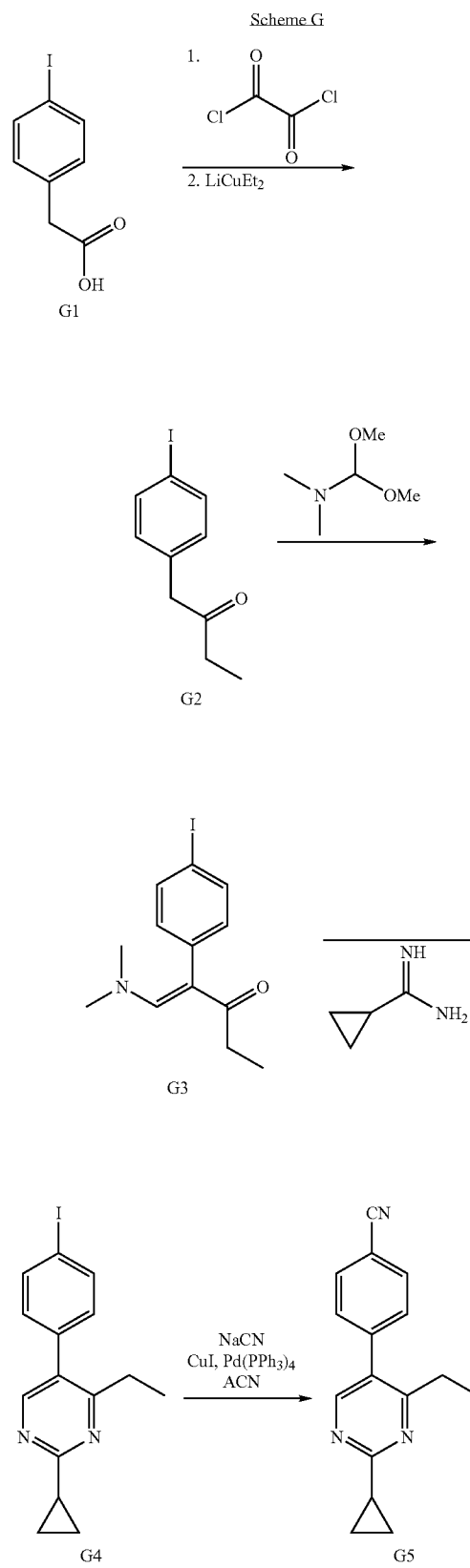
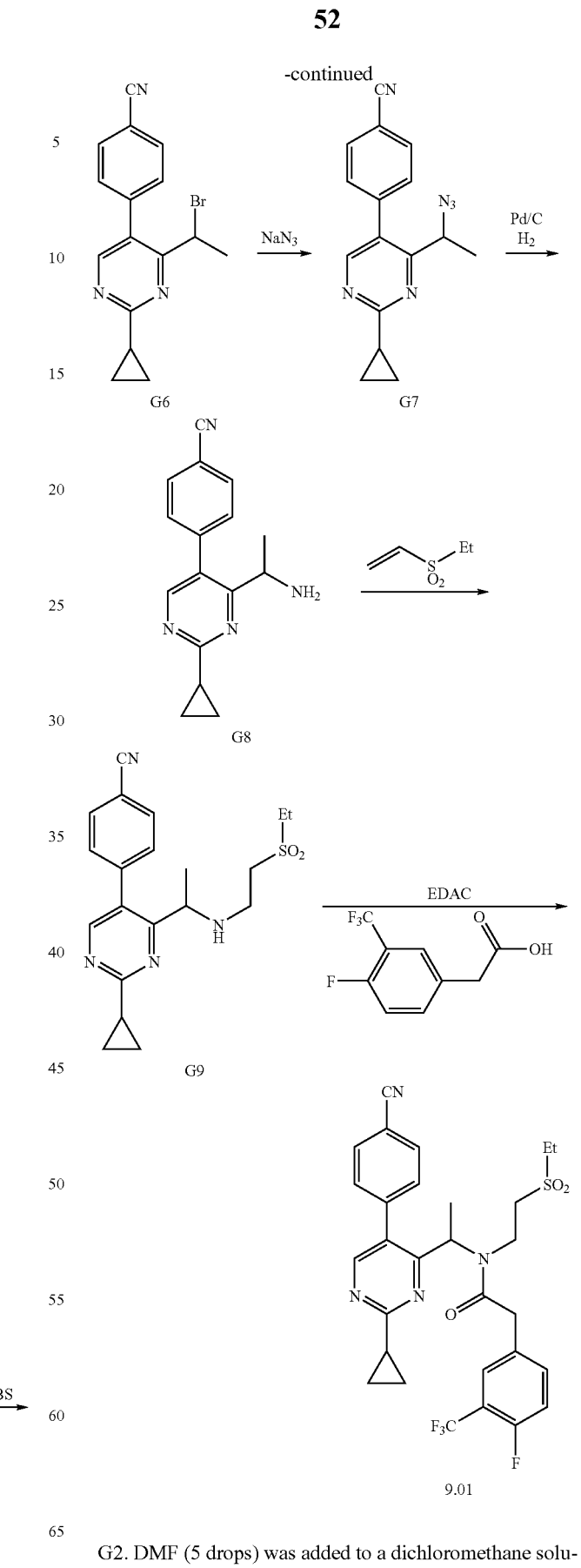
G2. DMF (5 drops) was added to a dichloromethane solution (30 mL) containing acid G1 (4.02 g, 15 mmol) and oxalyl chloride (1.61 mL, 18 mmol) at room temperature. After stirring for 1 h., excess dichloromethane was removed using reduced pressure. The remaining residue was dissolved in a dry THF and was added to a THF solution containing ethyl cuprate (23 mmol) at −20° C. After 20 min., a saturated copper sulfate solution was then added at −20° C., and the mixture was warmed to room temperature. The resulting solution was extracted with ethyl acetate, dried over sodium sulfate, and concentrated. The remaining residue was purified on silica eluting with 30% ethyl acetate/hexane solution to give 2.29 g (56% yield) of ketone G2: ESI (MH$^+$) m/z 275.

G3. DMF dimethyl acetal (1.13 mL, 8.5 mmol) and ketone G2 (2.32 g, 8.5 mmol) were heated together in a DMF solution (10 mL) at 60° C. for 1.5 h. After cooling, the solution was partitioned with ethyl acetate and water. The organic layer was then washed with brine, dried over sodium sulfate, and concentrated. The residue was purified on silica eluting with 50% ethyl acetate/hexane solution. Similar fractions were pooled and concentrated to give 1.83 g (65% yield) of G3: ESI (MH$^+$) m/z=330.

G4. Sodium hydride (186 mg, 4.7 mmol) was added to an ethanolic solution containing intermediate G3 (1.02 g, 3.1 mmol) and cyclopropanecarboxamidine (0.56 g, 4.7 mmol). The resulting mixture was heated at reflux for 16 h. then concentrated. The remaining residue was purified on silica eluting with 50% ethyl acetate/hexane solution. Similar fractions were pooled and concentrated to give 0.62 g (58% yield) of pyrimidine G4: ESI (MH$^+$) m/z 351.

G5. Argon flushed acetonitrile (25 mL) was added to a flask containing pyrimidine G4 (0.62 g, 1.8 mmol), sodium cyanide (174 mg, 3.6 mmol), palladiumtetrakistriphenylphosphine (103 mg, 0.09 mmol) and copper iodide (34 mg, 0.2 mmol) under an atmosphere of argon. The resulting mixture was heated at reflux for 5 hours then concentrated. The remaining residue was purified on silica eluting with a 55% ethyl acetate/hexane solution to give 0.4 g (89% yield) of pyrimidine G5: ESI (MH$^+$) m/z 250.

G6. AIBN (50 mg) was added to a carbon tetrachloride solution containing pyrimidine G5 (0.4 g, 1.6 mmol) and NBS (0.29 g, 1.6 mmol) and heated at reflux for 7 h. The mixture was then cooled to room temperature and partitioned with water. The organic layer was then washed with brine, dried over sodium sulfate, and concentrated. This material was used in the next step without further purification: ESI (MH$^+$) m/z 328.

G7. Sodium azide (0.1 g, 1.6 mmol) and bromide G6 (1.6 mmol) were mixed in DMF (10 mL) and heated at 80° C. for 2 h. After heating, the solution was partitioned with ethyl acetate and water. The organic layer was then washed with brine, dried over sodium sulfate, and concentrated to give azide G7. This material was used in the next reaction without further purification: ESI (MH$^+$) m/z 291.

G8. Azide G7 (1.6 mmol) was hydrogenated over 10% Pd/C (50 mg) in ethanol (25 mL) under an atmosphere of hydrogen (atmospheric pressure) for 15 min. The suspension was then filtered through a cake of celite and concentrated to give amine G8. This material was used in the next reaction without further purification: ESI (MH$^+$) m/z 265.

G9. Vinyl sulfone (0.17 mL, 1.6 mmol), triethylamine (0.22 mL, 1.6 mmol), and amine G8 (1.6 mmol) were dissolved in a methanol/water solution (1:1, 20 mL) and heated to 50° C. for 4 h. The solvent was then removed under reduced pressure, and the remaining residue G9 was used in the next step without purification: ESI (MH$^+$) m/z 385.

Compound 9.01. Intermediate G9 (1.6 mmol), 2-(4-fluoro-3-(trifluoromethyl)phenyl)acetic acid (355 mg, 1.6 mmol), EDAC (368 mg, 1.9 mmol), and triethylamine (0.33 mL, 2.4 mmol) were mixed in dichloromethane (10 mL) for 4 h. Excess solvent was then removed and the resulting material was purified on silica eluting with a 70% ethyl acetate/hexane solution. Similar fractions were pooled and concentrated to give 9.01: $^1$H NMR (500 MHz, CDCl$_3$) δ 8.42 (s, 0.5H), 8.31 (s, 0.5H), 7.83 (d, J=8 Hz, 1H), 7.77 (d, J=8 Hz, 1H), 7.58 (d, J=8 Hz, 1H), 7.41-7.48 (m, 2H), 7.09-7.16 (m, 1H), 7.05 (m, 1H), 5.60 (q, J=7 Hz, 0.5H), 5.03 (q, J=7 Hz, 0.5H), 4.20 (m, 0.5H), 4.06-4.12 (m, 1H), 3.88 (m, 1H), 3.41 (m, 0.5H), 3.22 (m, 0.5H), 3.11 (m, 1.5H), 3.01 (m, 2H), 2.89 (d. J=15 Hz, 0.5H), 2.36 (m, 0.5H), 2.18 (m, 0.5H), 1.51 (d, J=7 Hz, 1.5H), 1.43 (t, J=7 Hz, 1.5H), 1.37 (t, J=7 Hz, 1.5H), 1.28 (t, J=7 Hz, 1.5H), 1.17-1.26 (m, 5H), 1.07 (m, 2H), 0.89 (m, 1H); Analytical HPLC Method A @ 254 nm: rt=7.492 min.; ESI (MH$^+$) m/z 589.

5.10. Example 10

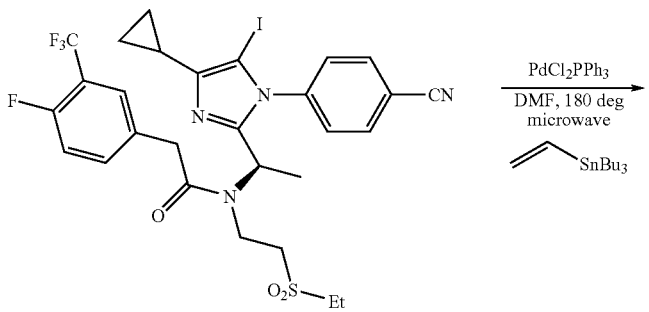

Scheme H 10.01

-continued

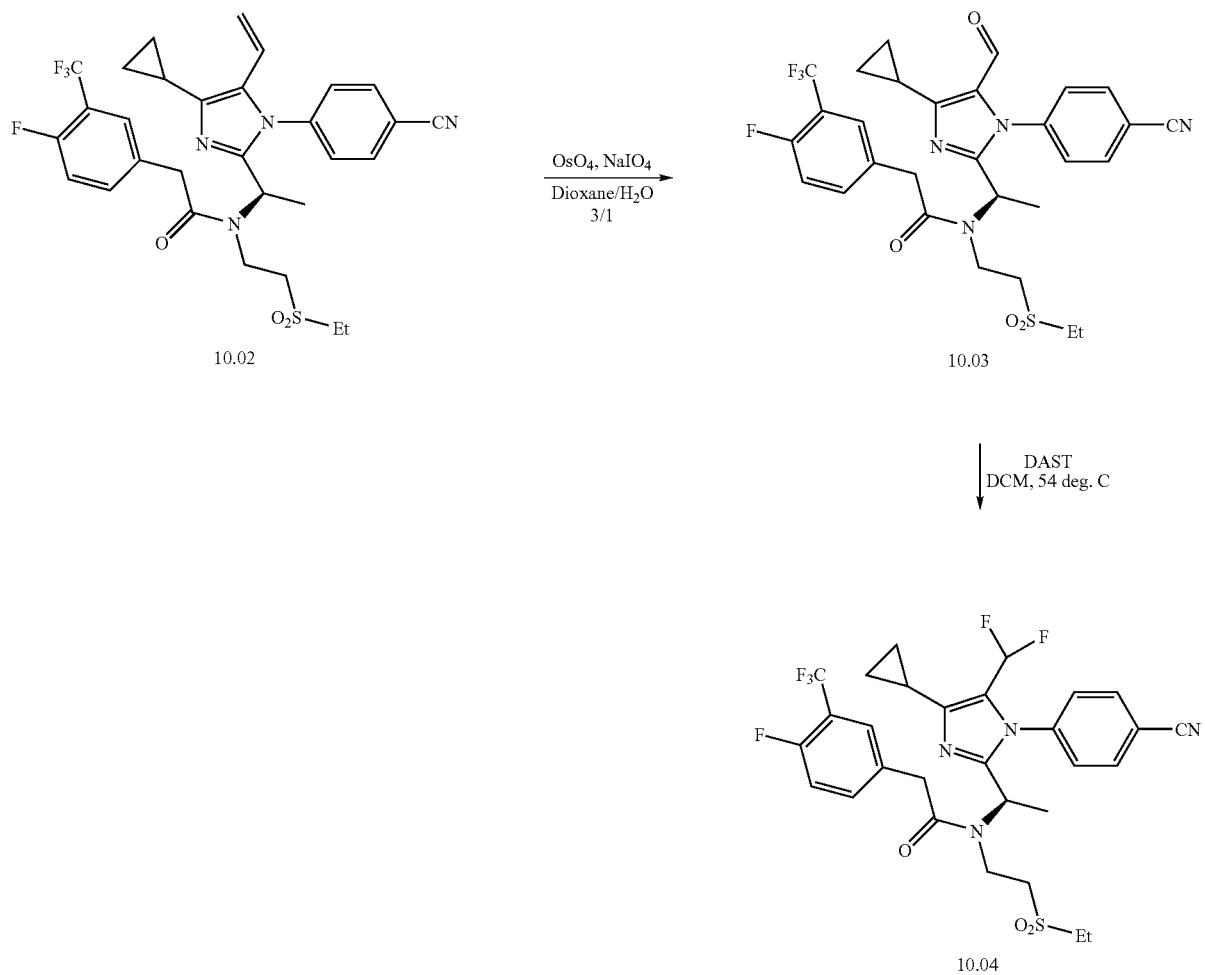

Compound 10.01. Compound 10.01 was synthesized according to the generic scheme for the synthesis of imidazoles described in FIG. 8 in International Publication WO 02/083143 with modification to form a p-cyanophenyl group in place of a p-methoxyphenyl group.

Compound 10.02. PdCl$_2$PPh$_3$ (19 mg, 0.02 mmol) was added to dry, degassed DMF solution (2 mL) containing iodide 10.01 (380 mg, 0.5 mmol) and tributyl(vinyl)tin (206 mg, 0.6 mmol) under an atmosphere of argon. The mixture was then microwaved in a seal tube at 180° C. for 6 minutes. After heating, excess DMF was removed using reduced pressure, and the remaining residue was purified on silica eluting with 50% hexane/ethyl acetate solution. Similar fractions were pooled and concentrated to give 10.02 as white solid: Analytical HPLC Method A@254 nm: rt=6.626 min.; ESI (MH$^+$) m/z 603.

Compound 10.03. Compound 10.02 (369 mg, 0.6 mmol) was dissolved in a 3:1 dioxane/water solution (10 mL) containing OsO$_4$ (catalytic amount). After 10 min. the solution had turned dark in color, and an aqueous solution containing NaIO$_4$ (260 mg, 1.2 mmol) was added. Within 2 h. the reaction had completed, and the mixture was partitioned with water (50 mL) and ethyl acetate (50 mL). The organic layer was then washed with a saturated solution of Na$_2$S$_2$O$_3$, followed by brine, dried over Na$_2$SO$_4$, and concentrated to give 10.03. This material was used in the next step without purification: Analytical HPLC Method A @ 254 nm: rt=7.279 min.; ESI (MH$^+$) m/z 605.

Compound 10.04. In a sealed tube, DAST (194 mg, 1.2 mmol) was mixed with 10.03 in dichloromethane (2 mL) at 54° C. for 8 hours. The solvent was then removed using evaporation, and the remaining residue was purified using preparative HPLC (C18 column, 10%-90% acetonitrile/water gradient). 10.04: $^1$H NMR (Compound exists as a mixture of conformational isomers) (500 MHz, CDCl$_3$) δ 7.89 (s, 1H) 7.76 (m, 1H), 7.45 (m, 3H), 7.16 (m, 1H), 7.10 (m, 1H), 6.23 (t, J=50.9 Hz, 1H), 5.47 (q, J=6.81 Hz, 0.6H), 4.72, (m, 0.4H), 3.92 (m, 1H), 3.67 (m, 2H), 3.18 (m, 1H), 3.02 (m, 3H), 2.77 (m, 1H), 1.88 (m, 1H), 1.48 (d, J=6.90 Hz, 1H), 1.43 (t, J=7.46 Hz, 2H), 1.39 (m, 4H), 1.07 (m, 1H), 0.89-0.99 (m, 4H); Analytical HPLC Method A @ 254 nm: rt=7.357 min.; ESI (MH$^+$) m/z 627.

5.11. Example 11

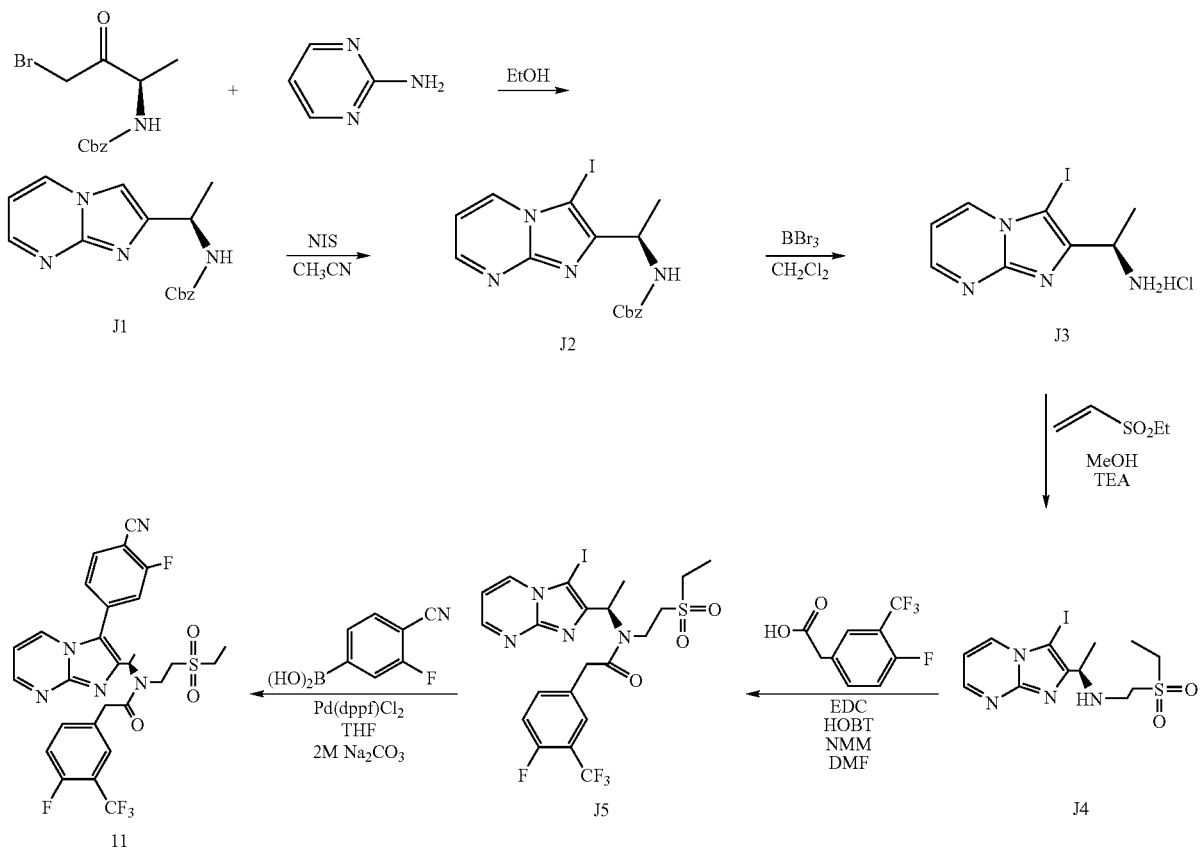

Scheme J

J1. A mixture of (R)-benzyl 4-bromo-3-oxobutan-2-ylcarbamate (5.00 g, 16.7 mmol) and pyrimidin-2-amine (1.58 g, 16.6 mmol) in EtOH (50 mL) was refluxed for 16 hours. The EtOH was removed and the resulting oil was diluted with EtOAc and saturated $NaHCO_3$. Precipitated yellow solids were filtered off (11.42 g; MS (ES): 297 [M+H]). The organic layer was separated and set aside. The aqueous layer was washed with EtOAc three times and the combined organic layers were dried over $Na_2SO_4$ and concentrated in vacuo. Crude material was purified by flash chromatography on silica gel using (2:1) $EtOAc/CH_2Cl_2$, followed by a gradient elution of 2-4% $MeOH/CH_2Cl_2$. This material was further purified by recrystallization ((1:9) MeOH/EtOAc). Obtained 0.85 g J1 as a yellow solid. When combined with additional preparations of J1 as described above, 2.27 g of J1 was isolated (46% yield).

J2. NIS (1.98 g, 8.36 mmol, 95%$_{wt}$ purity) was added to J1 (2.27 g, 7.66 mmol) in $CH_3CN$ (100 mL) and the mixture was stirred at room temperature for 4 hours. The solvent was removed in vacuo, and the remaining residue was purified by flash chromatography on silica gel using (2:1) $EtOAc/CH_2Cl_2$, followed by (3:1) $EtOAc/CH_2Cl_2$ to afford 3.00 g (93% yield) of J2 as a yellow solid.

J3. J2 (2.76 g, 6.53 mmol) was dissolved in $CH_2Cl_2$ (220 mL) and cooled to $-10°$ C. $BBr_3$ (1M in $CH_2Cl_2$, 19.5 mL, 19.5 mmol) was then added dropwise, and the mixture was stirred at $-10°$ C. for 1 hour. The cooling bath was removed and the reaction was warmed to room temperature over 30 minutes. After another hour of stirring at room temperature, the reaction was cautiously quenched with sat. $NaHCO_3$. The reaction mixture was then treated 1N HCl in $Et_2O$ to form the salt of J3. Precipitated solids were filtered off and set aside (MS (ES): 289 [M+H]). The aqueous layer was then separated from the organic and extracted with (3:7) $IPOH/CHCl_3$ (8 times). The combined organic extracts were dried over $Na_2SO_4$ and concentrated in vacuo. The yellow solids that were obtained were combined with the solids that were filtered off previously to give 1.75 g (82% yield) as the HCl salt of J3. This material was used directly, without further purification.

J4. J3 (1.75 g, 5.40 mmol) was dissolved in MeOH (40 mL) to which TEA (1.5 mL, 10.8 mmol) was added, followed by ethyl vinyl sulfone (1.2 mL, 11.5 mmol). The reaction was then heated at $50°$ C. for 4.5 hours. After cooling to room temperature, the solvent was evaporated to afford 2.30 g of J4 as a yellow foam.

J5. J4 (2.20 g, 5.39 mmol) was azeotroped with toluene twice, and then dissolved in DMF (35 mL). To the solution was then added 4-fluoro-3-(trifluoromethyl)phenylacetic acid (1.70 g, 7.66 mmol), EDC (3.15 g, 16.4 mmol), HOBT (380 mg, 2.81 mmol), and NMM (1.80 mL, 16.4 mmol), in that order. The resulting mixture was then stirred at room temperature for 16 hours. The solvent was removed and the crude reaction mixture was purified by flash chromatography on silica gel using 2% MeOH/CH$_2$Cl$_2$ to afford 2.81 g (85% yield over two steps) of J5 as a yellow solid.

Compound 11. J5 (79.00 mg, 0.129 mmol) and 4-cyano-3-fluorophenylboronic acid (26.00 mg, 0.158 mmol) were dissolved in THF (1 mL). To this solution was added Pd(dppf)Cl$_2$ (11.00 mg, 0.013 mmol) and 2M Na$_2$CO$_3$ (0.5 mL). The reaction mixture was heated in the microwave for 10 minutes at 150° C. The solvent was evaporated and the crude reaction mixture was purified by flash chromatography on silica gel with a gradient elution of 1-2% MeOH/CH$_2$Cl$_2$ to afford 57.6 mg (74% yield) of 11 as an orange foam. $^1$H NMR (400 MHz, CDCl$_3$; mixture of rotomers): δ 8.63 (m, 0.75H), 8.40 (m, 0.45H), 8.23 (m, 0.18H), 7.84 (m, 0.72H), 7.45 (m, 3.42H), 7.28 (m, 1.13H), 7.16 (m, 1.22H), 6.99 (m, 1.17H), 5.99 (m, 0.60H), 5.29 (m, 0.40H), 4.15 (m, 1.26H), 3.91 (m, 0.83H), 3.82 (m, 1.35H), 3.66 (s, 0.65H), 3.48 (s, 0.39H), 3.33 (m, 1.68H), 3.05 (m, 3.55H), 1.60 (m, 4.38H), 1.44 (m, 2.36H), 1.29 (m, 1.51H). MS (ES): 606 [M+H].

5.12. Example 12

The following example describes the synthesis of 12.01 and 12.02.

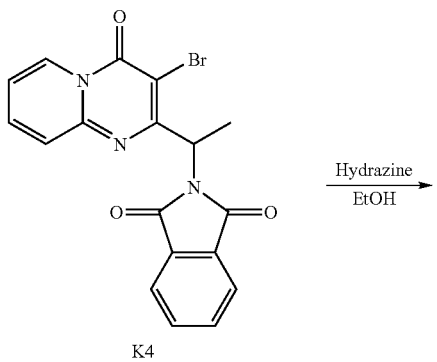

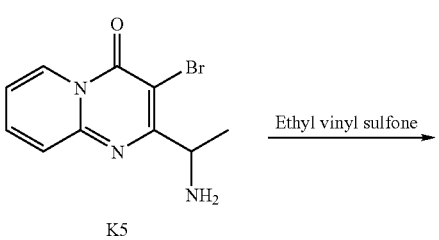

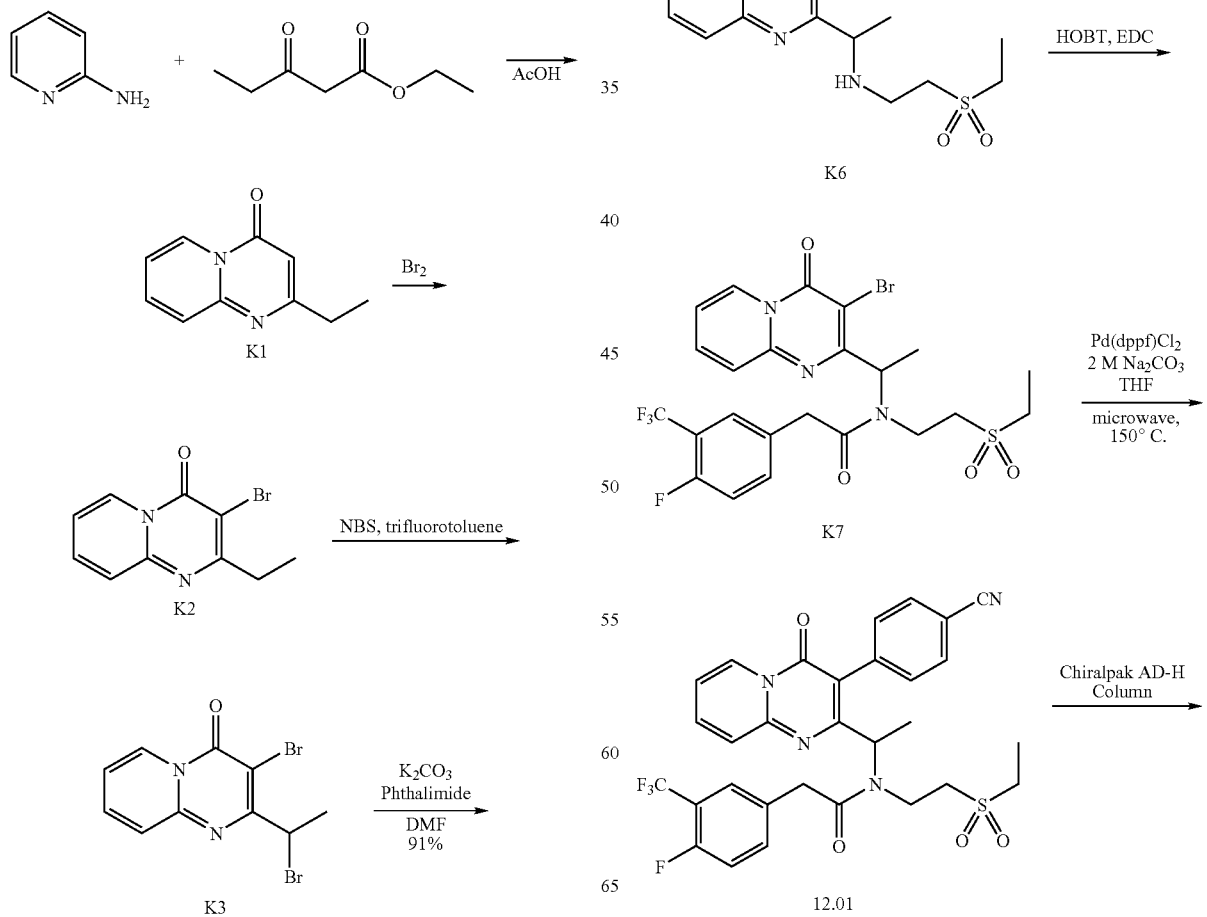

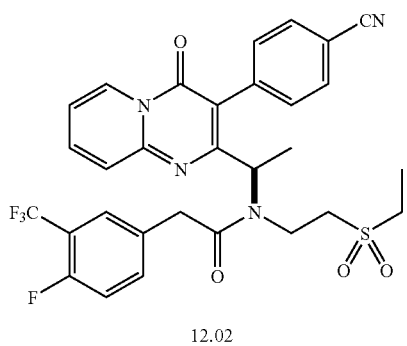

12.02

3-Bromo-2-ethyl-4H-pyrido[1,2-a]pyrimidin-4-one (K2). A solution of aminopyridine (32.6 g, 347 mmol), ethyl propionylacetate (50.0 g, 347 mmol) and AcOH (250 ml) were heated at reflux overnight. The solution was cooled to room temperature and was added additional 250 ml of acetic acid. The reaction was cooled in a water batch. The resulting solution was treated with 17.8 ml of bromine drop-wise over approximately 10 min. After stirring at room temperature for 2 hours. The precipitate was filtered. The solid was washed with ether two times and 40% ethyl acetate-hexanes once and dried in vacuum to give 31.5 g K2 as the first crop. The filtrate was concentrated to a small volume and the precipitate was filtered. The solid was washed with ether two times and 40% ethyl acetate-hexanes once and dried in vacuum to give 47.1 g of K2 as the second crop. Combined yield: 89.9% over two steps.

3-Bromo-2-(1-bromoethyl)-4H-pyrido[1,2-a]pyrimidin-4-one (K3). K2 (16.4 g, 64.8 mmol), NBS (11.5 g, 64.8 mmol), and α,α,α-trifluorotoluene (160 ml) was heated in an oil bath at 90° C. for 3 days. The reaction mixture was cooled and partitioned between EtOAc (1 L) and H$_2$O (1 L). The phases were separated and the organic layer was washed with H$_2$O (4×750 ml). The organic layer was collected, concentrated to a slurry, and filtered to yield a tan solid (12.5 g) and a dark red filtrate. The filtrate was concentrated further, treated with methanol, and filtered again to yield a brown solid K3 (1.91 g). Combined yield: 67%. LC-MS (+esi, M+H$^+$=330.9).

2-(1-(3-Bromo-4-oxo-4H-pyrido[1,2-a]pyrimidin-2-yl)ethyl)isoindoline-1,3-dione (K4). K3 (3.2 g, 9.6 mmol), K$_2$CO$_3$ (0.77 g, 5.3 mmol), and phthalimide (1.41 g, 9.6 mmol) were ground together in a crystallization dish. The resulting solid mixture was transferred to a round bottom flask and dried at 80° C. under vacuum for ~1 h. DMF (50 ml) was added and the mixture was heated in an oil bath at 80° C. for ~3 h. The reaction mixture was allowed to cool overnight and was then treated with H$_2$O (50 ml) and filtered. The solid was dried at 60° C. under vacuum for ~1 h. Obtained an off-white solid K4 (3.48 g, 91%). LC-MS (+esi, M+H$^+$=398.0).

2-(1-Aminoethyl)-3-bromo-4H-pyrido[1,2-a]pyrimidin-4-one (K5). K4 (3.48 g, 8.74 mmol), hydrazine hydrate (0.5 ml, 9.61 mmol), and EtOH (80 ml) were heated at reflux overnight. The reaction mixture was allowed to cool to room temperature and then treated with conc. HCl (7.2 ml). The white slurry was heated at reflux for ~1 h. The mixture was cooled to room temp. and the white slurry was filtered. H$_2$O (50 ml) was added to the filtrate and the solution was transferred to a rotavap to remove most of the ethanol in vacuo. The resulting aqueous solution was basified with saturated bicarbonate, saturated with solid sodium chloride, and extracted with EtOAc until little product remained in the aqueous layer. The organics were combined, concentrated in vacuo, and placed on a high vacuum to yield 2.42 g (~100%) of yellow solid K5. LC-MS (+esi, M+H$^+$=268.0).

N-(1-(3-bromo-4-oxo-4H-pyrido[1,2-a]pyrimidin-2-yl)ethyl)-N-(2-(ethylsulfonyl)ethyl)-2-(4-fluoro-3-(trifluoromethyl)phenyl)acetamide (K7). A solution of K5 (2.42 g, 9.02 mmol), ethyl vinyl sulfone (1.03 ml, 9.93 mmol), triethylamine (1.38 ml, 9.93 mmol), methanol (~20 ml), and H$_2$O (~10 ml) were heated at 50° C. overnight. LC-MS indicated starting material remained. Additional ethyl vinyl sulfone (0.5 ml) was added and the solution was heated for another ~6 h. LC-MS indicated a trace of starting material. The reaction mixture was concentrated in vacuo and the resulting residue was partitioned between H$_2$O (100 ml) and EtOAc (100 ml). The aqueous layer was extracted with EtOAc (2×100 ml). The organic extracts were combined and concentrated to an oil containing K6 (4.2 g crude, quantitative). LC-MS (+esi, M+H$^+$=388.0).

The crude oil from above was dissolved in DMF (50 ml). N-methylmorpholine (3 ml, 27.1 mmol), HOBT (609 mg, 4.51 mmol), 4-fluoro-3-(trifluoromethyl)phenylacetic acid (2.20 g, 9.92 mmol), and EDC-HCl (5.19 g, 27.1 mmol) were added to the solution in that order and the mixture was allowed to stir at room temperature overnight. The reaction mixture was partitioned between H$_2$O (500 ml) and EtOAc (500 ml). The organic layer was washed with H$_2$O (2×500 ml), collected, and concentrated to an oil. The oil was dissolved in CH$_2$Cl$_2$ and chromatographed on silica gel (0% EtOAc to 30% EtOAc in CH$_2$Cl$_2$). The desired fractions were combined and concentrated to an oily residue (4.60 g, 86% over 2 steps). Upon dissolving the residue in methanol (50 ml) crystals formed and the resulting slurry was filtered to yield a white solid K7 (3.41 g). LC-MS (+esi, M+H$^+$=592.0).

(R)-N-(1-(3-(4-cyanophenyl)-4-oxo-4H-pyrido[1,2-a]pyrimidin-2-yl)ethyl)-N-(2-(ethylsulfonyl)ethyl)-2-(4-fluoro-3-(trifluoromethyl)phenyl)acetamide (12.02). K7 (300 mg, 0.506 mmol), 4-cyanophenylboronic acid (89 mg, 0.608 mmol), Pd(dppf)Cl$_2$ (40 mg, 0.05 mmol), THF (2 ml) and 2 M Na$_2$CO$_3$ (1 ml, 2 mmol) were mixed in a microwave tube and heated in a CEM microwave for 10 minutes at 150° C. The organic layer was chromatographed on silica gel (1:1 EtOAc:CH$_2$Cl$_2$) and the desired fractions were concentrated to an oil containing 12.01. The oil was dissolved in methanol and resolved via five injections on a Chiralpak AD-H column (2×25 cm, 5μ; 35% IPA:65% Hexane; 12 ml/min). The later eluting enantiomer was collected and concentrated. The resulting oil was dissolved in a minimal amount of CH$_3$CN, treated with H$_2$O, and then freeze-dried to yield a fluffy white solid 12.02 (110 mg, 35%). LC-MS (+esi, M+H$^+$=615.1).

5.13. Example 13

Additional exemplary compounds can be synthesized according to the reaction schemes described above with slight modifications.

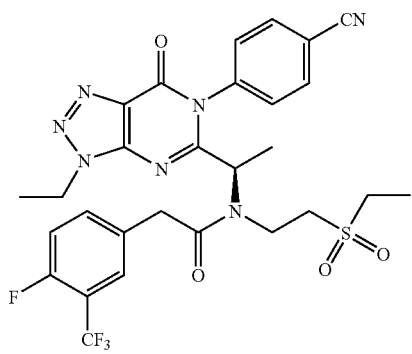
Compound 13.01.
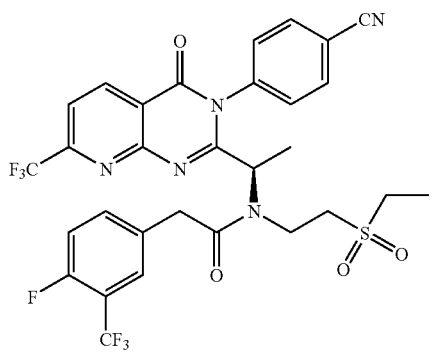
Compound 13.04.
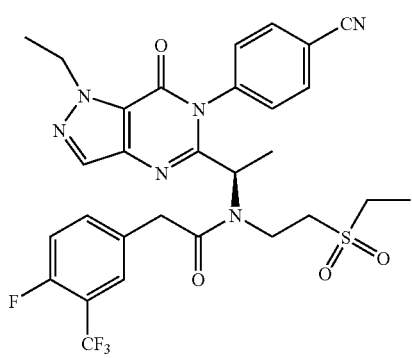
Compound 13.02.
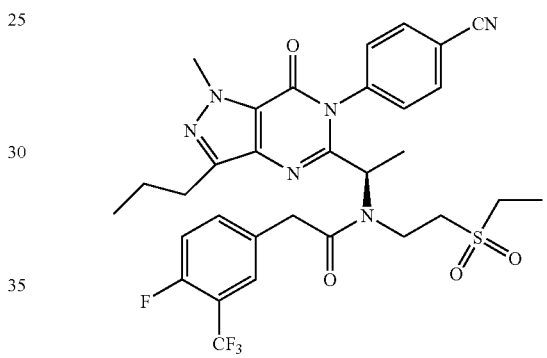
Compound 13.05.
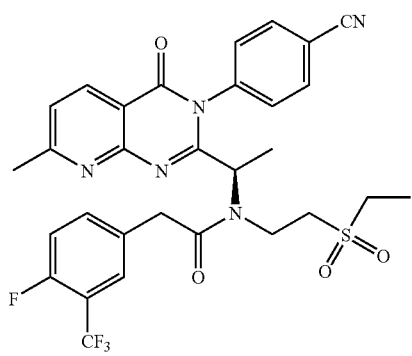
Compound 13.03.
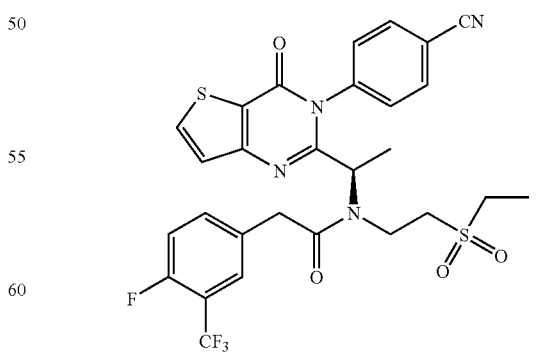
Compound 13.06.

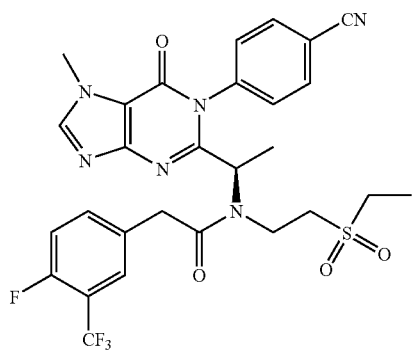
Compound 13.07.
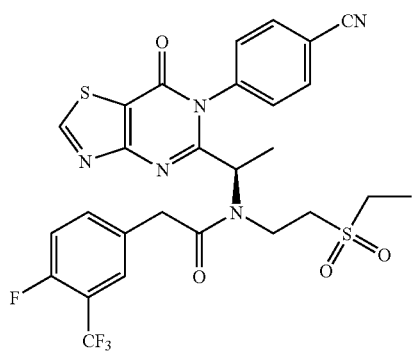
Compound 13.08.
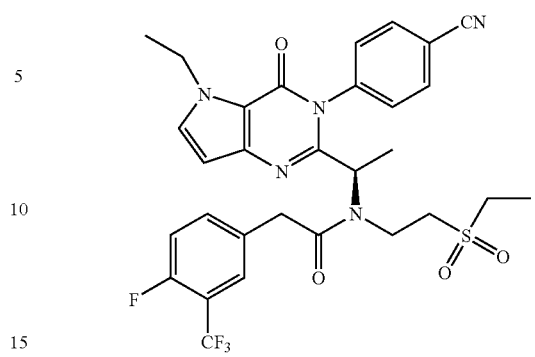
Compound 13.09.
5.14. Example 14
The following examples provided in Table 1 were synthesized following the above synthetic schemes with slight modifications.
TABLE 1
| Example | Molecular Formula | Characterization (Mass) MS + 1 |
|---------|-------------------|-------------------------------|
| 14.01 | Chiral | 613.6 |

TABLE 1-continued
| Example | Molecular Formula | Characterization (Mass) MS + 1 |
|---------|-------------------|-------------------------------|
| 14.02 | 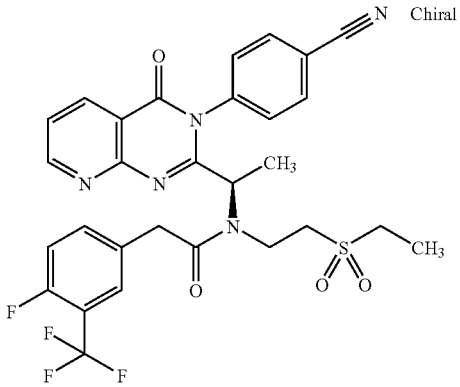 | 616.6 |
| 14.03 | 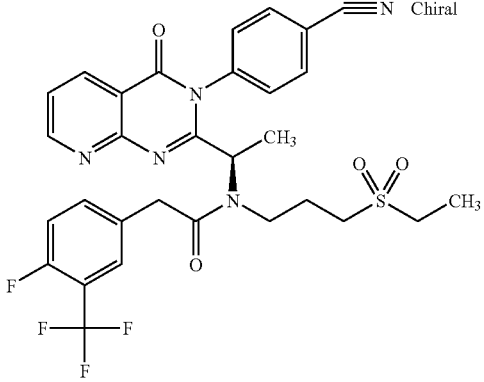 | 630.6 |
| 14.04 | 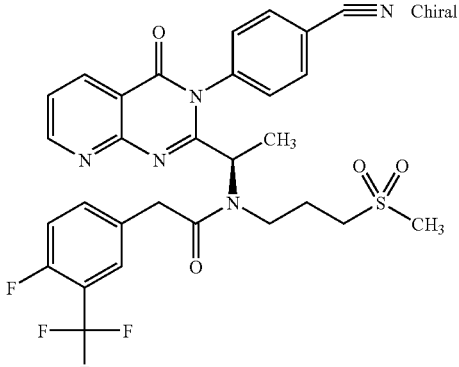 | 616.6 |

TABLE 1-continued

| Example | Molecular Formula | Characterization (Mass) MS + 1 |
|---------|-------------------|-------------------------------|
| 14.05 | Chiral | 577.6 |
| 14.06 | Chiral | 614.6 |
| 14.07 | | 613.2 |

TABLE 1-continued
| Example | Molecular Formula | Characterization (Mass) MS + 1 |
|---|---|---|
| 14.08 | 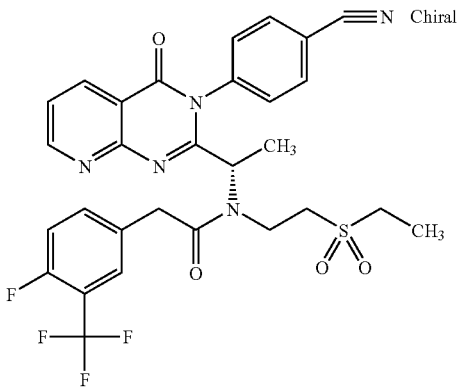 Chiral | 616.6 |
| 14.09 | 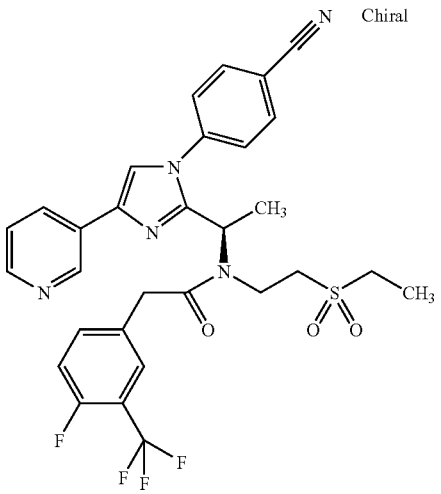 Chiral | 614.6 |
| 14.10 | 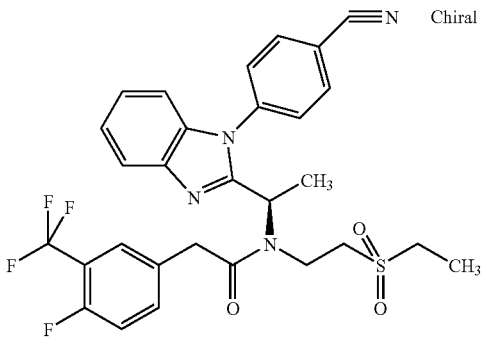 Chiral | 587.6 |

TABLE 1-continued

| Example | Molecular Formula | Characterization (Mass) MS + 1 |
|---|---|---|
| 14.11 | [structure, Chiral] | 593.7 |
| 14.12 | [structure, Chiral] | 612.1 |
| 15.01 | [structure, Chiral] | |
| 16.01 | [structure, Chiral] | |

TABLE 1-continued
| Example | Molecular Formula | | Characterization (Mass) MS + 1 |
|---|---|---|---|
| 17.01 | 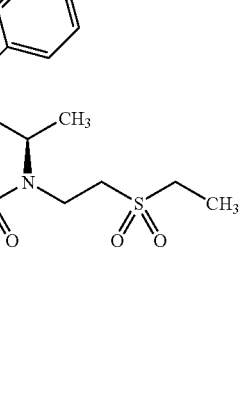 | Chiral | 579.6 |
| 17.02 | 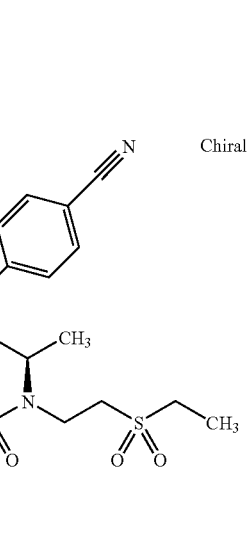 | Chiral | 591.6 |
| 17.03 | 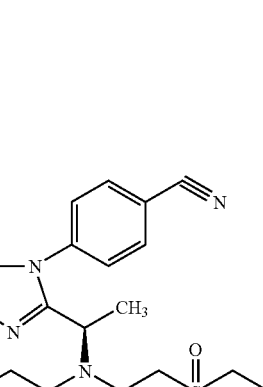 | Chiral | 612.1 |

TABLE 1-continued

| Example | Molecular Formula | Characterization (Mass) MS + 1 |
|---|---|---|
| 17.04 | Chiral | 602.6 |
| 18 | Chiral | |
| 19 | Chiral | 703.5 |
| 20 | Chiral | 603.7 |

TABLE 1-continued

| Example | Molecular Formula | Characterization (Mass) MS + 1 |
|---|---|---|
| 21 | (structure) | 607.6 |
| 22 | (structure) | 605.7 |
| 23 | (structure) | 666.6 |
| 24 | (structure) | 616.6 |

TABLE 1-continued

| Example | Molecular Formula | Characterization (Mass) MS + 1 |
|---------|-------------------|-------------------------------|
| 25 | | 616.6 |
| 26 | | 616.6 |
| 27 | | 614.6 |
| 28 | | 605.6 |

TABLE 1-continued
| Example | Molecular Formula | Characterization (Mass) MS + 1 |
|---|---|---|
| 29 | 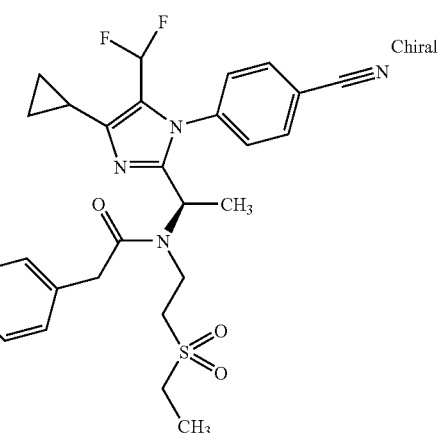 | 627.6 |
| 30 | 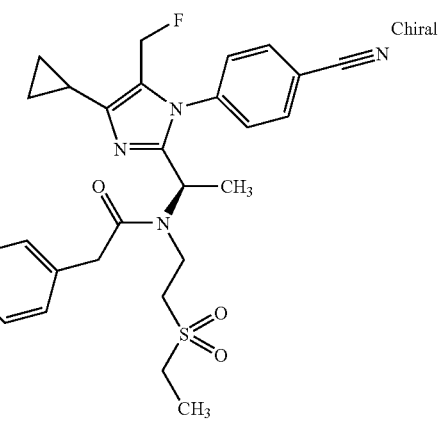 | 609.6 |
| 31 | 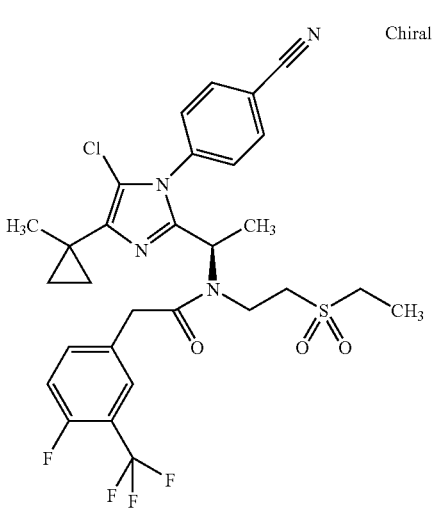 | 626.1 |

TABLE 1-continued
| Example | Molecular Formula | Characterization (Mass) MS + 1 |
|---|---|---|
| 32 | 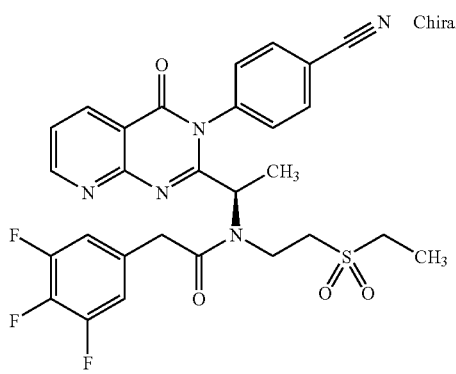 | 584.6 |
| 33 | 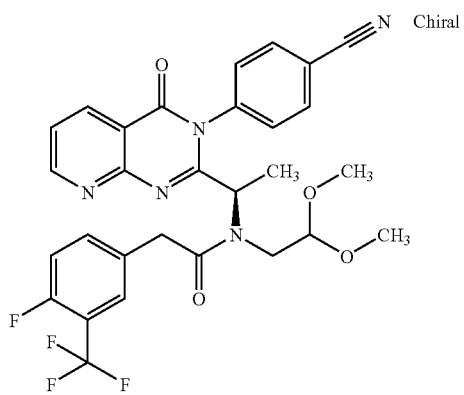 | 584.5 |
| 34 | 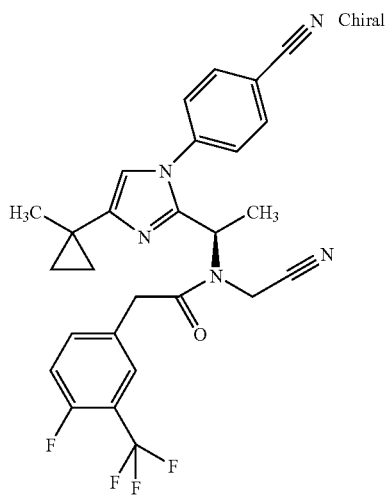 | 510.5 |

TABLE 1-continued
| Example | Molecular Formula | | Characterization (Mass) MS + 1 |
|---|---|---|---|
| 35 | 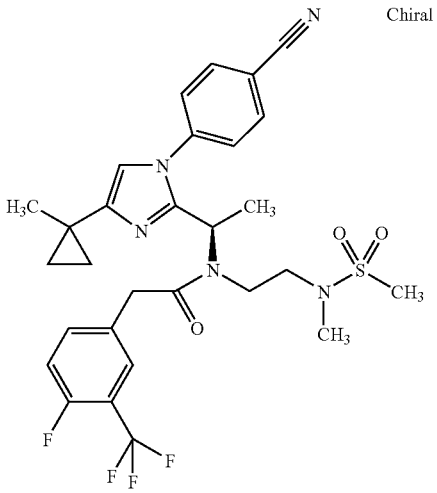 | Chiral | 606.7 |
| 36 | 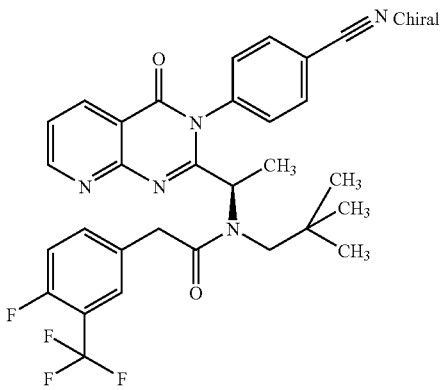 | Chiral | 566.6 |
| 37 | 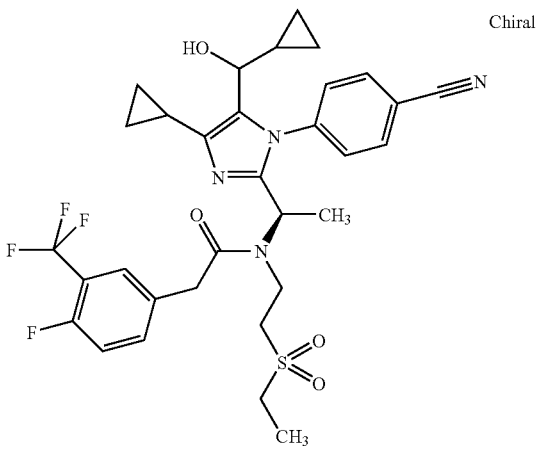 | Chiral | 647.7 |

TABLE 1-continued
| Example | Molecular Formula | | Characterization (Mass) MS + 1 |
|---|---|---|---|
| 38 | 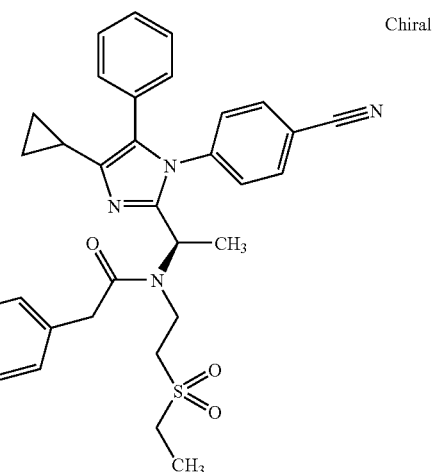 | Chiral | 653.7 |
| 39 | 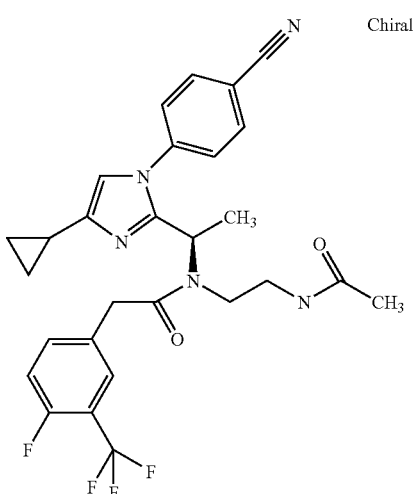 | Chiral | 542.5 |
| 40 | 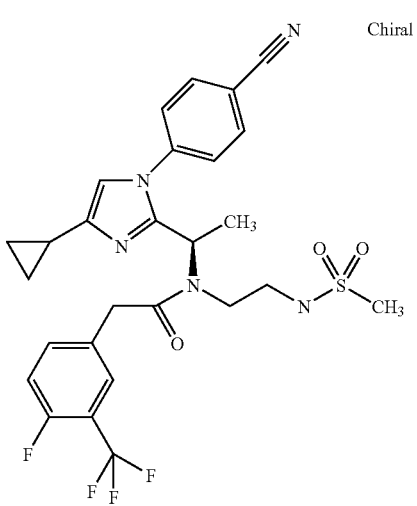 | Chiral | 578.6 |

TABLE 1-continued

| Example | Molecular Formula | Characterization (Mass) MS + 1 |
|---------|-------------------|-------------------------------|
| 41 | | 593.6 |
| 42 | | 596.6 |
| 43 | | 580.6 |
| 44 | | 610.6 |

TABLE 1-continued

| Example | Molecular Formula | Characterization (Mass) MS + 1 |
|---|---|---|
| 45 | (structure) | 612.7 |
| 46 | (structure) | 628.6 |
| 47 | (structure) | 644.7 |
| 48 | (structure) | 645.6 |

TABLE 1-continued
| Example | Molecular Formula | Characterization (Mass) MS + 1 |
|---|---|---|
| 49 | 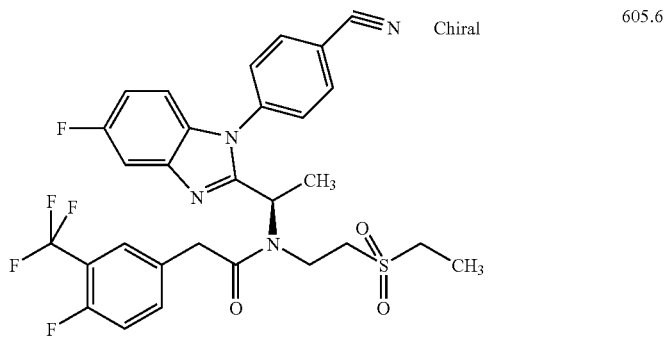 | 605.6 |
| 50 | 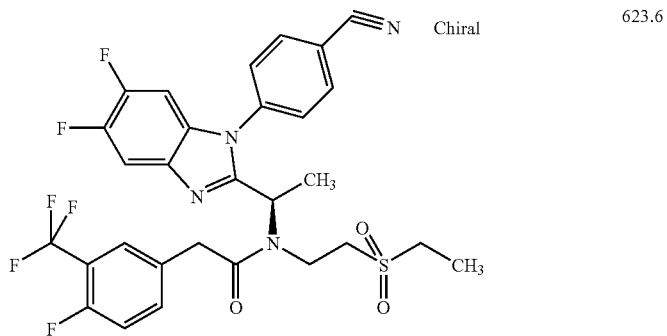 | 623.6 |
| 51 | 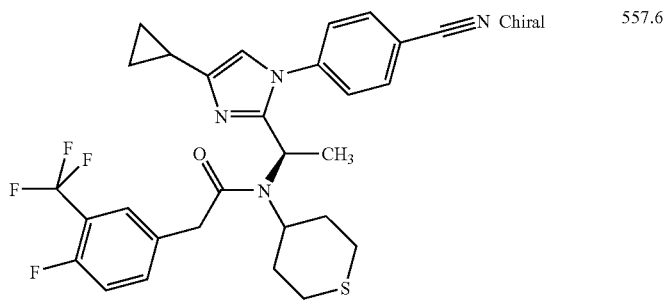 | 557.6 |
| 52 | 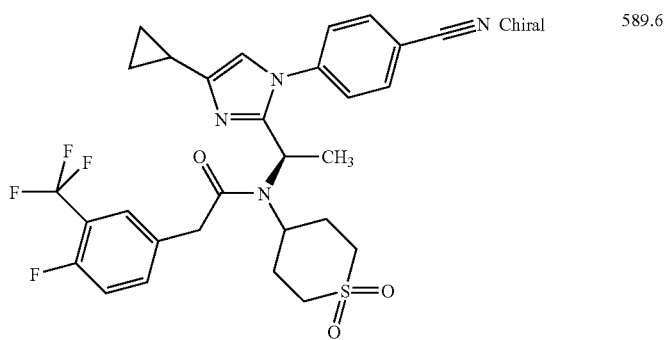 | 589.6 |

TABLE 1-continued

| Example | Molecular Formula | Characterization (Mass) MS + 1 |
|---|---|---|
| 53 | | 598.6 |
| 54 | | 630.6 |
| 55 | | 646.6 |

TABLE 1-continued

| Example | Molecular Formula | Characterization (Mass) MS + 1 |
|---|---|---|
| 56 | Chiral | 647.7 |
| 57 | Chiral | 610.6 |
| 58 | Chiral | 642.6 |
| 59 | Chiral | 598.6 |

TABLE 1-continued
| Example | Molecular Formula | | Characterization (Mass) MS + 1 |
|---|---|---|---|
| 60 | 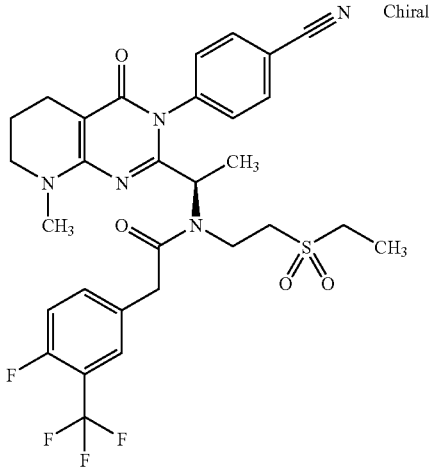 | Chiral | 634.7 |
| 61 | 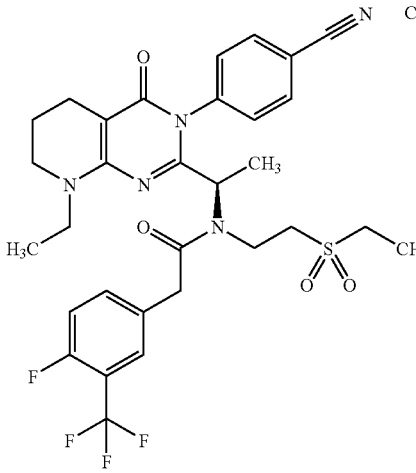 | Chiral | 648.7 |
| 62 | 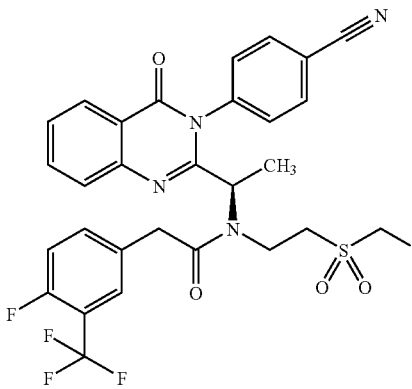 | Chiral | 615.6 |

TABLE 1-continued

| Example | Molecular Formula | Characterization (Mass) MS + 1 |
|---------|-------------------|-------------------------------|
| 63 | | 595.6 |
| 64 | | 609.7 |
| 65 | | 641.7 |

TABLE 1-continued

| Example | Molecular Formula | Characterization (Mass) MS + 1 |
|---------|-------------------|-------------------------------|
| 66 | (structure) | 629.6 |
| 67 | (structure) | 643.7 |
| 68 | (structure) | 655.7 |

TABLE 1-continued
| Example | Molecular Formula | Characterization (Mass) MS + 1 |
|---|---|---|
| 69 | 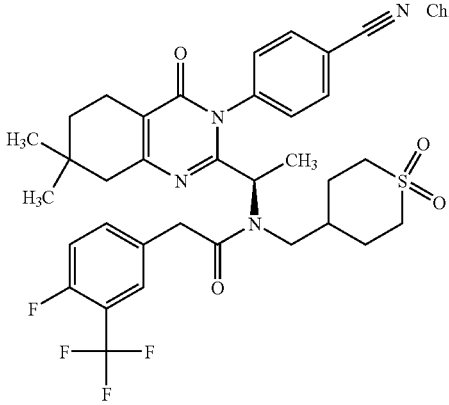 Chiral | 673.7 |
| 70 | 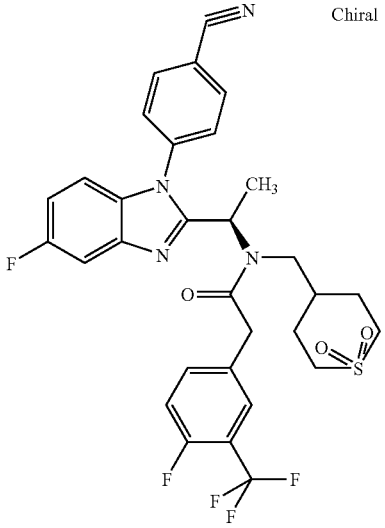 Chiral | 631.6 |
| 71 | 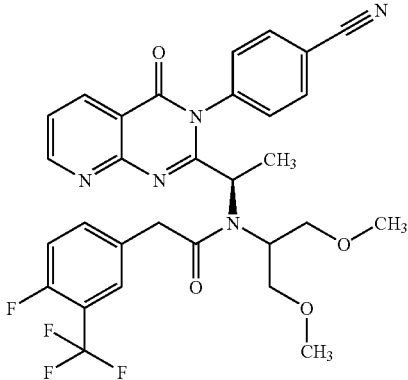 Chiral | 598.6 |

TABLE 1-continued

| Example | Molecular Formula | Characterization (Mass) MS + 1 |
|---------|-------------------|-------------------------------|
| 72 | | 594.6 |
| 73 | | 610.6 |
| 74 | | 638.6 |
| 75 | | 673.7 |

TABLE 1-continued

| Example | Molecular Formula | Characterization (Mass) MS + 1 |
|---|---|---|
| 76 | (structure, Chiral) | 644.7 |
| 77 | (structure, Chiral) | 656.7 |
| 78 | (structure, Chiral) | 639.7 |

TABLE 1-continued

| Example | Molecular Formula | Characterization (Mass) MS + 1 |
|---|---|---|
| 79 | (structure shown) Chiral | 667.8 |
| 80 | (structure shown) Chiral | 634.7 |
| 81 | (structure shown) Chiral | 615.6 |

TABLE 1-continued

| Example | Molecular Formula | Characterization (Mass) MS + 1 |
|---|---|---|
| 82 | | 614.6 |
| 83.01 | | |
| 83.02 | | |
| 83.03 | | |

TABLE 1-continued
| Example | Molecular Formula | Characterization (Mass) MS + 1 |
|---|---|---|
| 83.04 | 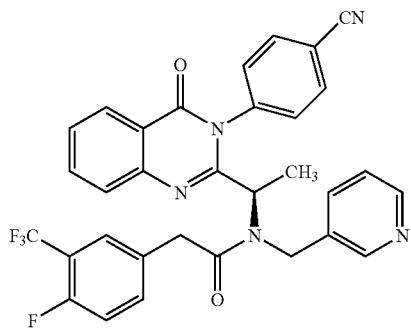 | |
| 83.05 | 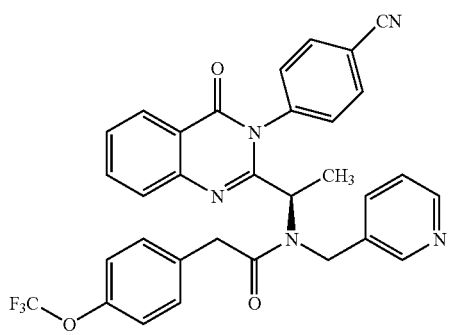 | |
| 83.06 | 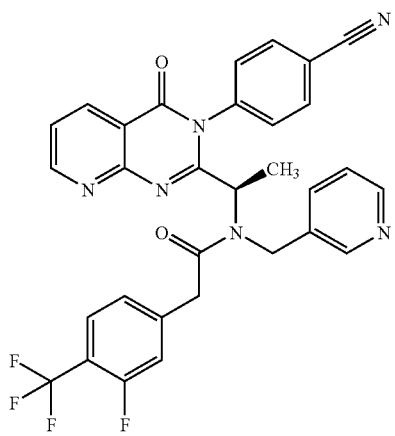 | |
| 83.07 | 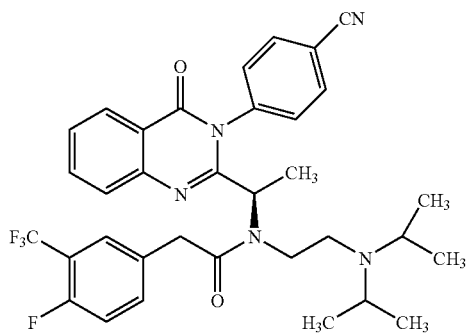 | |

TABLE 1-continued
| Example | Molecular Formula | Characterization (Mass) MS + 1 |
|---------|-------------------|-------------------------------|
| 83.08 | 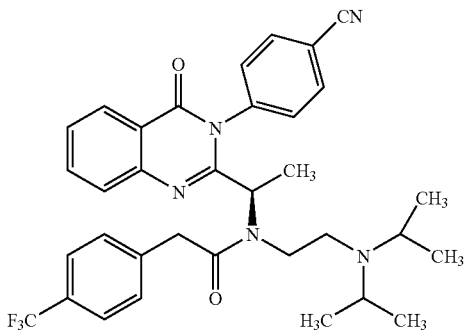 | |
| 83.09 | 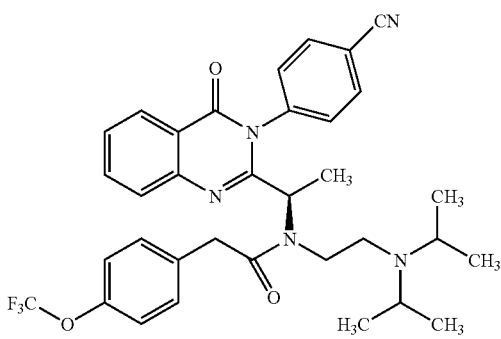 | |
| 83.10 | 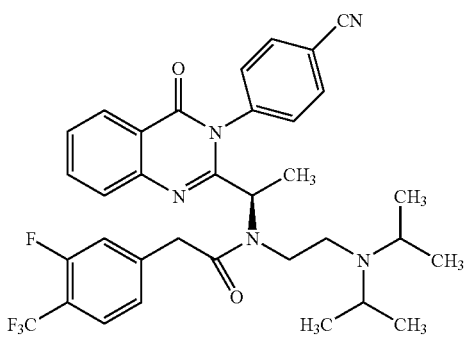 | |
| 83.11 | 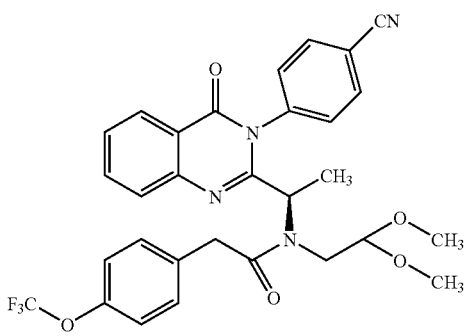 | |

TABLE 1-continued

| Example | Molecular Formula | Characterization (Mass) MS + 1 |
|---------|-------------------|-------------------------------|
| 83.12 | | |
| 83.13 | | |
| 84.01 | | 615.6 |
| 84.02 | Chiral | 615.6 |

TABLE 1-continued
| Example | Molecular Formula | Characterization (Mass) MS + 1 |
|---------|-------------------|-------------------------------|
| 84.03 | 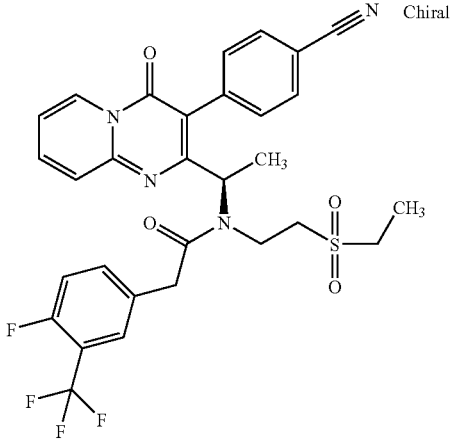 Chiral | 615.6 |
| 84.04 | 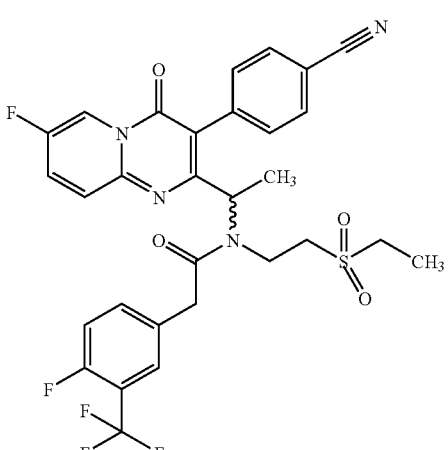 | 633.6 |
| 84.05 | 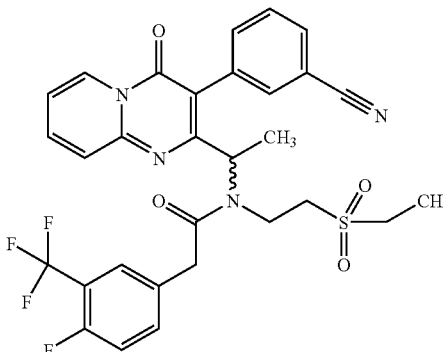 | 615.6 |

TABLE 1-continued
| Example | Molecular Formula | Characterization (Mass) MS + 1 |
|---|---|---|
| 85 | 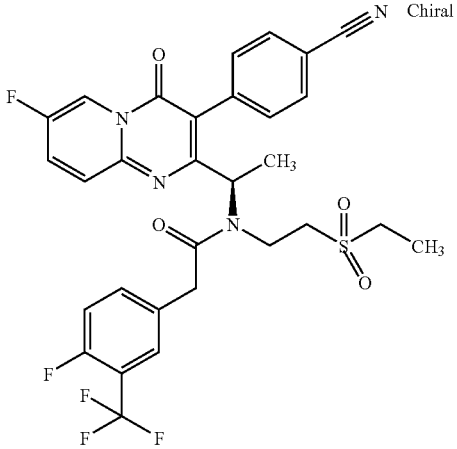 Chiral | 633.6 |
| 86 | 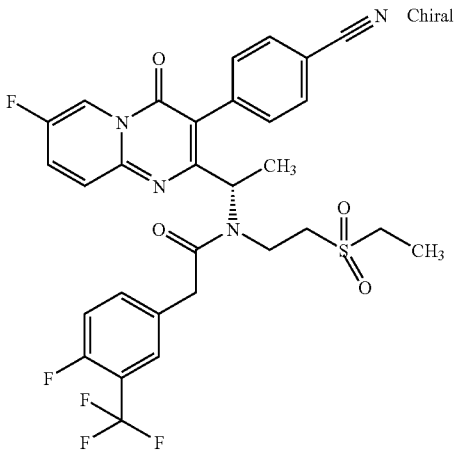 Chiral | 633.6 |
| 87 | 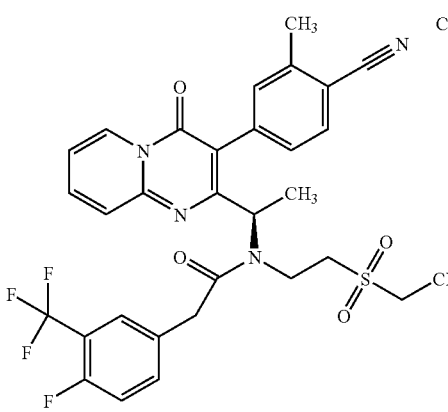 Chiral | 629.6 |

TABLE 1-continued

| Example | Molecular Formula | Characterization (Mass) MS + 1 |
|---|---|---|
| 88 | *(chiral structure)* | 615.6 |
| 89 | *(chiral structure)* | 609.7 |
| 90 | *(structure)* | 625.7 |

TABLE 1-continued

| Example | Molecular Formula | Characterization (Mass) MS + 1 |
|---|---|---|
| 91.01 | | 641.7 |
| 91.02 | | 592.6 |
| 91.04 | | 625.7 |

TABLE 1-continued
| Example | Molecular Formula | Characterization (Mass) MS + 1 |
|---------|-------------------|-------------------------------|
| 91.05 | 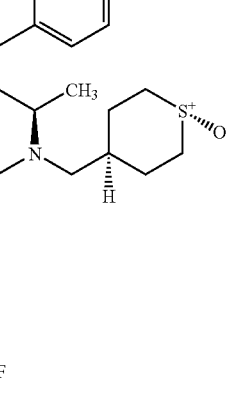 Chiral | 625.7 |
| 91.06 | 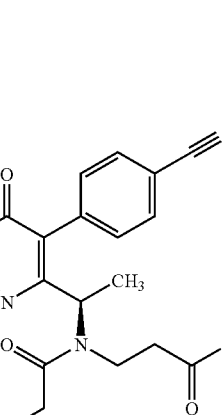 Chiral | 565.5 |
| 91.07 | 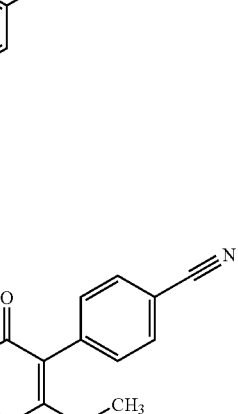 Chiral | 620.7 |

TABLE 1-continued
| Example | Molecular Formula | Characterization (Mass) MS + 1 |
|---|---|---|
| 91.08 | 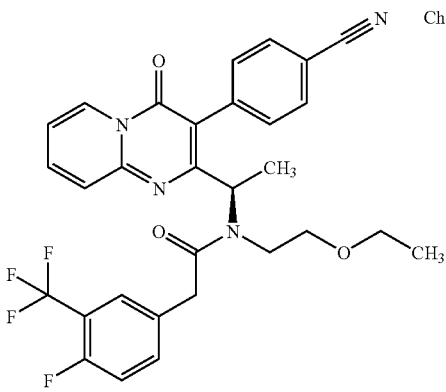 Chiral | 567.6 |
| 91.09 | 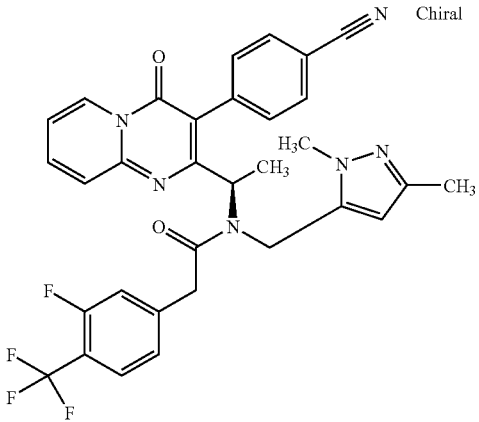 Chiral | 603.6 |
| 91.10 | 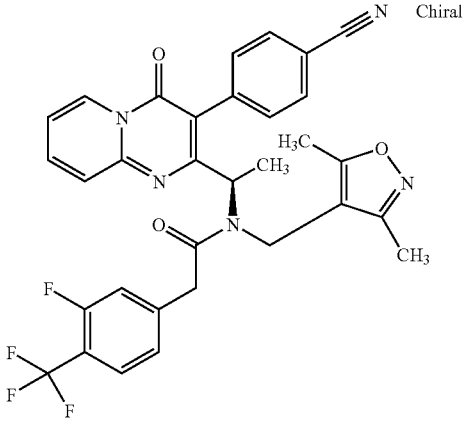 Chiral | 604.6 |

TABLE 1-continued

| Example | Molecular Formula | | Characterization (Mass) MS + 1 |
|---|---|---|---|
| 92 | (structure) | Chiral | 692.7 |
| 93 | (structure) | Chiral | 592.6 |

5.15. Example 15

The following examples provide comparative data exemplifying the advantages of the compounds of the present invention. CXCR modulators including compounds described herein and previously described in, e.g., WO 02/083143, were subject to CXCR3 binding assays, for activity in cell migration assays, and for their ability to inhibit cytochrome P450 3A ("CYP"). Moreover, compounds of the present invention, and those previously described, were studied under physiological conditions to assess their metabolism. These studies were conducted by incubating the particular compound in a liver microsomal preparation and analyzing the fractions for degradation or metabolites of the compound. Methods for conducting these assays are provided below. Results are provided in Tables 2-4.

CXCR3 Binding Assay: CXCR3 binding assays were conducted as previously described (see, e.g., Example 12 in WO 02/083143, incorporated herein by reference in its entirety), in the absence ("binding buffer") or presence of human plasma. Unless otherwise noted, all reagents used are available from commercial sources (e.g., Sigma-Aldrich, St. Louis, Mo., USA). Test compounds are diluted in DMSO to a concentration that is 40-times the intended final assay concentration; 5 µL are transferred to each well of a 96-well flat-bottomed polypropylene plate (e.g., from Greiner, Inc.). CXCR3-expressing cells obtained from ChemoCentryx were used in the assays to generate the data set forth below. The cells were resuspended in assay buffer (25 mM Hepes, 80 mM NaCl, 1 mM $CaCl_2$, 5 mM $MgCl_2$, 0.2% bovine serum albumin, pH 7.1, stored at 4° C.) at 5 million cells per mL; 100 µL of this cell suspension is then transferred to each well of a 96-well plate containing the diluted test compounds. $^{125}$I-labelled chemokine (purchased from commercial sources, e.g., Amersham, PE Life Sciences) is diluted in assay buffer to a concentration of approximately 60 µM; 100 µL of this chemokine solution is transferred to each well of a 96-well plate containing compounds and cell suspension. The plates are sealed with commercially available foil plate seals (e.g., from E&K Scientific), and stored at 4° C. for a period of 2 to 4 h, shaking gently. At the end of this incubation period, the contents of the assay plates are transferred to GF/B filter plates (Packard) that have been pre-coated by dipping into a solution containing 0.3% polyethyleneimine (Sigma-Aldrich), using a cell harvester (Packard), and washing twice with wash buffer (25 mM Hepes, 500 mM NaCl, 1 mM $CaCl_2$, 5 mM $MgCl_2$, pH 7.1, stored at room temperature). The filter plates are sealed on the bottom with plate seals (Packard), 50 µL of Microscint-20 scintillation fluid (Packard) is added to each well, and the top of the plates are sealed with clear plastic (TopSeal A, Packard). The plates are counted on a scintillation counter, such as a Packard Top-Count. To measure non-specific binding, 4 wells containing unlabelled "cold" chemokine were included on each 96-well plate. To measure maximum binding, 4 wells containing 5 μL of DMSO, 100 μL of cell suspension and 100 μL of $^{125}$I-labelled chemokine solution were included on each 96-well plate. Data were analyzed using commercially available software (e.g., Excel from Microsoft, Prism from GraphPad Software Inc.).

CYP Inhibition Assay: Time dependent CYP inhibition assays were initiated by incubating a test compound in 0.1 mM phosphate buffer containing pooled human liver microsomes (1 mg/mL protein) in the presence of NADPH for 0, 15 and 30 minutes. At each time point, an aliquot of the preincubation mixture was removed and added to 0.1 mM phosphate buffer containing marker substrate (midazolam) and fresh NADPH. The residual CYP activity, after the preincubation times of 0, 15, and 30 minutes, was monitored for 5 minutes. Data are expressed as the % 1-OH midazolam formation at 15 minutes compared to that formed at 0 minutes. Positive control was 15 μM troleandomycin (TAO), a known time-dependent CYP inhibitor, which reduced CYP activity by approximately 50% after 15 minutes preincubation. DMSO (vehicle control) caused an approximate 10% drop in CYP activity over 15 minutes.

In Vivo Metabolic Evaluation in Rat: To study the metabolic fate of test compounds in vivo, Sprague-Dawley (SD) rats were administered (orally gavage) test compound in suspension. Blood samples (~0.3 mL/timepoint) were collected at 1, 2, 4, 8, 24, 30 and 48 hours post-dose into EDTA containing tubes. All blood samples were collected via tail artery venipuncture under isofluorane anesthesia. Blood samples were processed for plasma by centrifugation and stored frozen until analysis (−20° to −70° C.). Samples were analyzed using a sensitive and selective LC/MS/MS method. Briefly, samples were prepared for analysis using protein precipitation. An aliquot of the resulting supernatant was subjected to LC/MS/MS analysis. Separation of the analytes from endogenous material was achieved using an reverse phase HPLC. Column effluent was monitored using a Sciex API 365 triple quadrapole mass spectrometer with a Sciex TurboIon Spray probe. Unknown concentrations of testing articles were determined using a calibration curve from 1 to 2000 ng/mL.

I-TAC migration assay: Human peripheral blood mononuclear cells (PBMCs) were activated with OKT3 (purified by AB solutions from hybridoma cell line OKT3 (ATCC CRL-8001)) and IL-2 (Peprotech, Inc., Rocky Hill, N.J., USA). After fourteen days, the cells were loaded with chloromethyl-fluoroscein-diacetate (CMFDA) (Molecular Probes, Inc.) by incubating the activated PBMCs in 1 ng/mL CMFDA for >1.5 hours at 37° C. in a tissue culture incubator. While cells were loading, the test compounds were diluted in DMSO to a concentration that is 100-times the intended final assay concentration. Next, 100 ng/mL of human ITAC (Peprotech) in human plasma (EDTA, drug free, Biological Specialty Corp) was prepared. Test compounds were added to the human ITAC preparation. Cells were washed once in prewarmed (37° C.) RPMI (Invitrogen) media with 0.5% BSA and resuspended to 5 million cells/ml in human plasma. The test compounds were added to the PBMCs. A 96-well chemotaxis migration plate (NeuroProbe, Inc.) was assembled by adding, per well, 30 uL of ITAC/compound mixture in the lower chamber, placing the impermeable membrane on top of the ITAC/compound well, and adding 50 uL of the PBMC/compound mixture to the well. The plates were covered and incubated in a humidified tissue culture incubator for 2.5 hours. A standard curve of CMFDA-loaded cells to be used as a reference for the test plates was prepared. Migration plates were disassembled and are read in a fluorometric plate reader set to 475 nm absorbance, 517 nm emission. The fluorometric reading was converted to cell number using the standard curve and calculating the percentage of migrating cells.

It will be understood that other assays may be used to identify compounds that modulate CXCR3 chemokine receptor activity, for example, binding assays (see, e.g., Weng et al. (1998) *J. Biol. Chem.* 273:18288-18291, Campbell et al. (1998) *J. Cell Biol.* 141:1053-1059, Endres et al. (1999) *J. Exp. Med.* 189:1993-1998 and Ng et al. (1999) *J. Med. Chem.* 42:4680-4694), calcium flux assays (see, e.g., Wang et al. (2000) *Mol. Pharm.* 57:1190-1198 and Rabin et al. (1999) *J. Immunol.* 162:3840-3850) and chemotaxis assays (see, e.g., Albanesi et al. (2000) *J. Immunol.* 165:1395-1402 and Loetscher et al. (1998) *Eur. J. Immunol.* 28:3696-3705).

TABLE 2

| Structure tested: | (structure with OEt) | (structure with OH) |
|---|---|---|
| CXCR3 Binding Buffer IC50 (nM) | 1 | |
| CXCR3 Binding Plasma IC50 (nM) | 7 | |
| I-TAC Migration IC50 (nM) | 22 | |
| Time Dependent CYP3A4 Inhibition | NO | Yes |

TABLE 2-continued

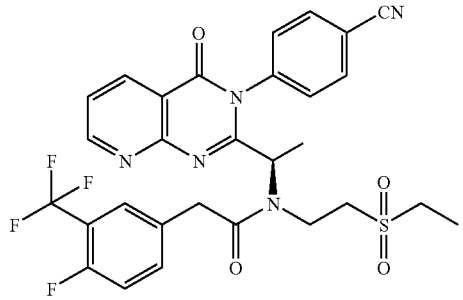

Structure tested:

| | |
|---|---|
| CXCR3 Binding Buffer IC50 (nM) | 11 |
| CXCR3 Binding Plasma IC50 (nM) | 25 |
| I-TAC Migration IC50 (nM) | 120 |
| Time Dependent CYP3A4 Inhibition | NO |

TABLE 3

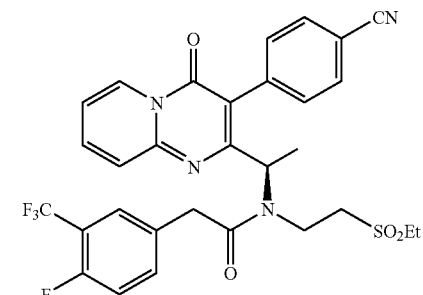

| | | |
|---|---|---|
| Structure tested: | | |
| CXCR3 Binding Buffer IC50 (nM) | 1 | 816 |
| CXCR3 Binding Plasma IC50 (nM) | 57 | 4080 |
| I-TAC Migration IC50 (nM) | 183 | |
| Time Dependent CYP3A4 Inhibition | NO | Yes |

| | |
|---|---|
| Structure tested: | |
| CXCR3 Binding Buffer IC50 (nM) | 2 |
| CXCR3 Binding Plasma IC50 (nM) | 17 |
| I-TAC Migration IC50 (nM) | 41 |
| Time Dependent CYP3A4 Inhibition | NO |

TABLE 4

| Structure tested: | (OEt-substituted imidazopyrimidine structure) | (OH-substituted imidazopyrimidine structure) |
|---|---|---|
| CXCR3 Binding Buffer IC50 (nM) | 4 | 10000 |
| CXCR3 BindingPlasma IC50 (nM) | 70 | 10000 |
| I-TAC Migration IC50 (nM) | 1500 | |
| Time Dependent CYP3A4 Inhibition | NO | Yes |

| Structure tested: | (CN-substituted imidazopyrimidine structure) |
|---|---|
| CXCR3 Binding Buffer IC50 (nM) | 10 |
| CXCR3 BindingPlasma IC50 (nM) | 49 |
| I-TAC Migration IC50 (nM) | 83 |
| Time Dependent CYP3A4 Inhibition | NO |

Tables 2-4 exemplify advantages of the compounds of the invention in terms of CXCR3 binding, I-TAC migration and CYP3A inhibition. CYP3A inhibition studies indicated that compounds of the invention do not inhibit CYP3A, a desirable feature in a CXCR3 antagonist. Moreover, compounds of the invention were found to be potent CXCR3 antagonists in terms of CXCR3 binding and I-TAC migration activity.

When incubated under physiological conditions (for example, in liver microsomal preparations), compounds of the invention did not metabolize. When incubated under similar physiological conditions, the alkoxy group on para-alkoxyphenyl structures metabolized to a hydroxyl group, thereby reducing the efficacy otherwise associated with the parent para-alkoxyphenyl structures. As shown in Tables 2-4, para-hydroxyphenyl structures were associated with a time-dependent inhibition of CYP.

CXCR3 binding studies show that, in general, the $IC_{50}$ of all CXCR3 antagonists will increase when human plasma is included in the binding assay as compared to a binding assay performed in the absence of human plasma. However, compounds of the invention were more often able to maintain CXCR3 efficacy, i.e., compounds of the invention showed less of an increase in $IC_{50}$, than, for example, para-alkoxyphenyl structures.

Pharmacokinetics of exemplary compounds of the invention was assessed in rats. These parameters has shown in Table 5.

TABLE 5

| Structure | Rat PK(IV) MRT Cl Vdss | Rat PK PO CMAX MRT F % |
|---|---|---|
| 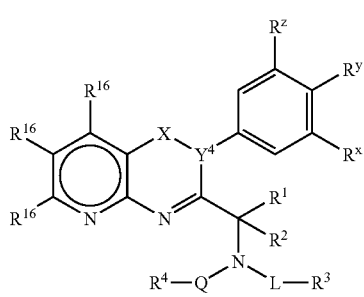 | 0.53<br>2.38<br>1.12 | 444<br>1.5<br>47.2 |
| 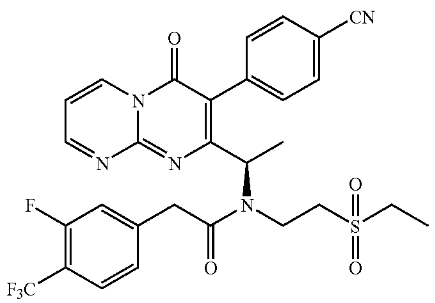 | 1.37<br>0.235<br>0.31 | 587<br>3.96<br>24.0 |

All publications and patent applications cited in this specification are herein incorporated by reference as if each individual publication or patent specification were specifically and individually indicated to be incorporated by reference. Although the foregoing invention has been described in some detail by way of illustration and example for purposes of clarity of understanding, it will be readily apparent tot those of ordinary skill in the art in light of the teaching of this invention that certain changes and modifications may be made thereto without departing from the spirit or scope of the appended claims.

What is claimed:

1. A compound of the formula (IV);

IV or pharmaceutically acceptable salt thereof, wherein

X is —C(O)—;

$Y^4$ is N;

L is a member selected from the group consisting of C(O)—($C_1$-$C_8$)alkylene, ($C_1$-$C_8$)alkylene and ($C_2$-$C_8$) heteroalkylene;

Q a member selected from the group consisting of ($C_1$-$C_8$) alkylene, —C(O)—, —OC(O)—, —N($R^8$)C(O)—, —$CH_2$CO—, —$CH_2$SO—, and —$CH_2SO_2$—;

optionally L and Q together with the nitrogen atom to which they are each bonded can be linked together to form a 5- or 6-membered heterocyclic group having from 1 to 3 heteroatoms;

$R^1$ and $R^2$ are independently a member selected from the group consisting of H, ($C_1$-$C_8$)alkyl, ($C_2$-$C_8$)heteroalkyl, aryl and heteroaryl, or optionally are combined together with the carbon atom to which they bonded to form a 3 to 8-membered ring having from 0 to 2 heteroatoms as ring members;

$R^3$ is a member selected from the group consisting of hydrogen, hydroxy, ($C_1$-$C_8$)alkoxy, amino, ($C_1$-$C_8$) alkylamino, di($C_1$-$C_8$)alkylamino, ($C_1$-$C_{20}$)alkyl, ($C_2$-$C_8$)heteroalkyl, cyclo($C_3$-$C_9$)heteroalkyl, amidino, guanidino, ureido, cyano, heteroaryl, —CON$R^9R^{10}$ and —$CO_2R^{11}$;

$R^4$ is a member selected from the group consisting of ($C_2$-$C_{20}$)alkyl, ($C_2$-$C_{20}$)heteroalkyl, heteroaryl, aryl, heteroaryl($C_1$-$C_6$)alkyl, heteroaryl($C_2$-$C_6$)heteroalkyl, aryl ($C_1$-$C_6$)alkyl and aryl($C_2$-$C_6$)heteroalkyl;

$R^8$ is selected from the group consisting of H, ($C_1$-$C_8$)alkyl, ($C_2$-$C_8$)heteroalkyl, heteroaryl and aryl;

each $R^9$, $R^{10}$ and $R^{11}$ is independently selected from the group consisting of H, ($C_1$-$C_8$)alkyl, ($C_2$-$C_8$)heteroalkyl, heteroaryl, aryl, heteroaryl($C_1$-$C_6$)alkyl, heteroaryl($C_2$-$C_8$)heteroalkyl, aryl($C_1$-$C_8$)alkyl and aryl ($C_2$-$C_8$)heteroalkyl;

$R^{16}$ is selected from the group consisting of H, halogen, ($C_1$-$C_8$)alkyl, ($C_2$-$C_8$)heteroalkyl, fluoro($C_1$-$C_4$)alkyl, aryl, heteroaryl, aryl($C_1$-$C_8$)alkyl, heteroaryl($C_1$-$C_8$) alkyl, —OR', —OC(O)R', —NR'R'', —SR', —R', —CN, —$NO_2$, —$CO_2$R', —CONR'R'', —C(O)R', —OC(O)NR'R'', —NR''C(O)R', —NR''C(O)$_2$R', —NR'—C(O)NR''R''', —NH—C($NH_2$)=NH, —NR'C ($NH_2$)=NH, —NHC($NH_2$)=NR', —S(O)R', —S(O)$_2$R', —S(O)$_2$NR'R'', —$N_3$, —CH(Ph)$_2$, perfluoro($C_1$-$C_4$)alkoxy, and perfluoro($C_1$-$C_4$)alkyl, wherein R', R'' and R''' are each independently selected from H, ($C_1$-$C_8$)alkyl, ($C_2$-$C_8$)heteroalkyl, unsubstituted aryl, unsubstituted heteroaryl, (unsubstituted aryl)-($C_1$-$C_4$)alkyl, and (unsubstituted aryl)oxy-($C_1$-$C_4$) alkyl; and $R^x$, $R^y$ and $R^z$ are each independently H, F or cyano, wherein at least one of $R^x$, $R^y$ and $R^z$ is cyano;

with the proviso that the compound is not

N-{1R-[3-(4-cyanophenyl)-4-oxo-3,4-dihydro-pyrido[2,3-d]pyrimidin-2-yl]-ethyl}-N-(1H-imidazol-2-ylmethyl)-2-(4-trifluoromethyl-phenyl)-acetamide;

N-{1R-[3-(4-cyanophenyl)-4-oxo-3,4-dihydro-pyrido[2,3-d]pyrimidin-2-yl]-ethyl}-N-(pyridin-3-ylmethyl)-2-(4-trifluoromethyl-phenyl)-acetamide;

N-{1R-[3-(4-cyanophenyl)-4-oxo-3,4-dihydro-pyrido[2,3-d]pyrimidin-2-yl]-ethyl}-N-(1-methyl-1H-imidazol-2-ylmethyl)-2-(4-trifluoromethyl-phenyl)-acetamide; or (R)-N-{1-[3-(4-cyanophenyl)-4-oxo-3,4-dihydro-pyrido[2,3-d]pyrimidin-2-yl]-ethyl}-2-(4-fluoro-3-trifluoromethyl-phenyl)-N-pyridin-3-ylmethyl-acetamide.

2. The compound of claim 1, wherein $R^3$ is a member selected from the group consisting of —$SO_2CH_3$, —$SO_2CH_2CH_3$,

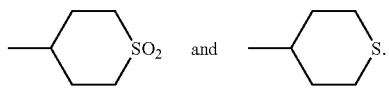 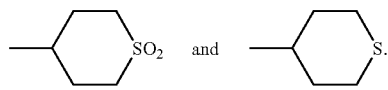

3. The compound of claim 1, wherein $R^1$, $R^z$ and $R^x$ are H, L is methylene or ethylene, Q is —CH$_2$CO—, and $R^4$ is aryl or heteroaryl.

4. The compound of claim 1, wherein Q-$R^4$ taken together is

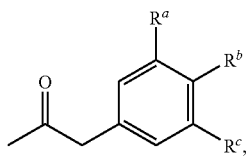

where $R^a$, $R^b$ and $R^c$ are each independently —H, halogen, —CN, —OCF$_3$, or —CF$_3$.

5. The compound of claim 4, wherein $R^a$ is —CF$_3$, $R^b$ is —F and $R^c$ is —H.

6. The compound of claim 1 having the formula (V):

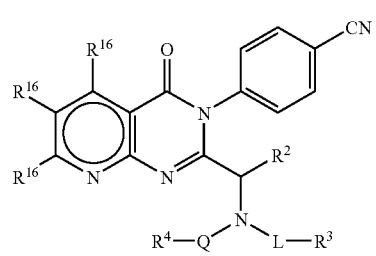

wherein each $R^{16}$ is independently H, halogen, (C$_1$-C$_8$)alkyl, (C$_2$-C$_8$)heteroalkyl, fluoro(C$_1$-C$_4$)alkyl, aryl, heteroaryl, aryl(C$_1$-C$_8$)alkyl or heteroaryl(C$_1$-C$_8$)alkyl.

7. The compound of claim 1, wherein $R^1$ and $R^x$ are H; and each $R^{16}$ is a member independently selected from the group consisting of H, halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NHC(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, wherein R', R" and R"' are each independently selected from H, (C$_1$-C$_8$)alkyl, (C$_2$-C$_8$)heteroalkyl, unsubstituted aryl, unsubstituted heteroaryl, (unsubstituted aryl)-(C$_1$-C$_4$)alkyl, and (unsubstituted aryl)oxy-(C$_1$-C$_4$)alkyl.

8. The compound of claim 7, wherein $R^3$ is a member selected from the group consisting of —SO$_2$CH$_3$, —SO$_2$CH$_2$CH$_3$, 9. The compound of claim 7, wherein Q is —CH$_2$CO—, and $R^4$ is aryl or heteroaryl.

10. The compound of claim 1 having the formula (VIII):

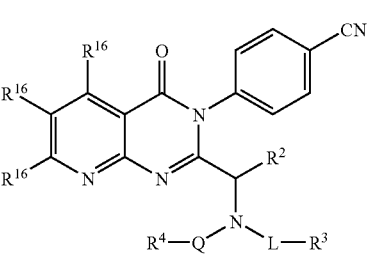

11. The compound of claim 10, wherein $R^3$ is a member selected from the group consisting of —SO$_2$CH$_3$, —SO$_2$CH$_2$CH$_3$,

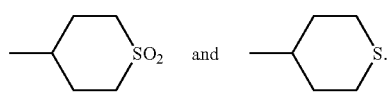

12. The compound of claim 10 wherein Q-$R^4$ taken together is

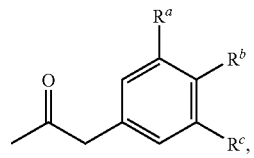

where $R^a$, $R^b$ and $R^c$ are each independently H, halogen, —OCF$_3$, or —CF$_3$.

13. The compound of claim 10 wherein the compound is

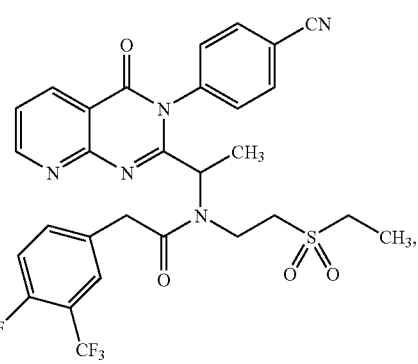

or a pharmaceutically acceptable salt thereof.

14. The compound of claim 10 wherein the compound is selected from the group consisting of

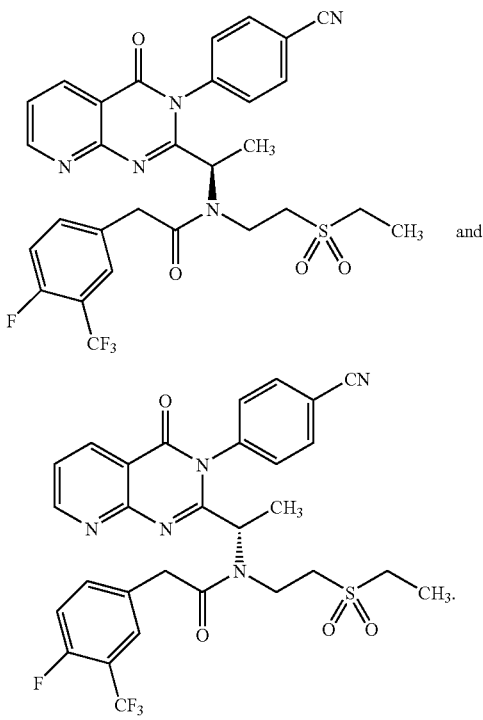

and

15. The compound of claim 10 having the formula (VIIIa) or (VIIIb):

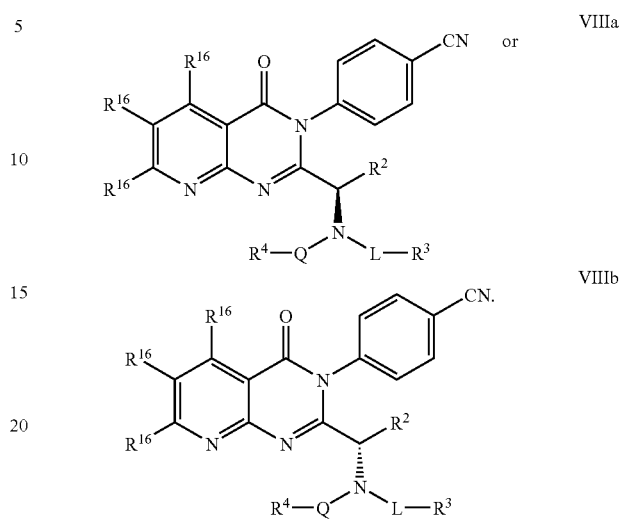

16. A pharmaceutical composition comprising the compound of claim 1, and a pharmaceutically acceptable excipient, carrier or diluent.

17. The compound of claim 10, wherein each $R^{16}$ is hydrogen, halogen, hydroxyl, methyl, ethyl, cyano, trihalomethyl, methoxy or ethoxy.

* * * * *